US012667353B2

(12) United States Patent
Baron et al.

(10) Patent No.: US 12,667,353 B2
(45) Date of Patent: Jun. 30, 2026

(54) TISSUE CLOSURE SYSTEMS

(71) Applicant: Ladera Medical, LLC, Menlo Park, CA (US)

(72) Inventors: Scott J. Baron, Menlo Park, CA (US); Brian Domecus, San Carlos, CA (US); Jonathan M. Olson, San Jose, CA (US); David Trask, Redwood City, CA (US); Brian A. Ellingwood, Sunnyvale, CA (US); Dan J. Hammersmark, San Mateo, CA (US); Douglas S. Sutton, Pacifica, CA (US); Ben F. Brian, III, Menlo Park, CA (US); Michael Barrett, Campbell, CA (US)

(73) Assignee: Ladera Medical, LLC, Menlo Park, CA (US)

( * ) Notice: Subject to any disclaimer, the term of this patent is extended or adjusted under 35 U.S.C. 154(b) by 120 days.

(21) Appl. No.: 18/631,901

(22) Filed: Apr. 10, 2024

(65) Prior Publication Data

US 2024/0350135 A1 Oct. 24, 2024

Related U.S. Application Data

(60) Provisional application No. 63/495,454, filed on Apr. 11, 2023.

(51) Int. Cl.
*A61B 17/04* (2006.01)
*A61B 17/00* (2006.01)
(Continued)

(52) U.S. Cl.
CPC .... *A61B 17/0469* (2013.01); *A61B 17/00234* (2013.01); *A61B 17/0401* (2013.01);
(Continued)

(58) Field of Classification Search
CPC ............ A61B 17/0469; A61B 17/0482; A61B 17/0401; A61B 17/0057; A61B 17/06061;
(Continued)

(56) References Cited

U.S. PATENT DOCUMENTS 5,507,755 A 4/1996 Gresl et al.
5,527,322 A 6/1996 Klein et al.
(Continued)

FOREIGN PATENT DOCUMENTS

WO WO 2021/151103 7/2021
WO WO 2024/215763 10/2024

*Primary Examiner* — Mohamed G Gabr
*Assistant Examiner* — Khoa Tan Le
(74) *Attorney, Agent, or Firm* — Levine Bagade Han LLP

(57) ABSTRACT

Tissue closure systems are disclosed wherein one variation generally includes a handle, a proximal catheter segment extending from the handle, a deployment segment coupled to the proximal catheter segment, and a distal catheter segment pivotably coupled to the deployment segment such that the distal catheter segment is rotatable at an angle relative to the proximal catheter segment. A receiver member positioned within the deployment segment is configurable between a low-profile configuration and a deployed configuration. Two or more forward needle members and two or more rear needle members are extendable distally from a first side and a second side of the proximal catheter segment. The two or more forward needle members are receivable into the two or more openings along the first receiver portion and the two or more rear needle members are receivable into the two or more openings along the second receiver portion.

15 Claims, 47 Drawing Sheets

(51) Int. Cl.
　　*A61B 17/06*　　　　(2006.01)
　　*A61B 90/00*　　　　(2016.01)

(52) U.S. Cl.
　　CPC .... *A61B 17/0482* (2013.01); *A61B 17/06061*
　　　　(2013.01); *A61B 90/08* (2016.02); *A61B*
　　　　*2017/00238* (2013.01); *A61B 2017/00314*
　　　　(2013.01); *A61B 2017/00336* (2013.01); *A61B*
　　　　*2017/00367* (2013.01); *A61B 2017/00438*
　　　　(2013.01); *A61B 2017/00477* (2013.01); *A61B*
　　　　*2017/00738* (2013.01); *A61B 2017/00778*
　　　　(2013.01); *A61B 2017/00862* (2013.01); *A61B*
　　　　*2017/0409* (2013.01); *A61B 2017/0414*
　　　　(2013.01); *A61B 2017/0424* (2013.01); *A61B*
　　　　*2017/0453* (2013.01); *A61B 2017/0454*
　　　　(2013.01); *A61B 2017/0458* (2013.01); *A61B*
　　　　*2017/047* (2013.01); *A61B 2017/0472*
　　　　(2013.01); *A61B 2017/0496* (2013.01); *A61B*
　　　　*2090/0808* (2016.02)

(58) Field of Classification Search
　　CPC .. A61B 2017/00336; A61B 2017/0409; A61B
　　　　2017/0414; A61B 2017/0496; A61B
　　　　2017/0488; A61B 2017/0472
　　See application file for complete search history.

(56)　　　　　　References Cited

U.S. PATENT DOCUMENTS

| | | | |
|---|---|---|---|
| 5,746,755 | A | 5/1998 | Wood et al. |
| 5,792,152 | A | 8/1998 | Klein et al. |
| 5,797,929 | A | 8/1998 | Andreas et al. |
| 5,902,311 | A * | 5/1999 | Andreas ............. A61B 17/0057 |
| | | | 606/139 |
| 5,921,994 | A | 7/1999 | Andreas et al. |
| 6,117,145 | A | 9/2000 | Wood et al. |
| 6,136,010 | A | 10/2000 | Modesitt et al. |
| 6,206,893 | B1 | 3/2001 | Klein et al. |
| 6,517,553 | B2 | 2/2003 | Klein et al. |
| 6,746,457 | B2 | 6/2004 | Dana et al. |
| 7,029,480 | B2 | 4/2006 | Klein et al. |
| 7,094,246 | B2 | 8/2006 | Anderson et al. |
| 7,147,646 | B2 | 12/2006 | Dana et al. |
| 7,153,312 | B1 | 12/2006 | Torrie et al. |
| 7,235,086 | B2 * | 6/2007 | Sauer ................... A61B 1/0014 |
| | | | 606/151 |
| 7,445,626 | B2 | 11/2008 | Songer et al. |
| 7,594,923 | B2 | 9/2009 | Fallin et al. |
| 7,641,694 | B1 | 1/2010 | Goble et al. |
| 7,842,048 | B2 | 11/2010 | Ma |
| 7,842,051 | B2 | 11/2010 | Dana et al. |
| 7,862,584 | B2 | 1/2011 | Lyons et al. |
| 7,918,867 | B2 | 4/2011 | Dana et al. |
| 7,992,571 | B2 | 8/2011 | Gross et al. |
| 8,137,364 | B2 | 3/2012 | Zung et al. |
| 8,211,122 | B2 | 7/2012 | Mcintosh |
| 8,211,123 | B2 | 7/2012 | Gross et al. |
| 8,252,008 | B2 | 8/2012 | Ma |
| 8,361,088 | B2 | 1/2013 | Mcintosh |
| 8,398,680 | B2 | 3/2013 | Sauer et al. |
| 8,480,691 | B2 | 7/2013 | Dana et al. |
| 8,574,244 | B2 | 11/2013 | Reynolds |
| 8,585,720 | B2 | 11/2013 | Gross et al. |
| 8,715,303 | B2 | 5/2014 | Voss et al. |
| 9,155,535 | B2 | 10/2015 | Mcintosh |
| 9,241,613 | B2 | 1/2016 | Hsu et al. |
| 9,241,707 | B2 | 1/2016 | Roorda et al. |
| 9,282,960 | B2 | 3/2016 | Ma |
| 9,301,746 | B2 | 4/2016 | Fortson |
| 9,301,748 | B2 | 4/2016 | Heneveld |
| 9,320,515 | B2 | 4/2016 | Dana et al. |
| 9,364,209 | B2 | 6/2016 | Voss |
| 9,393,011 | B2 | 7/2016 | Heneveld |

| | | | |
|---|---|---|---|
| 9,592,045 | B2 | 3/2017 | Voss et al. |
| 9,668,724 | B2 | 6/2017 | Tang et al. |
| 9,668,727 | B2 | 6/2017 | Heneveld |
| 9,750,494 | B2 | 9/2017 | Gross et al. |
| 9,757,108 | B2 | 9/2017 | Fortson |
| 10,111,653 | B2 | 10/2018 | Roorda et al. |
| 10,143,463 | B2 | 12/2018 | Dana et al. |
| 10,194,901 | B2 | 2/2019 | Tang et al. |
| 10,201,345 | B2 | 2/2019 | Weng et al. |
| 10,231,730 | B2 | 3/2019 | Heneveld |
| 10,299,774 | B2 | 5/2019 | Heneveld |
| 10,307,144 | B2 | 6/2019 | Wu et al. |
| 10,314,566 | B2 | 6/2019 | Hsu et al. |
| 10,327,760 | B2 | 6/2019 | Voss et al. |
| 10,327,761 | B2 | 6/2019 | Ho et al. |
| 10,426,449 | B2 | 10/2019 | Fortson |
| 10,478,176 | B2 | 11/2019 | Ono et al. |
| 10,507,019 | B2 | 12/2019 | Gross et al. |
| 10,512,454 | B2 | 12/2019 | Heneveld |
| 10,537,312 | B2 | 1/2020 | Voss |
| 10,595,857 | B2 | 3/2020 | Heneveld |
| 10,603,027 | B2 | 3/2020 | Sauer |
| 10,624,628 | B2 | 4/2020 | Tang et al. |
| 10,660,636 | B2 | 5/2020 | Heneveld |
| 10,702,263 | B2 | 7/2020 | Heneveld |
| 10,806,439 | B2 | 10/2020 | Fortson |
| 10,959,720 | B2 | 3/2021 | Juan et al. |
| 10,980,531 | B2 | 4/2021 | Roorda et al. |
| 11,154,294 | B2 | 10/2021 | Heneveld |
| 11,213,389 | B2 | 1/2022 | Sauer |
| 11,219,447 | B2 | 1/2022 | Juan et al. |
| 11,229,427 | B2 | 1/2022 | Heneveld |
| 11,389,152 | B2 | 7/2022 | Gilmore et al. |
| 11,684,357 | B2 | 6/2023 | Munday |
| 12,029,414 | B2 | 7/2024 | Guo et al. |
| 2001/0031973 | A1 * | 10/2001 | Nobles ............... A61B 17/0057 |
| | | | 606/144 |
| 2002/0045908 | A1 * | 4/2002 | Nobles ............... A61B 17/0057 |
| | | | 606/144 |
| 2005/0251208 | A1 | 11/2005 | Elmer et al. |
| 2005/0288711 | A1 | 12/2005 | Fallin et al. |
| 2006/0229623 | A1 | 10/2006 | Bonutti et al. |
| 2007/0282354 | A1 * | 12/2007 | McIntosh ........... A61B 17/0469 |
| | | | 606/148 |
| 2008/0045976 | A1 | 2/2008 | Gibbons et al. |
| 2008/0045979 | A1 * | 2/2008 | Ma ..................... A61B 17/0482 |
| | | | 606/144 |
| 2010/0121349 | A1 | 5/2010 | Meier et al. |
| 2010/0130990 | A1 | 5/2010 | Saliman |
| 2011/0046644 | A1 | 2/2011 | Mcclurg et al. |
| 2013/0023905 | A1 | 1/2013 | Kubalak |
| 2013/0035699 | A1 | 2/2013 | Heneveld et al. |
| 2013/0035700 | A1 | 2/2013 | Heneveld |
| 2013/0035701 | A1 | 2/2013 | Heneveld et al. |
| 2013/0035702 | A1 | 2/2013 | Heneveld |
| 2013/0144316 | A1 * | 6/2013 | McCrea ............. A61B 17/0057 |
| | | | 606/145 |
| 2018/0235603 | A1 | 8/2018 | Heneveld |
| 2019/0261964 | A1 | 8/2019 | Zung et al. |
| 2020/0029947 | A1 | 1/2020 | Bagaoisan et al. |
| 2020/0046343 | A1 | 2/2020 | Kramer |
| 2020/0060664 | A1 | 2/2020 | Fortson et al. |
| 2020/0155144 | A1 | 5/2020 | Heneveld |
| 2020/0281583 | A1 | 9/2020 | Heneveld |
| 2021/0052270 | A1 | 2/2021 | Fortson |
| 2021/0121173 | A1 | 4/2021 | Kramer et al. |
| 2021/0145421 | A1 | 5/2021 | Hauck et al. |
| 2021/0315564 | A1 | 10/2021 | Sauer et al. |
| 2021/0401427 | A1 | 12/2021 | Binmoeller et al. |
| 2022/0008064 | A1 | 1/2022 | Heneveld |
| 2022/0104799 | A1 | 4/2022 | Heneveld |
| 2022/0257238 | A1 | 8/2022 | Khairkhahan et al. |
| 2023/0210520 | A1 | 7/2023 | Dale et al. |
| 2024/0081800 | A1 | 3/2024 | Iamberger et al. |
| 2024/0115257 | A1 | 4/2024 | Bromley |
| 2024/0341745 | A1 | 10/2024 | Baron et al. |
| 2024/0341751 | A1 | 10/2024 | Baron et al. |

* cited by examiner

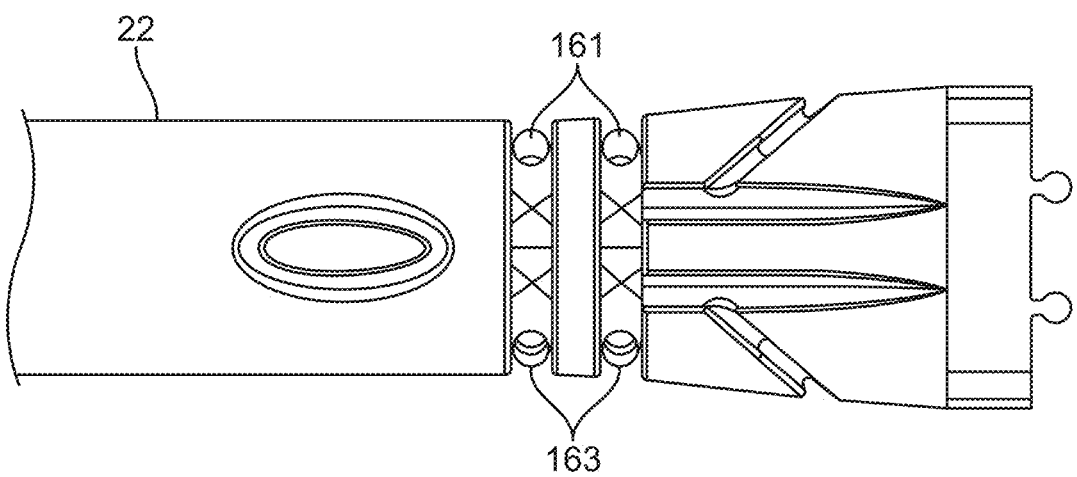
FIG. 30A
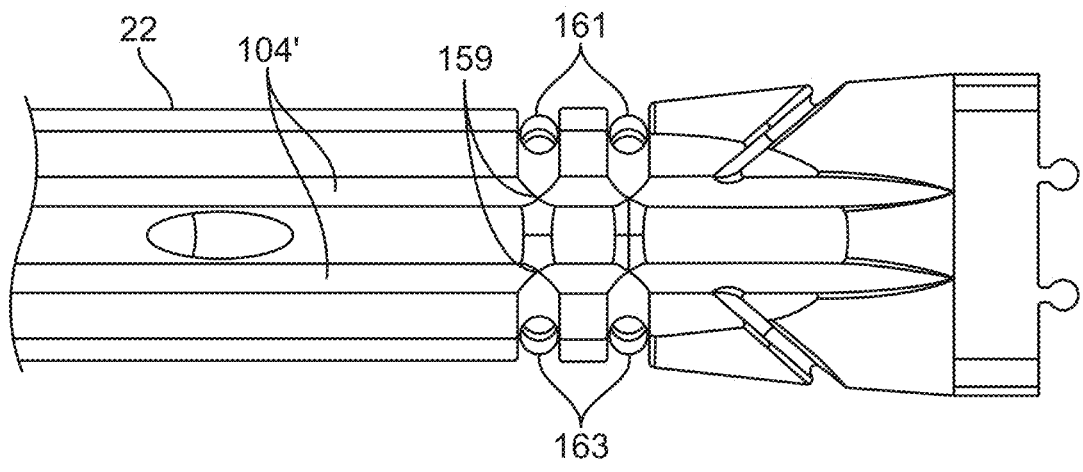
FIG. 30B
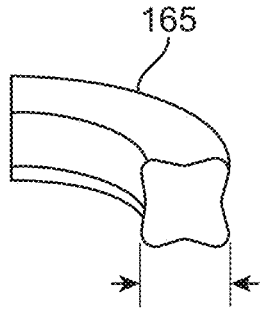 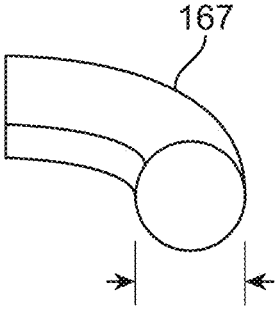 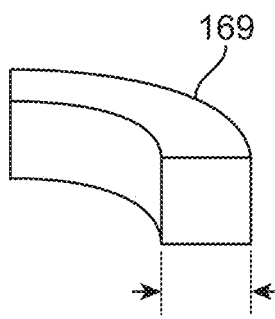
FIG. 31A      FIG. 31B      FIG. 31C

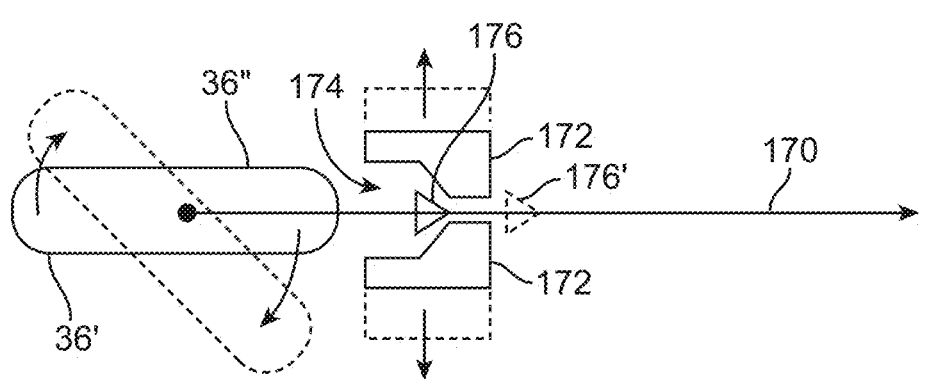
FIG. 33A
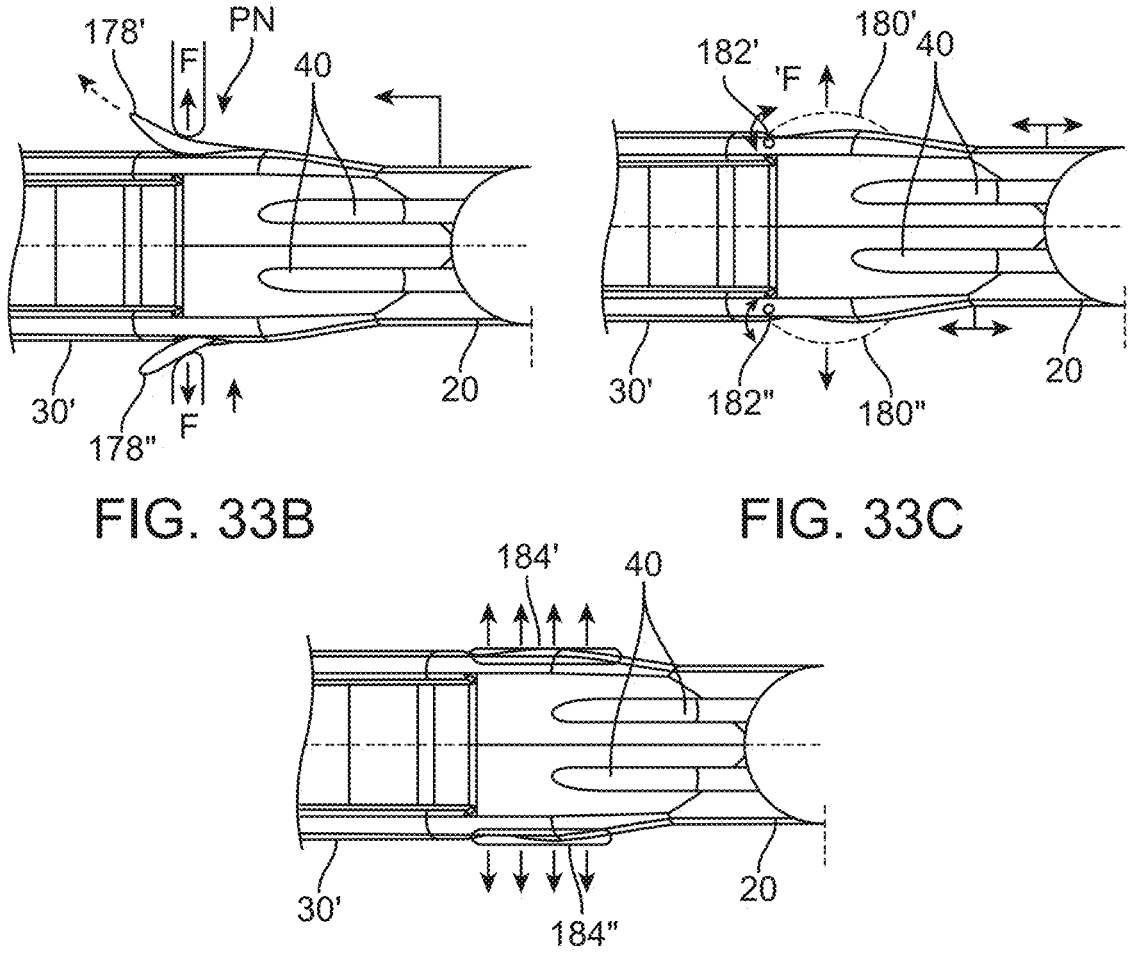
FIG. 33B
FIG. 33C
FIG. 33D

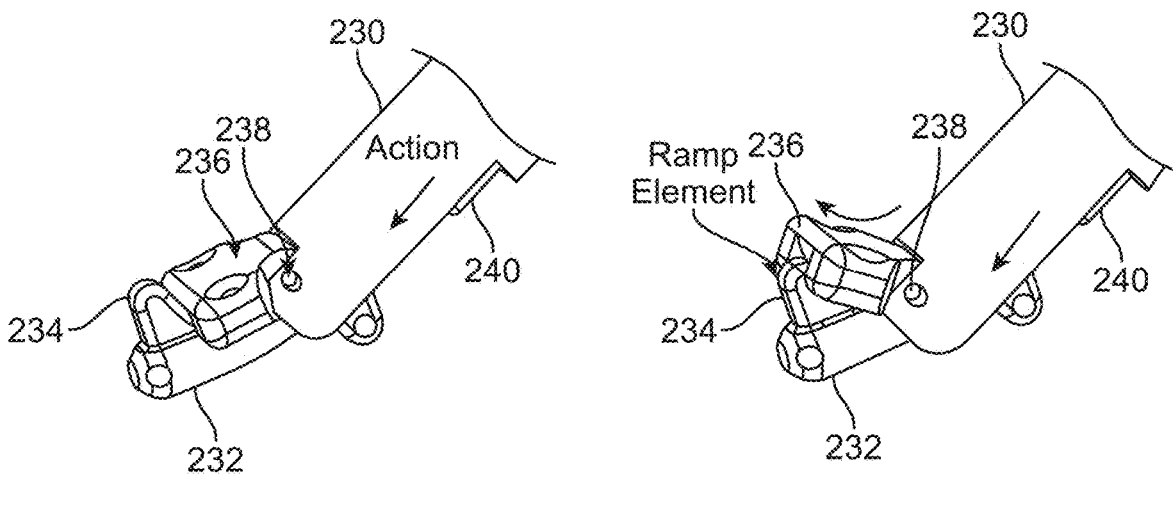
FIG. 36A
FIG. 36B
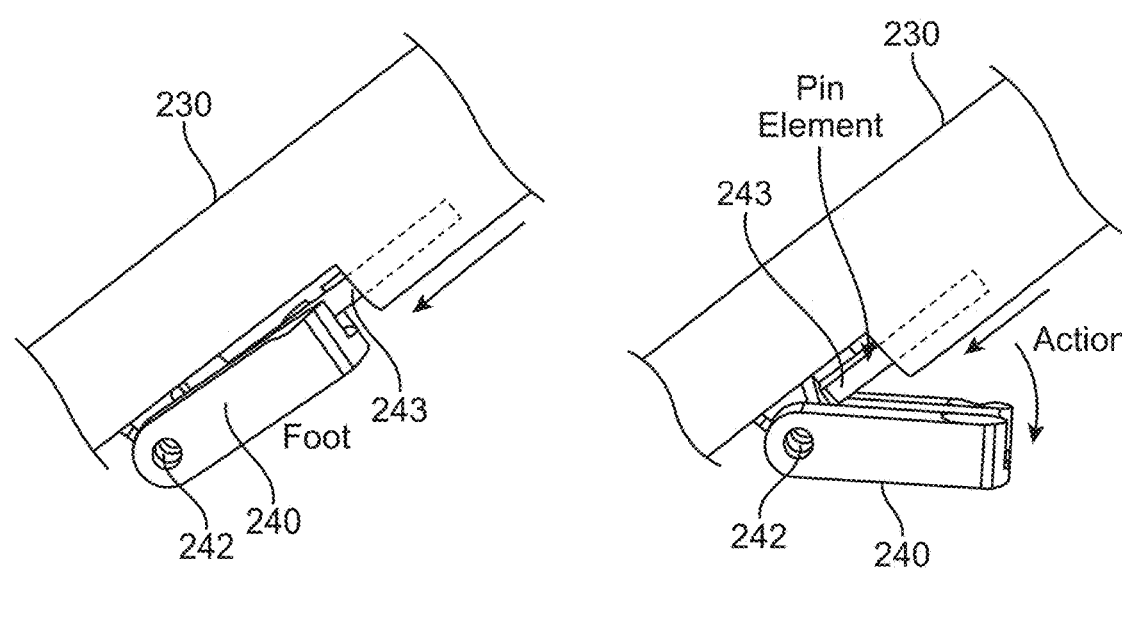
FIG. 37A
FIG. 37B

TISSUE CLOSURE SYSTEMS

CROSS-REFERENCE TO RELATED APPLICATIONS

This application claims the benefit of priority to U.S. Prov. 63/495,454 filed Apr. 11, 2023, which is incorporated herein by reference in its entirety.

FIELD OF THE INVENTION

The present invention relates to methods and apparatus for closing a region of tissue. More particularly, the present invention relates to methods and apparatus for percutaneously closing an opening along a vessel wall such as an artery or vein.

BACKGROUND OF THE INVENTION

Upon the completion of a percutaneous procedure which utilize vascular access, the instruments such as an introducer sheath or steerable guide are removed from the vessel leaving the puncture site open. Various devices and methods have been employed to close the vessel opening to achieve hemostasis, including compression, plugs, patches, metal clasps, and suture-applying devices which are used to deploy suture on opposing sides of a puncture which is then tightened to approximate the edges of the puncture site. Suture based devices are preferred in the market largely because the edges of the opening are closed in a manner most similar to an open surgical technique.

While such devices can be used effectively, they are limited by the size of the puncture site and may require multiple instruments or be placed before the percutaneous procedure to effect closure. For instance, a puncture site which is relatively large may require the use of two instruments in which a first device is deployed and removed and then a second device is deployed and removed yet again to achieve hemostasis of the puncture site. Alternatively, the suture(s) may need to be placed while the puncture site is small, using a "pre-close" technique, where the suture(s) are placed prior to the expansion of the opening necessary for the introducer sheath and percutaneous procedure. Then following the completion of the procedure, and removal of the sheath, the suture(s) are tightened and secured with knot(s) or other means. In many instances the percutaneous procedure is an emergency, such as an aortic aneurysm, and there is no time to place the suture prior and the use of multiple devices is a further hinderance. Furthermore, there is also increased risk of damage or bacterial contamination of the suture that remains outside the patient during the percutaneous procedure increasing the infection risk following the procedure. This risk may lead to the choice of a monofilament suture with a given design which has reduced surface area over a braided suture but less robust performance or added complexities as a result.

Additionally, such devices are initially introduced into and through the puncture site and are then advanced partially into the vessel to be closed. A mechanism is then typically deployed within the interior of the vessel for facilitating placement of a suture into the tissue surrounding the opening. However, introduction of the device into the vessel as well as deployment of the mechanism may be hindered depending upon the size of the vessel and relative size of the device.

Furthermore, such devices may employ pre-tied knots which are delivered through the device for closing and securing the puncture sites. Yet the employment and delivery of pretied knots may complicate the delivery of suture into and through the tissue and further provides limited flexibility in tissue securement. Knots also contain large surface areas, which if utilized in a pre-close method increase the risk of bacterial contamination and infection following the procedure. Alternatively, such devices may employ separate devices or the physician to tie the knots, delaying the tissue securement.

Accordingly, devices and methods for percutaneously closing large puncture sites along vessel walls are desired where sutures may be deployed into the tissue using a single device and without pre-close, which simplifies the procedure. Furthermore, such devices and methods are desired to minimize the risk of suture damage or bacterial contamination associated infections. Furthermore, such devices and methods are desired which facilitate the puncture closure despite the vessel size and which also utilizes a simplified closure mechanism to achieve hemostasis. For the above reasons, it would be desirable to provide improved devices, systems, and methods for suture-based tissue closure. It would be particularly beneficial if these improved devices and methods provided some or all of the benefits while overcoming one or more of the disadvantages discussed above.

SUMMARY OF THE INVENTION

One variation of a device designed to close openings within a tissue wall such as an arteriotomy or venotomy along a vessel wall may include an elongate catheter having a distal catheter segment and a proximal catheter segment which are configured to move or rotate relative to one another. The device may include a handle configured to be held (e.g., via a single hand) by a practitioner. A first actuation mechanism such as a lever, slide, or other mechanism may be incorporated along the handle for deploying a receiver member for receiving needle members for insertion through the tissue region to be closed. A second actuation mechanism such as a plunger or other mechanism may also be incorporated along the handle for pushing or activating movement of the needle members from the proximal catheter segment and into the tissue as well as pulling or tensioning the sutures through tissue and through the device handle. An indicator such as an open lumen or other flash indicator may also be incorporated into the handle where the open lumen may be in fluid communication through a lumen defined through the device and the proximal catheter segment for receiving an amount of blood which may provide a confirmatory indication that the device has been suitably introduced and positioned within a vessel to be closed. In other variations, other alternative sensors or sensor mechanisms may be used to provide the confirmatory indication that the device has been suitably positioned within the vessel, for example, sensors which utilize pressure, continuity, capacitance, temperature or heat, fiber optic, flow, etc. may be used. Marked graduations on the device shaft may be utilized to inform the user of the vessel depth which is useful when tightening and locking the sutures.

The proximal catheter segment may extend distally from the handle with a deployment segment joining a distal catheter segment which may further extend distally where the device may terminate with a conical distal tip which angles towards a relatively smaller distal end and may serve as a dilator for facilitating entry of the device into and through the anatomy including the tissue, arteriotomy or venotomy. The conical distal tip may incorporate one or more lumens at the tip or along the sides which allow for the passage of a guidewire, if desired.

The deployment segment may include a support structure which extends from the proximal catheter segment along two opposed members which define a receiving area between the two opposed members. The support structure may extend in a straightened configuration from the proximal catheter segment and may include a curved or arcuate portion which curves the structure at an angle relative to the proximal catheter segment. The distal catheter segment may extend from the support structure via a hinged or pivoting attachment which enables the distal catheter segment to rotate relative to the proximal catheter segment. In other embodiments, the support structure may be formed as flexible structure which is continuous such as a living hinge or otherwise a flexible segment. The receiving area defined by the two opposed members of the support structure is sized to house a receiver member which is rotatable from its low-profile delivery configuration to its deployed configuration. The receiver member may define two or more needle receiving openings for receiving the piercing tips of the needles which may deployed from corresponding openings along the distal portion of the proximal catheter segment.

Once the deployment segment has been suitably positioned relative to the vessel opening to be closed, the first actuation mechanism may be activated. The rotation of the receiver member may reposition a first receiver portion of the receiver member to receive the one or more distally extending forward needle members advanced distally from the openings and may further reposition a second receiver portion of the receiver member on a second opposite side of the support structure to receive one or more distally extending rear needle members advanced distally from openings along the second opposite side of the proximal catheter segment. Actuation of the second actuation mechanism may urge the advancement of the needle members distally from the proximal catheter segment.

These needle members (one or more forward and one or more rear needle members) may be configured to advance one or more suture loops from the inside diameter or inner wall of the vessel and within the vessel interior between each pair of needle members through the wall of the vessel to the vessel exterior. For two or more suture loops the loops may be parallel along the interior of the vessel and crossed on the exterior, or in yet another variation the suture loops may be crossed on the both the interior and exterior of the vessel. The resulting suture ends may be pulled or tensioned remote from the puncture site (e.g., from outside the patient body) to approximate the tissue edges of the puncture site without the need for any knots and a separate instrument may be used to deploy a securement device such as a cinch, ferrule, clip, etc., as described in further detail herein.

Because the proximal catheter segment is angled relative to the tissue wall or vessel axis at the puncture site after insertion and placement, the perimeter of the device transition area forms more of an oval or elliptical shape relative to the tissue wall. The perimeter represents the area of the angled proximal catheter segment relative to the tissue wall at the puncture site. With the reduction of the width of the perimeter along the longitudinal direction of the vessel length, the device profile and perimeter may expand in the transverse direction.

As the projected perimeter forms an oval or elliptical shape, the edges of the puncture site may also be relatively closer to the outer surface of the angled proximal catheter segment and the oval or elliptical perimeter may hence enable the catheter segment to be used to facilitate the closure of the puncture site.

As the device may be used to approximate tissue openings such as arteriotomies or venotomies, two or more separate lengths of suture which are independent of one another may be preloaded within the device and used with the needle members to deliver suture through the vessel walls to approximate the tissue edges for hemostasis. This may be accomplished without the need of any pre-tied knots. Due to the lengths of the suture, the suture may be stored and deployed into the tissue using a number of different suture management variations.

In one variation, the suture may be pre-loaded within a lumen or space defined within the length of the proximal catheter segment while in another variation, the suture may be pre-loaded within a lumen or space defined within the length of the distal catheter segment. In yet another variation, the suture length may be stored within the proximal catheter segment and may further pass distally back through a lumen within the distal catheter segment.

In one variation the suture lengths are protected from tissue exposure during insertion of the device within the proximal or distal catheter sections and may be further protected by use of a slideable sleeve, sheath or other means. The slidable sleeve may incorporate a proximal interface member which is larger than the opening in the skin and may be used to improve hemostasis in and around the proximal catheter segment.

In one variation, the suture lengths may be deployed into the tissue resulting in a cross-stitch pattern which may result under or over the puncture site along the vessel. In another variation, the suture lengths may be deployed into the tissue resulting in a parallel stitch pattern which may result under or over the puncture site along the vessel.

As described herein, the tissue surrounding the puncture site may be configured into an oval or elliptical configuration to increase the bite margin along the tissue between the needle members and the catheter exterior. While the puncture site may be configured by the angling of the device relative to the vessel, additional features may be optionally incorporated to further increase or facilitate the tissue reconfiguration, particularly for puncture sites which may be particularly large relative to the device transition diameter.

One or more lateral dilation elements may be configured to extend from the exterior of the proximal catheter segment and/or distal catheter segment and/or support structure as well in order to force the edges of the puncture site along the sides of the device away from one another such that the edges of the puncture site forward and rear of the device along the vessel are urged towards one another. These lateral dilation elements may be configured to extend when actuated by a mechanism located, for example, upon the handle.

As described herein, the device may be sized and used to place suture loops for approximation of tissue openings such as arteriotomies or venotomies without the need to place the sutures prior to the expansion of the opening with the procedural sheath or guide catheter, commonly referred to as the "pre-close" technique.

As described herein, a second instrument for suture capture and securement may be used to secure the ends of each suture length after deployment and delivery through the tissue region to be closed for hemostasis following the use of the devices described above.

One variation of a suture capture and securement device may include a handle having an actuation mechanism for deploying or securing an anchor to the captured sutures. An elongate shaft may extend from the handle and terminate in an opening at its distal tip. The opening may extend partially through the shaft and to a window which is defined along a side of the shaft in proximity to the distal tip. A securement anchor such as a ferrule having a lumen therethrough may be positioned within the opening. A slide element may be detachably positioned along the shaft or along the handle and a wire may be coupled to the slide element and extend along the device and pass into the window, through the securement anchor, and distally through the opening where the wire may form a snare loop which opens into an expanded loop.

In use, the terminal suture ends which remain after the delivery of the suture around the puncture site may each be passed through the snare loop. The slide element may be pulled proximally along the elongate shaft such that the wire is pulled through the window and securement anchor such that the snare loop tightens around the suture ends. As the slide element is pulled further proximally, it may abut the tapered interface surface defined along the distal end of the handle such that the slide element is directed off axis and disengaged away from the elongate shaft. As the snare loop is further pulled proximally through the securement anchor and window, the ensnared suture ends may be pulled through accordingly until the suture ends pass entirely through both the securement anchor and window.

The suture ends may be tensioned proximally as the distal tip of the shaft is pushed distally while tightening the sutures engaged through the tissue until the puncture site is closed. Such manipulation of the device and suture lengths may allow for an assessment of hemostasis prior to securement of the anchor component. Alternately, marked graduations on the elongate shaft, which correspond to those on the suture delivery device shaft, may be utilized to inform the user of the vessel depth. Once hemostasis and/or proper depth has been assessed, the securement anchor may be deformed, crimped, or otherwise tightened to secure the suture passing through until movement of the securement anchor is no longer possible. This deformation may be sufficient to simultaneously cut or terminate the suture ends without the need for a separate cutting mechanism. Alternatively, with the securement anchor crimped or tightened, the suture ends may be simultaneously, or otherwise, cut or trimmed and the shaft may be removed leaving the securement anchor and trimmed suture with hemostasis achieved.

As the suture capture and securement device omits the need for any knots or any pre-tied knots, the securement anchor which tightens upon the suture ends and secures the tensioned suture upon the tissue for hemostasis may include any number of deployable ferrules, clips, etc. One particular variation of a securement anchor which may be deployed from the distal opening of the device shaft may include a ferrule which can be sized in any number of configurations depending upon the use case. The ferrule may be sized to capture the suture ends for complete closure and such ferrule structures may be fabricated from any number of materials such as metals which may be deformed (e.g., compressed, crimped, etc.) upon the sutures or polymers which may be heat melted upon the suture for securement. In the event that the sutures used are polymeric, the ferrule may be partially melted along with a portion of the sutures to effect a secure anchor.

One variation of a tissue closure apparatus may generally comprise a handle having one or more actuation mechanisms, a proximal catheter segment extending from the handle, a deployment segment coupled to the proximal catheter segment, a distal catheter segment pivotably coupled to the deployment segment such that the distal catheter segment is rotatable relative to the proximal catheter segment, a receiver member positioned within the deployment segment and having two or more openings along a first receiver portion and two or more openings along a second receiver portion, wherein the receiver member is configurable between a low-profile configuration and a deployed configuration, and two or more forward needle members which are extendable distally from a first side of the proximal catheter segment and two or more rear needle members which are extendable distally from a second side of the proximal catheter segment opposite to the first side. The two or more forward needle members are receivable into the two or more openings along the first receiver portion and the two or more rear needle members are receivable into the two or more openings along the second receiver portion when the receiver member is in the deployed configuration.

One variation of a method for tissue closure may generally comprise advancing a distal catheter segment into and through an opening along a wall of a vessel such that the distal catheter segment rotates about a deployment segment and the distal catheter segment is angled relative to a proximal catheter segment, deploying a receiver member from a low-profile configuration to a deployed configuration within the vessel such that a first receiver portion and a second receiver portion are contacted against the wall adjacent to the opening, distally extending two or more forward needle members from a first side of the proximal catheter segment and two or more rear needle members from a second side of the proximal catheter segment opposite to the first side such that each of the needle members are pierced through the wall adjacent to the opening, and receiving the two or more forward needle members into two or more openings along the first receiver portion and the two or more rear needle members into two or more openings along the second receiver portion.

One variation of a method for minimizing an infection risk associated with tissue closure may generally comprise advancing a suture delivery catheter into and through an opening along a wall of a vessel such that the distal catheter segment rotates about a deployment segment and the distal catheter segment is angled relative to a proximal catheter segment, deploying a receiver member from a low-profile configuration to a deployed configuration within the vessel such that a first receiver portion and a second receiver portion are contacted against the wall adjacent to the opening, distally extending two or more forward needle members from a first side of the proximal catheter segment and two or more rear needle members from a second side of the proximal catheter segment opposite to the first side such that each of the needle members are pierced through the wall adjacent to the opening, and receiving the two or more forward needle members into two or more openings along the first receiver portion and the two or more rear needle members into two or more openings along the second receiver portion such that the two or more forward needle members are received into a corresponding coupling member retained within each of the two or more openings along the first receiver portion and the two or more rear needle members are received into a corresponding coupling member retained within each of the two or more openings along the second receiver portion, retracting the two or more forward needle members from the first receiver portion and the two or more rear needle members from the second receiver portion such that a first suture length and a second suture length are retracted proximally through the wall adjacent to the opening, and securing the first suture length and the second suture length with a tissue securement anchor which prevents movement of each of the suture lengths without the use of knots.

One variation of a suture anchor device may generally comprise a handle having an actuation mechanism, a shaft attached to the handle, wherein the shaft has a distal tip which defines a distal opening and a window along a side of the shaft such that the distal opening and window are in communication, a slide element translatably positioned upon the shaft, a tissue securement anchor positioned within the distal opening and defining an anchor lumen which is in communication with the window, and a wire connected to a distal portion of the slide element and extending into the window and through the anchor lumen such that the wire exits the distal opening and forms a snare loop.

One variation of a method for anchoring suture may generally comprise positioning one or more lengths of suture within a snare loop extending from a distal opening of a shaft, proximally retracting a slide element along the shaft such that the snare loop reduces in size and pulls the one or more lengths of suture proximally into the distal opening, through an anchor lumen of a tissue securement anchor positioned within the distal opening, and out through a window defined along a side of the shaft, positioning the distal opening of the shaft in proximity to a tissue opening along a vessel wall while tensioning the one or more lengths of suture, and deforming the tissue securement anchor such that the one or more lengths of suture are secured.

BRIEF DESCRIPTION OF THE DRAWINGS

FIGS. 30A and 30B show top and cross-sectional top views of another variation of the distal catheter segment having one or more friction inducing features incorporated along the segment for imparting a frictional grip or resistance upon the suture.

FIGS. 31A to 31C show various cross-sectional shapes of the tensioning members.

FIG. 33A schematically illustrates an example where a push/pull member may incorporate an expansion member attached along the push/pull member.

FIGS. 33B-33D show variations of dilation arms which are positioned on opposite sides of one another along the distal end of the proximal catheter segment.

FIGS. 36A and 36B show perspective views of yet another variation of the device incorporating a central shaft having a ramp portion.

FIGS. 37A and 37B show perspective views of the second receiver portion corresponding to FIGS. 36A and 36B.

DETAILED DESCRIPTION OF THE INVENTION

A device which is designed to close openings within a tissue wall such as an arteriotomy or venotomy along a vessel wall may include an elongate catheter having a distal catheter segment and a proximal catheter segment which are configured to move or rotate relative to one another. Either the distal and/or proximal catheter segments may be utilized to deploy several retractable needles which can be used to capture and/or tighten segments of a suture length for closing the arteriotomy or venotomy.

Figures 1A, 1B:
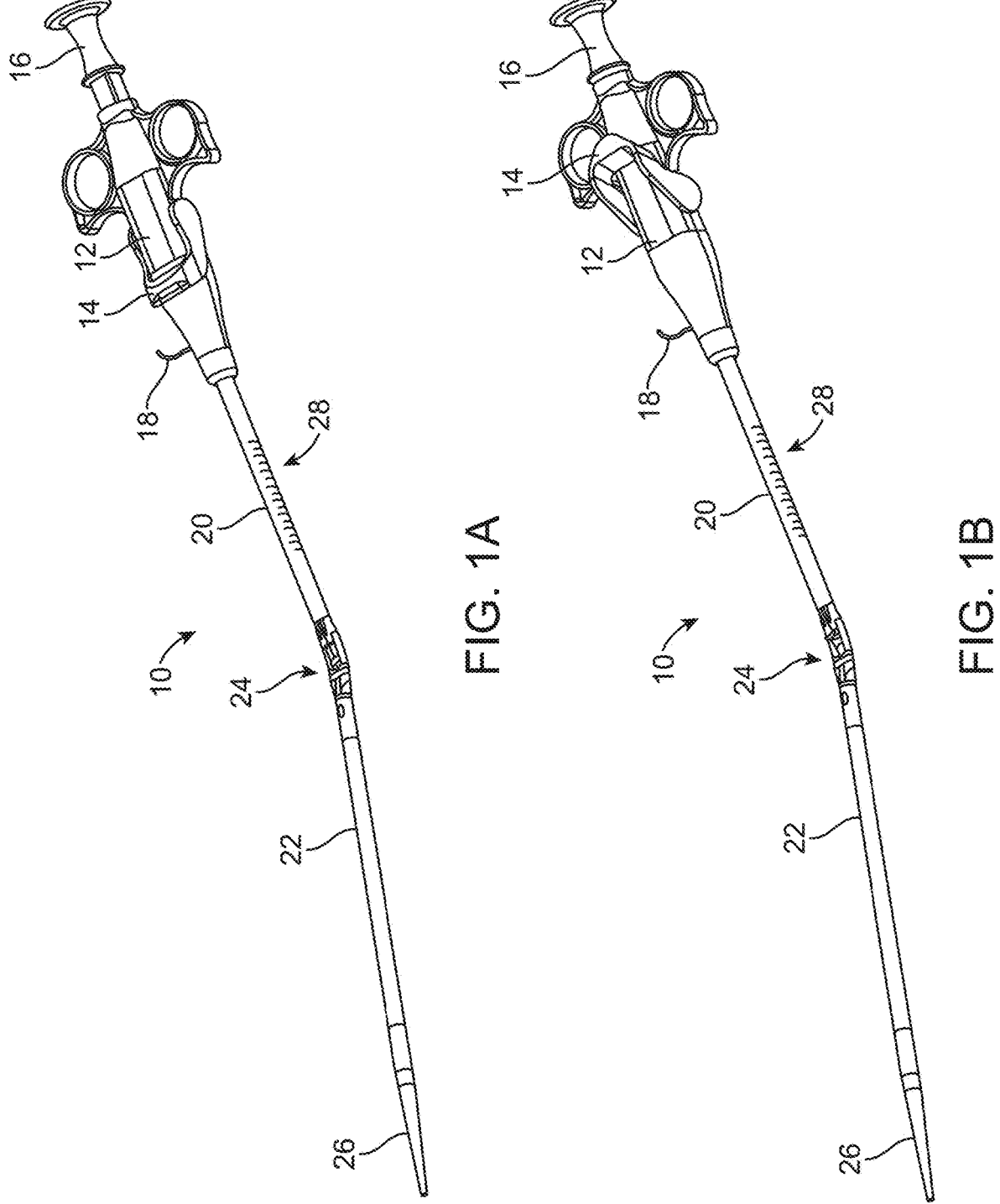
FIGS. 1A and 1B show perspective views of one variation of a device for actuating needle deployment for delivering and/or capturing suture lengths in closing an opening in tissue.

One variation of such a device is shown in the perspective views of FIGS. 1A and 1B which illustrate one example for actuating the needle deployment for delivering and/or capturing suture lengths. FIG. 1A shows the device 10 having a handle 12 configured to be held (e.g., via a single hand) by a practitioner. A first actuation mechanism 14 such as a lever, slide, or other mechanism may be incorporated along the handle 12 for deploying a receiver member for receiving needle members for insertion through the tissue region to be closed. A second actuation mechanism 16 such as a plunger 16 or other mechanism may also be incorporated along the handle 12 for pushing or activating movement of the needle members from the proximal catheter segment 20 and into the tissue as well as pulling or tensioning the sutures through tissue and through the device handle 12, as described in further detail herein. An indicator 18 such as an open lumen 18 or other flash indicator may also be incorporated into the handle 12 where the open lumen 18 may be in fluid communication through a lumen defined through the device and the proximal catheter segment 20 for receiving an amount of blood which may provide a confirmatory indication that the device has been suitably introduced and positioned within a vessel to be closed. Furthermore, marked graduations 28 along the proximal catheter segment 20, distal catheter segment 22, and/or both segments 20, 22 may be provided, as shown, to inform the user of the depth beneath the surface of the skin where the vessel is located which may be useful when tightening and locking the sutures. The graduations 28 may be marked as the distance relative to the receiver member. Once deployed within the vessel, the receiver member is already positioned within the vessel along the tissue wall adjacent to the opening and hence provides a datum from which the graduations 28 may be marked in order to provide the depth of the vessel from the skin surface.

The proximal catheter segment 20 may extend distally from the handle 12 with a deployment segment 24 joining a distal catheter segment 22 which may further extend distally where the device may terminate with a conical distal tip 26 which angles towards a relatively smaller distal end and may serve as a dilator for facilitating entry of the device into and through the arteriotomy or venotomy. The conical distal tip 26 may incorporate one or more lumens at the tip or along the sides which allow for the passage of a guidewire, if desired.

FIG. 1B illustrates the device with both the first actuation mechanism 14 pulled or otherwise activated and the second actuation mechanism 16 advanced or pushed relative to the handle 12 to deploy the needles and the rotating receiver platform positioned along the deployment segment 24.

Receiver and Needle Deployment

Figures 2A, 2B:
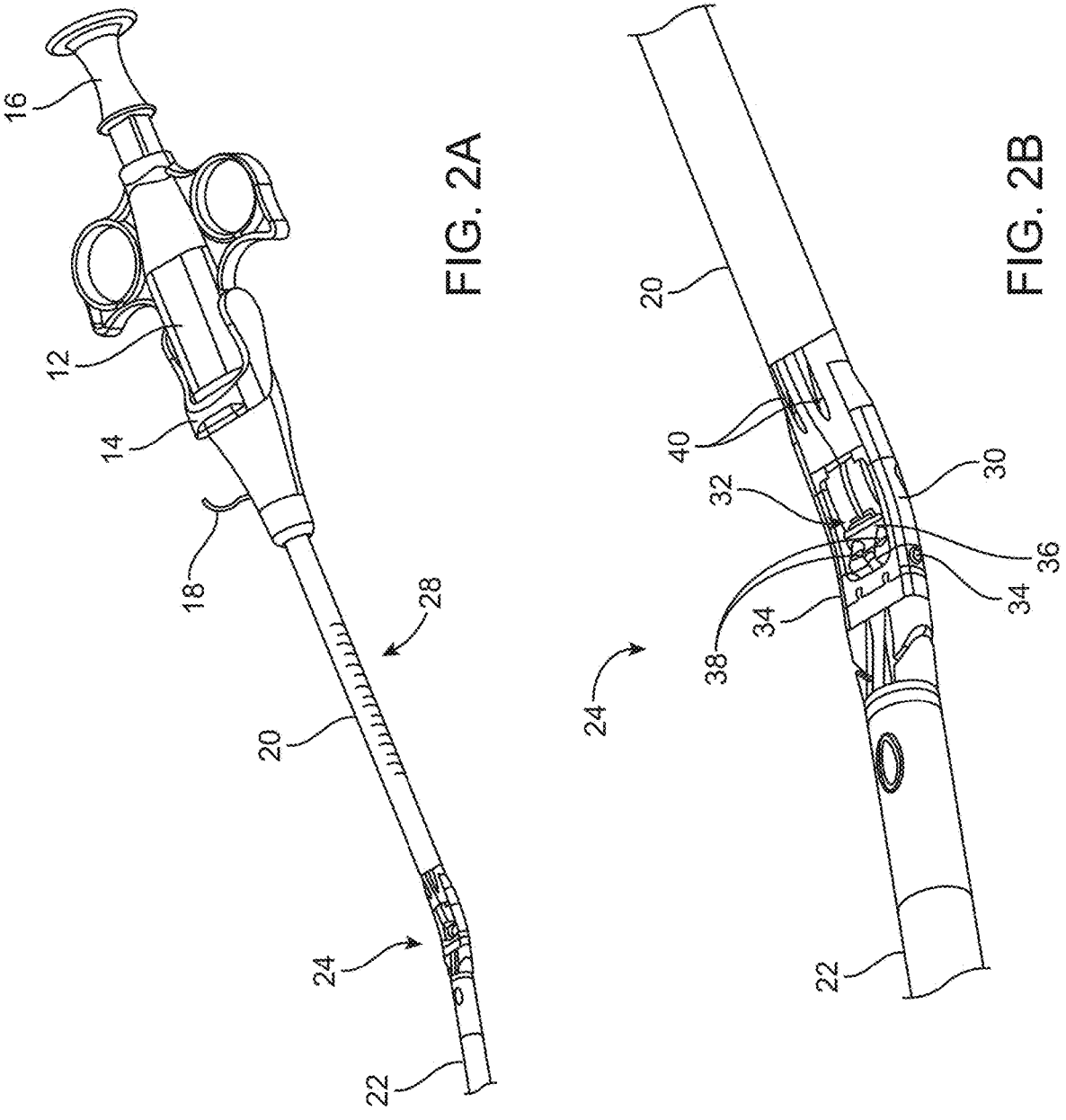
FIGS. 2A and 2B show perspective detail views of a first actuation mechanism on a handle in its unactuated configuration and the corresponding deployment segment maintained in its low-profile delivery configuration.

FIG. 2A shows a detail view of the first actuation mechanism 14 on handle 12 in its unactuated configuration and the deployment segment 24 in FIG. 2B illustrating how the deployment segment 24 is maintained in its low-profile delivery configuration. The deployment segment 24 may include a support structure 30 which extends from the proximal catheter segment 20 along two opposed members which define a receiving area 32 between the two opposed members. The support structure 30 may extend in a straightened configuration from the proximal catheter segment 20 and may include a curved or arcuate portion which curves the structure 30 at an angle relative to the proximal catheter segment 20, as further described herein. The distal catheter segment 22 may extend from the support structure 30 via a hinged or pivoting or flexible attachment 34 which enables the distal catheter segment 22 to rotate readily about a predefined angle of rotation relative to the proximal catheter segment 20. The receiving area 32 defined by the two opposed members of the support structure 30 is sized to receive a receiver member 36 which is rotatable from its low-profile delivery configuration, as shown in FIG. 2B, to its deployed configuration, as described below. The distal portion of the receiver member 36 may define two or more needle receiving openings 38 for receiving the distal piercing tips of the needles which may deployed from corresponding openings 40 along the distal portion of the proximal catheter segment 20.

Figures 2C, 2D:
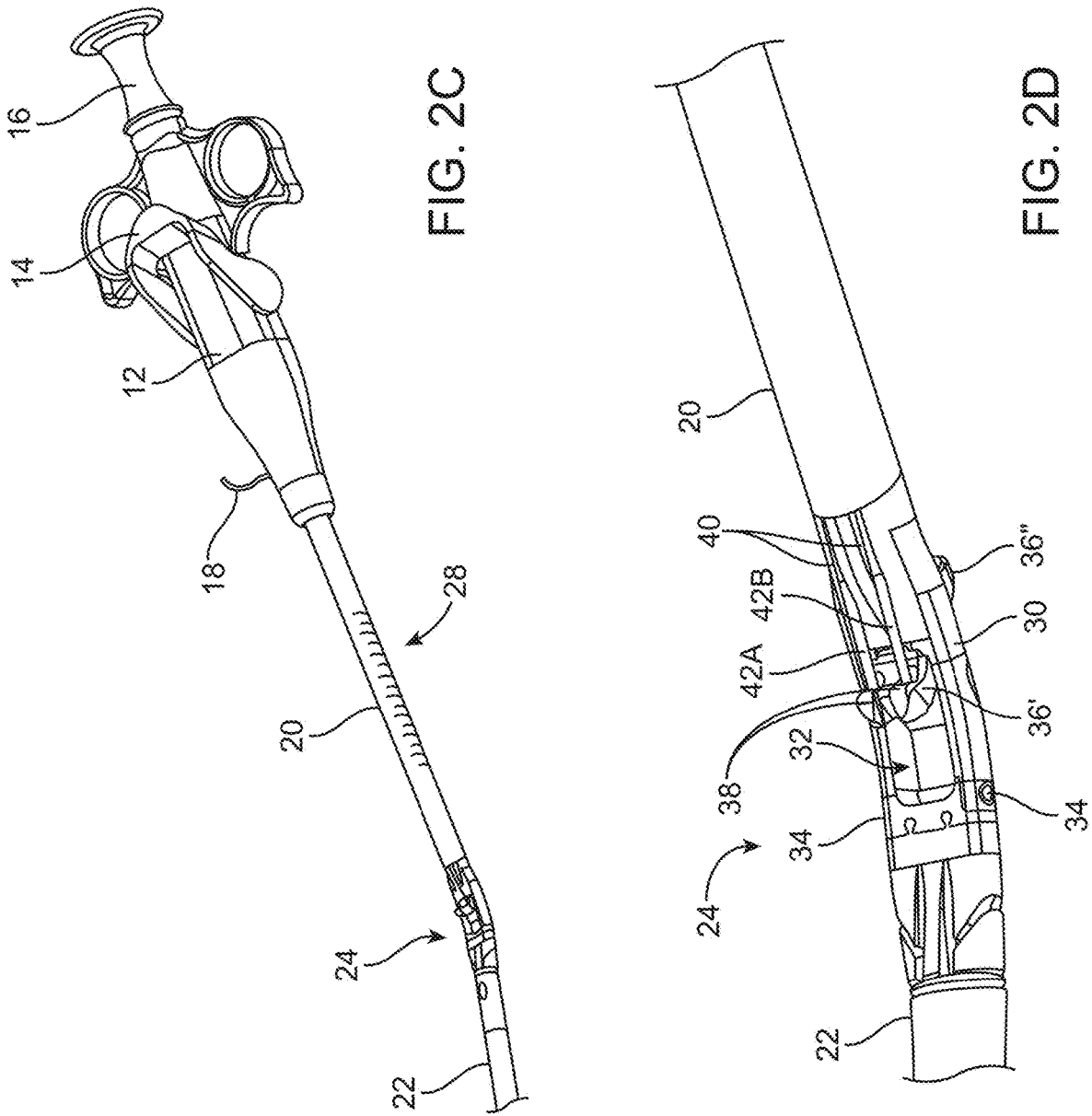
FIGS. 2C and 2D show perspective detail views of the first actuation mechanism on the handle in its actuated configuration and the corresponding deployment segment in its deployed configuration.

Once the deployment segment 24 has been suitably positioned relative to the vessel opening to be closed, the first actuation mechanism 14 may be activated, as shown in the example of FIG. 2C where the mechanism 14 may be pulled to rotate about the handle 12 in order to reconfigure the receiver member 36 from its low-profile delivery configuration into its deployed configuration where the receiver member 36 may rotate between the two opposed members at an angle relative to the support structure 30. The rotation of the receiver member 36 may reposition a first receiver portion 36' of the receiver member to receive the two distally extending forward needle members 42A, 42B advanced distally from the openings 40 and may further reposition a second receiver portion 36" of the receiver member on a second opposite side of the support structure 30 to receive two distally extending rear needle members (hidden in this illustration) advanced distally from openings along the second opposite side of the proximal catheter segment 20. Actuation of the second actuation mechanism 16 may urge the advancement of the needle members distally from the proximal catheter segment 20 into the receiver member receiver locations 36, as shown.

In this variation, the device 10 is shown to have two forward needle members deployable along a first side of the proximal catheter segment 20 and two rear needle members deployable along a second side of the proximal catheter segment 20 opposite to the first side for a total of four needle members. These four needle members may be configured to advance two suture loops between two needle members (e.g., between two adjacent needle members along the first side, two opposed needle members between the first side and the second side, and/or two opposed needle members which form a crossed or angled configuration, etc.). The resulting suture ends may be proximally pulled or tensioned remote from the puncture site (e.g., from outside the patient body) to facilitate approximation the tissue edges of the puncture site without the need for knots and a separate instrument may be used to deploy a securement device such as a cinch, ferrule, clip, etc., as described in further detail herein.

In other variations, devices which use more than two needle members on either or both sides of the device 10 may be utilized. Alternatively, other variations may include devices that have more needle members on one side than on the second opposite side depending upon the desired closure of the tissue opening.

With the use of two suture loops, the clinical outcome of the closed tissue region may be improved as both loops may function to approximate the tissue edges and improve hemostasis overall. Furthermore, the device 10 may be scaled to accommodate various size tissue puncture diameters to achieve tissue closure and/or various sized devices may be provided for closing different tissue puncture diameters. For example, a first sized device may be provided to close puncture diameters ranging from, e.g., 10-18 Fr, and a second sized device which is relatively larger in size may be provided to close puncture diameters ranging from, e.g., 18-30 Fr, and so on. Accordingly, the diameter of the distal catheter segment may range anywhere from, e.g., 14-24 Fr such as 20 Fr, while the diameter of the proximal catheter segment may range anywhere from, e.g., 10-30 Fr.

Figure 3A:
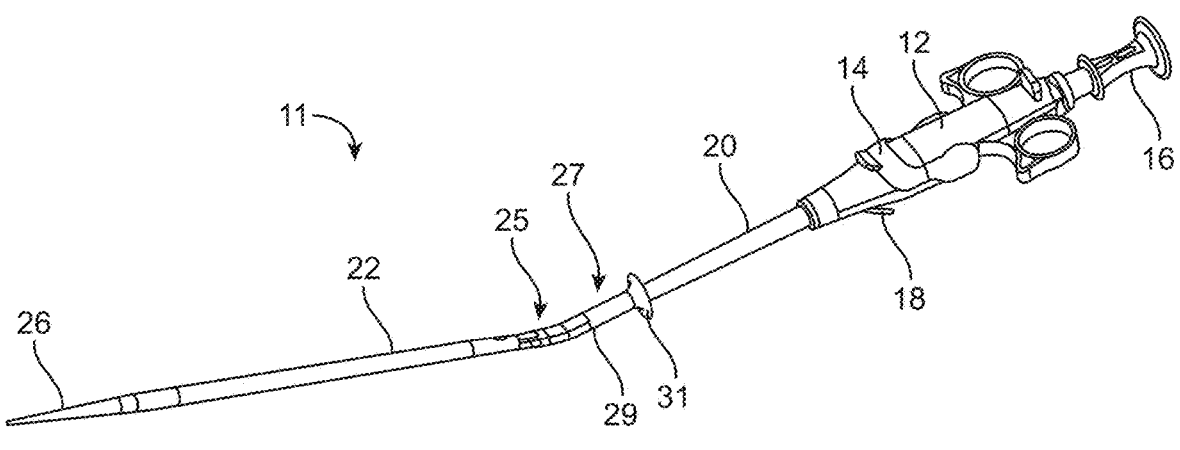
FIGS. 3A-3C show perspective views of another variation of the device for actuating needle deployment for delivering and/or capturing suture lengths in closing an opening in tissue.
Figure 3B:
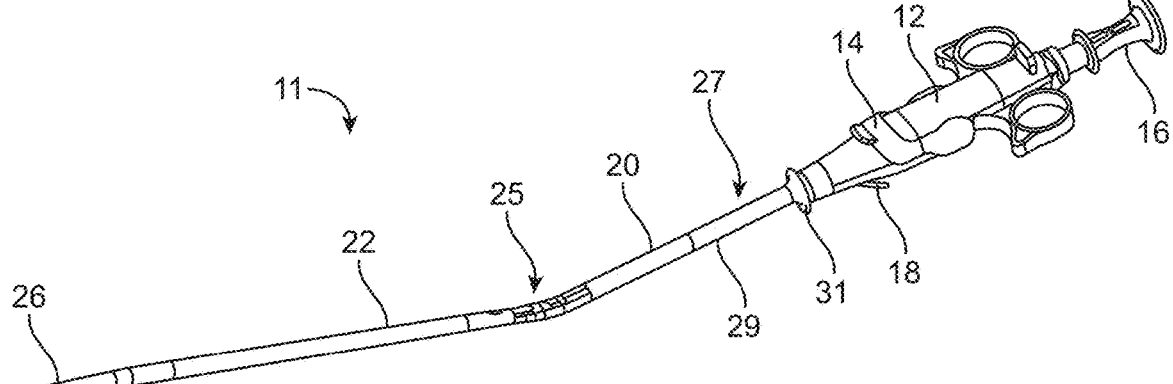
Figure 3C:
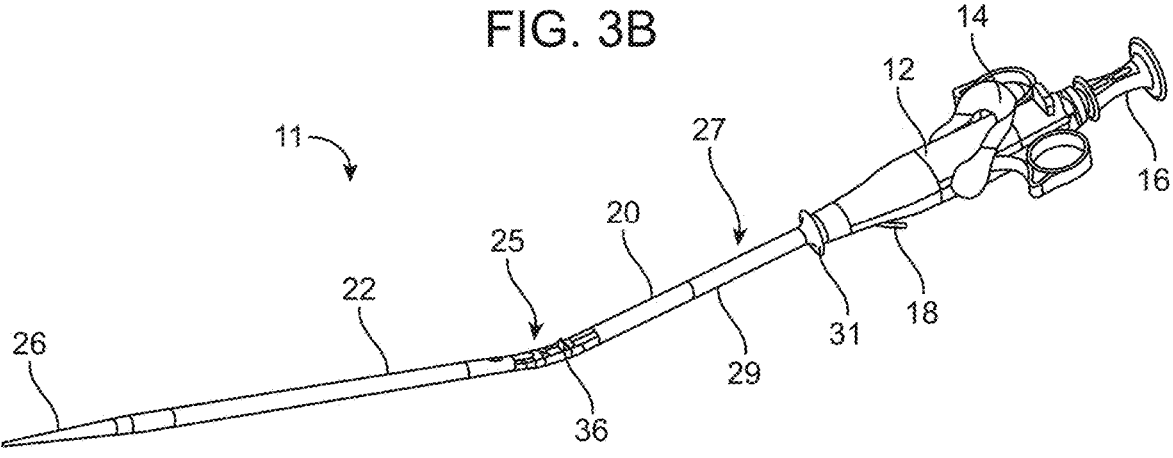

Another variation of the device 11 is shown in the perspective views of FIGS. 3A-3C which illustrate an embodiment which is similar to that described above but includes a deployment segment 25 which is configured to be continuous and flexible along its length. This deployment segment 25 may enable the distal catheter segment 22 to bend or flex relative to the proximal catheter segment 20 during insertion into the vessel without the need for a separate hinge or pivot mechanism.

Additionally, a sheath assembly 27 may be slidably positioned along the proximal catheter segment 20, as shown, where the sheath assembly 27 may have a sheath member 29 and a proximal interface member 31 attached to a proximal portion of the sheath member 29. The sheath member 29 may have a minimal thickness profile which allows for the sheath member 29 to be slid over the deployment segment 25 and suture lengths, as shown in FIG. 3A, during introduction and delivery into the patient body to protect the sutures by preventing any dislodgement of the sutures and preventing contact with skin or tissue which may heighten infection risk. The sheath member 29 may also present a smooth, low profile, outer surface to ensure that the deployment segment 25 and sutures can be introduced into the vessel without damaging any surrounding tissue while ensuring the leading edge of the sheath member 29 remains unobtrusive.

The proximal interface member 31 may be attached to a proximal end of the sheath member 29 and may be configured to facilitate retraction or advancement of the sheath member 29, as shown in FIG. 3B, either by the user, e.g., using two or more fingers with a single hand, or by the sheath member 29 coming into contact against the tissue surface in which the sheath member 29 may be retracted by the surrounding tissue as the device 11 is further advanced into the vessel. Accordingly, sheath member 29 may have a length which is sized to cover the deployment segment 25 but is less than a length of the proximal catheter segment 20. The inner diameter of the sheath member 29 may accordingly be equivalent to or approximate a circumference of the proximal catheter segment 20, e.g., 10-30 Fr or 20 Fr in one embodiment. The sheath member 29 may be either heat formed to achieve a curved profile shape and/or the sheath member 29 may be formed in a straightened configuration and re-shaped by virtue of the sheath member 29 sliding along the proximal catheter segment 20 and deployment segment 25. The proximal interface member 31 may also be formed to present a curved or arcuate interface along its distal surface for atraumatic contact against the tissues. The proximal interface member 31 may also be sized larger than the opening in the skin and angled or otherwise shaped, e.g., spherically, to allow use with compression for improved hemostasis in and around the proximal catheter segment 20. The underside of the angled or shaped proximal interface member may also be configured with felt, pledgets, or other similar means to improve the hemostatic performance.

Once the device 11 has been introduced and desirably positioned within the vessel and the sheath assembly 27 has been appropriately retracted, the first actuation mechanism 14 incorporated along the handle 12 may be actuated for deploying the receiver member 36, as shown in FIG. 3C.

Figures 4A, 4B, 4C:
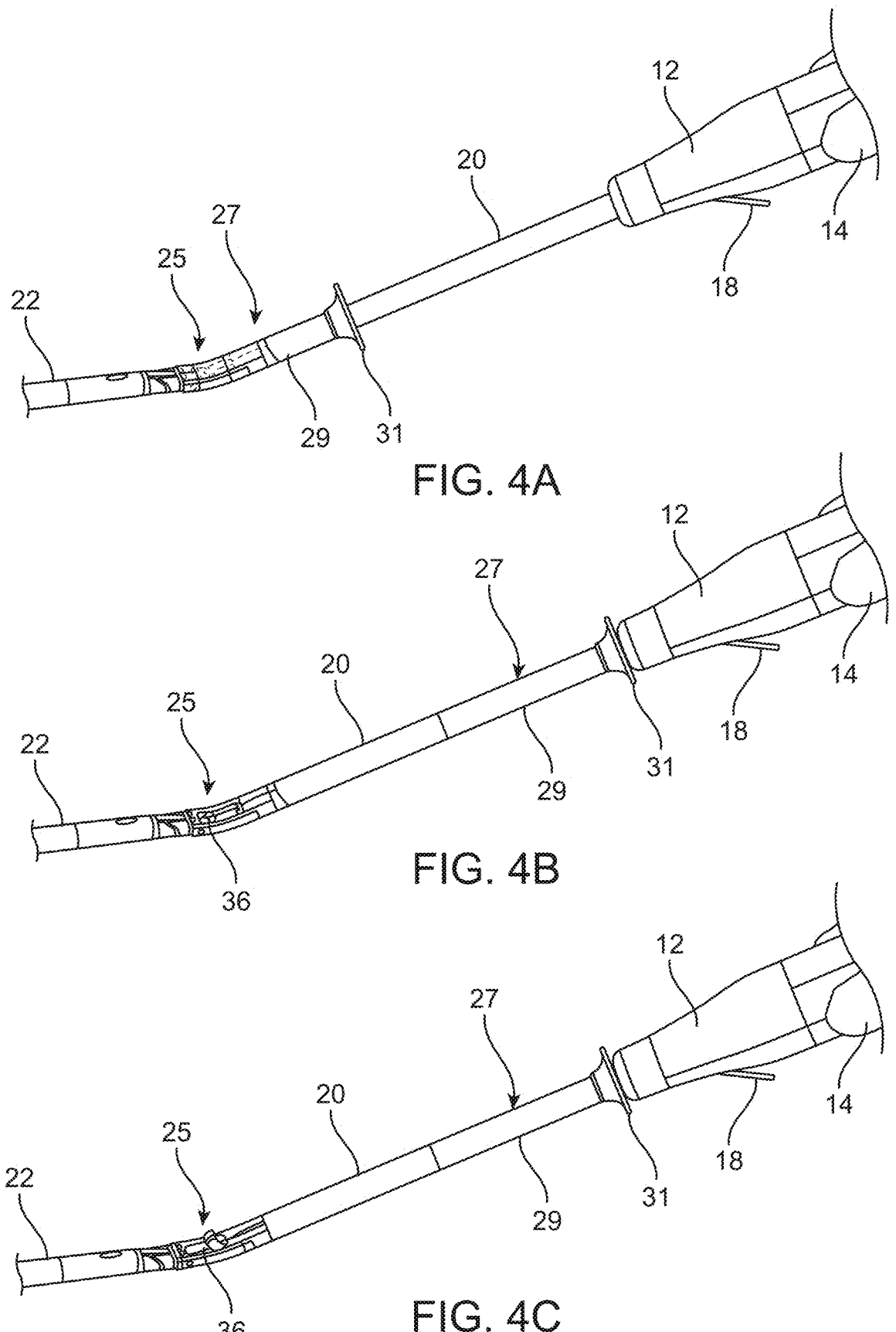
FIGS. 4A-4C show detail perspective views of the sheath assembly translated upon the proximal catheter segment and deployment segment corresponding to FIGS. 3A-3C.

FIGS. 4A-4C show detail perspective views of the sheath assembly 27 translated upon the proximal catheter segment 20 and deployment segment 25 corresponding to FIGS. 3A-3C described above. As shown in FIG. 4A, the sheath member 29 may be positioned so that the entire deployment segment 25 is covered by the sheath member 29. As shown in FIG. 4B, once the sheath assembly 27 is retracted proximally along proximal catheter segment 20, the entirety of the deployment segment 25 may become exposed by the sheath member 29. The sheath assembly 27 may be retracted proximally until the proximal interface member 31 abuts the handle 12. The receiver member 36 may also be exposed for deployment, as described herein and as shown in FIG. 4C.

Figure 5A:
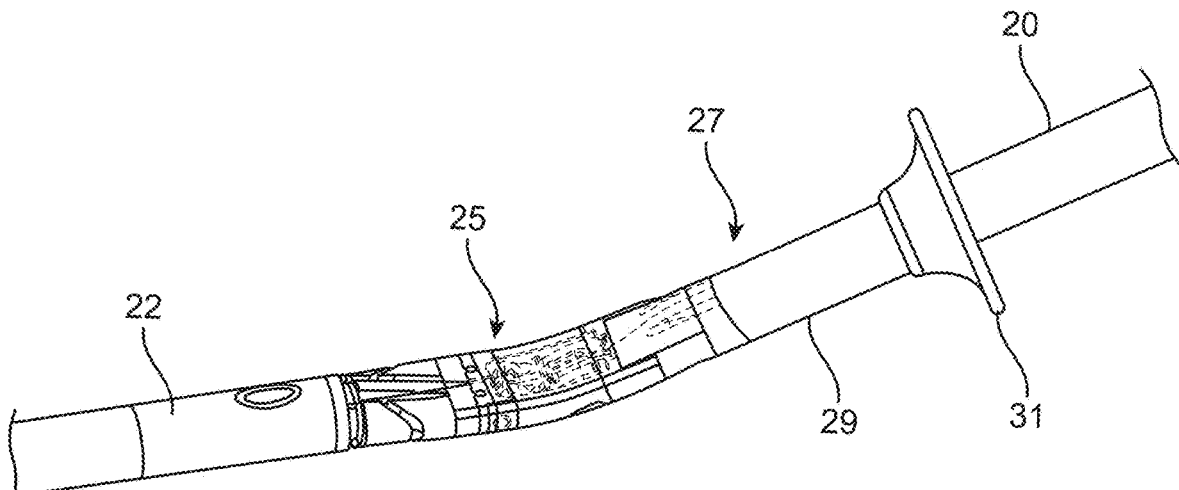
FIG. 5A shows a detail perspective view of the sheath member advanced distally over the deployment segment.

As shown in the detail perspective view of FIG. 5A, the deployment segment 25 is shown with the sheath member 29 advanced distally over the deployment segment 25. The leading edge of the sheath member 29 may be positioned to be just distal of the deployment segment 25 to guide the transition by, e.g., about 0.10 to 0.16 cm, to protect the sutures as they span from the distal portion of the device to the deployment locations affixed within the receiver member 36 without negatively impacting the flexibility of the deployment segment 25. Alternatively, the sheath member 29 may be extended fully over the entire exposed suture length such that the sheath member 29 may extend partially upon the distal catheter segment 22. In this location, the underlying sutures may be fully covered and protected from any external contact (such as contact with the skin surface) prior to retraction of the sheath member 29.

Figure 5B:
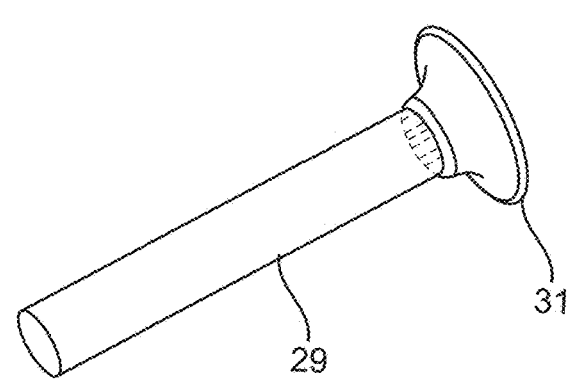
FIGS. 5B and 5C show side and end perspective views of the sheath member in an unconstrained configuration such as when the sheath assembly is retracted upon the proximal catheter segment.
Figure 5C:
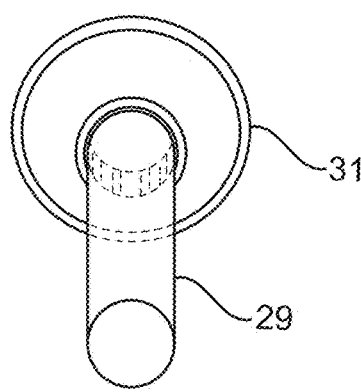
Figure 5D:
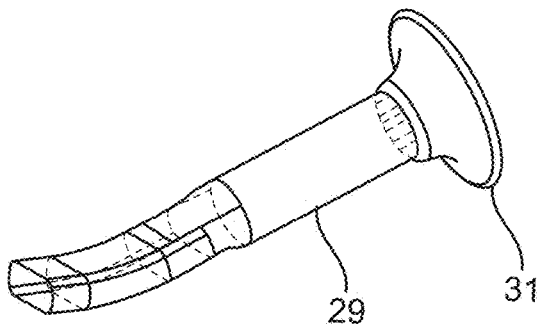
FIGS. 5D and 5E show the sheath member in its constrained configuration when the sheath member is positioned over the deployment segment and conformed to the underlying features.
Figure 5E:
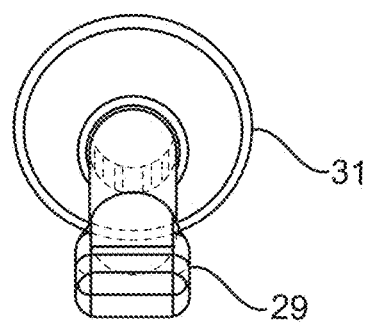

FIGS. 5B-5E show perspective side and front views of the sheath assembly 27 removed from the device 11. FIGS. 5B and 5C illustrate the sheath member 29 in an unconstrained configuration such as when the sheath assembly 27 is retracted upon the proximal catheter segment 20. FIGS. 5D and 5E illustrate the sheath member 29 in its constrained configuration when the sheath member 29 is positioned over the deployment segment 25 and conformed to the underlying features while encasing the receiver member 36 and undeployed sutures.

Figures 6A, 6B, 6C:
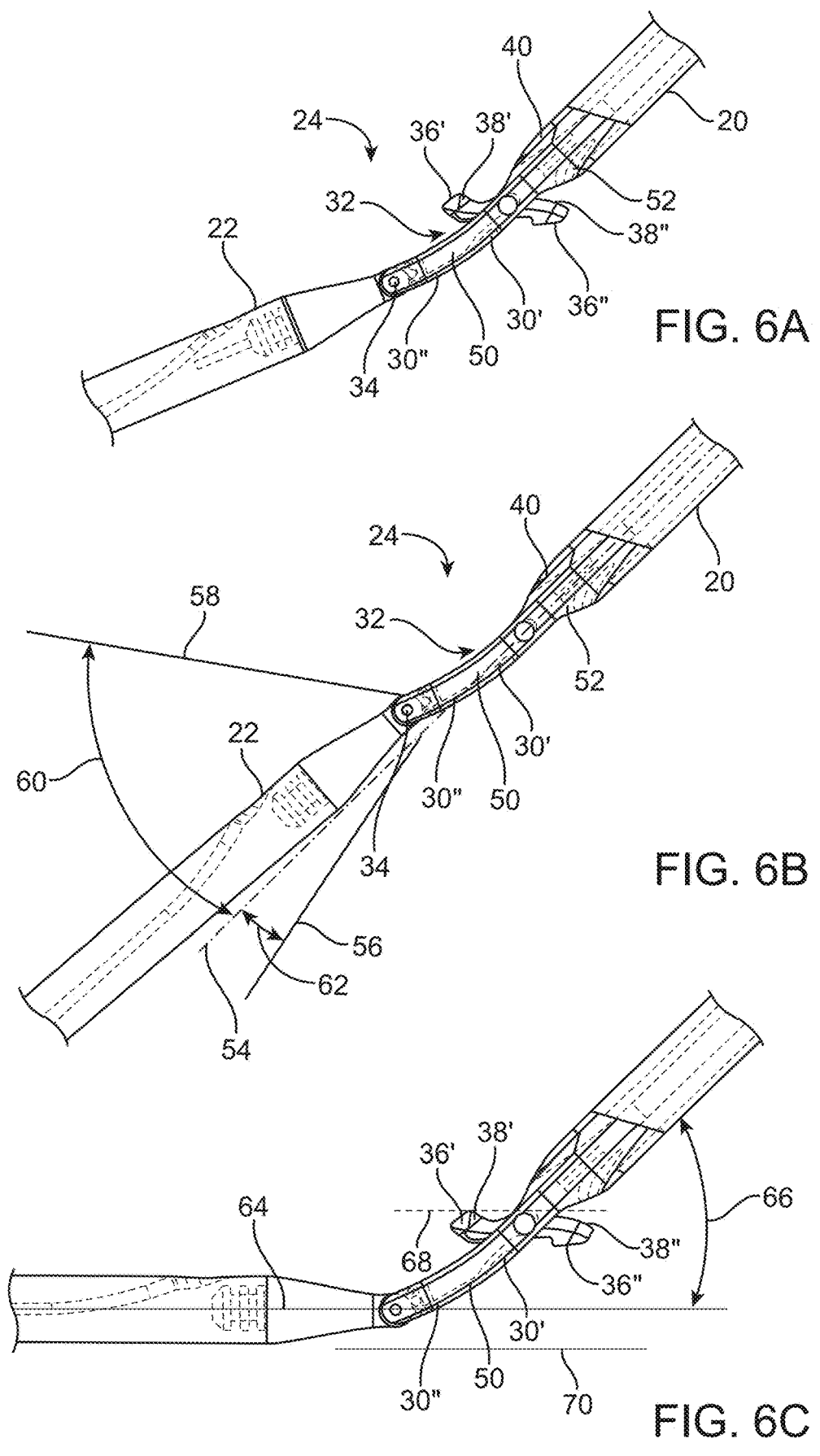
FIG. 6A shows a detail side view of the receiver member deployed from its low-profile configuration from within the support structure.
FIG. 6B shows a detail side view of the distal catheter segment pivotably or rotatably coupled to the proximal catheter segment in a non-collinear alignment relative to one another.
FIG. 6C shows a detail side view of the deployed receiver member relative to the distal catheter segment and the proximal catheter segment when positioned within a vessel lumen.

FIG. 6A illustrates a detail side view of how the receiver member 36 may be deployed from its low-profile configuration from within the support structure 30. As the receiver member 36 rotates, the first receiver portion 36' may rotate up and away from the support structure while the second receiver portion 36" may rotate down and away from the support structure until the first openings 38' defined along the first receiver portion 36' are aligned in a corresponding manner to receive the needle members advanced distally from the first openings 40 along a first side of the proximal catheter segment 20 and the second openings 38" defined along the second receiver portion 36" are aligned in a corresponding manner to receive the needle members advanced distally from the second openings 52 along a second side of the proximal catheter segment 20.

As previously mentioned, the support structure may extend distally along a proximal support structure 30' from the proximal catheter segment 20 in a straightened configuration and at intermediate portion 50 may be curved or arcuate along the support structure such that a distal portion of the support structure 30" may extend at a curved angle relative to the proximal catheter segment 20 such that the hinged or pivoting attachment 34 is out-of-plane relative to the proximal support structure 30' and the proximal catheter segment 20. The distal catheter segment 22 is pivotably or rotatably coupled to the hinged or pivoting attachment 34 such that when the distal catheter segment 22 is straightened, the distal catheter segment 22 and the proximal catheter segment 20 are not collinear with one another but instead may extend in parallel at a separation distance relative to one another, as shown in FIG. 6B. This offset between the longitudinal axis 54 of proximal catheter segment 20 and the longitudinal axis 64 of the distal catheter segment 22 may help to accommodate the receiver member 36 and may also help the distal catheter segment 22 to curve when initially introduced into the vessel and re-directed further into the vessel lumen while minimizing trauma to the tissue walls by decreasing the force applied against the tissue during cath- eter introduction and advancement through the puncture site. Additionally, and/or alternatively, portions of the device 10 such as the distal catheter segment 22, deployment segment 24, and/or proximal catheter segment 20 may be optionally treated for lubricity, e.g., with a hydrophilic coating or other lubricous additive(s).

As the hinged or pivoting attachment 34 facilitates the distal catheter segment 22 to curve for vessel introduction, the hinged or pivoting attachment 34 may allow for the rotation of the distal catheter segment 22 within a predeter- mined range of motion. The distal catheter segment 22 may rotate about the hinged or pivoting attachment 34 relative to the longitudinal axis 54 of the proximal catheter segment 20. For instance, distal catheter segment 22 may rotate at a positive angle 60 anywhere up to +55 degrees or more and may also rotate at a negative angle 62 anywhere up to −10 degrees or less. The range of motion may be varied by increasing or decreasing both or one of the angles to allow for usage flexibility without compromising device integrity and/or usability. In other embodiments, the support structure may be formed as flexible structure which is continuous such as a living hinge or otherwise a flexible segment.

As the distal catheter segment 22 is advanced through the puncture site and into the vessel, the rigidity of the compo- nents and their column strength may facilitate pushing the distal catheter segment 22 into the vessel while the offset axes may help the distal catheter segment 22 to gently push against the inner wall of the vessel. Once in position, the distal catheter segment 22 may be rotated relative to the proximal catheter segment 20 at an angle 66, e.g., around 45 degrees, as shown in the side view of FIG. 6C. To maintain the coupling of the proximal catheter segment 20 to the distal catheter segment 22, an internal flexible spine or coupling element may extend between the two segments through the support structure 30.

With the receiver member 36 deployed from its low- profile configuration into its deployed configuration within the vessel interior, as shown, the receiver member 36 may be ready to receive the needle members. However, to ensure that sufficient space is available within the vessel, the height of the deployed device may be adjusted. The height is represented as the distance between plane 68 (which repre- sents the top of the receiver member 36 when placed against the interior wall of the vessel) and plane 70 (which repre- sents the base of the angled distal catheter segment 22). Various features may accordingly be adjusted, e.g., the length of the support structure 30, angle of deployment between the proximal catheter segment 20 and distal cath- eter segment 22, the bottom of the interface of the distal catheter segment 22 may be reshaped, beveled, contoured, trimmed, etc. Accordingly, the height may range anywhere between, e.g., 5 and 20 mm, depending upon various factors such as the size of the device 10, size of the puncture site, size (i.e., inner diameter) of the vessel to be closed, etc.

Figure 7:
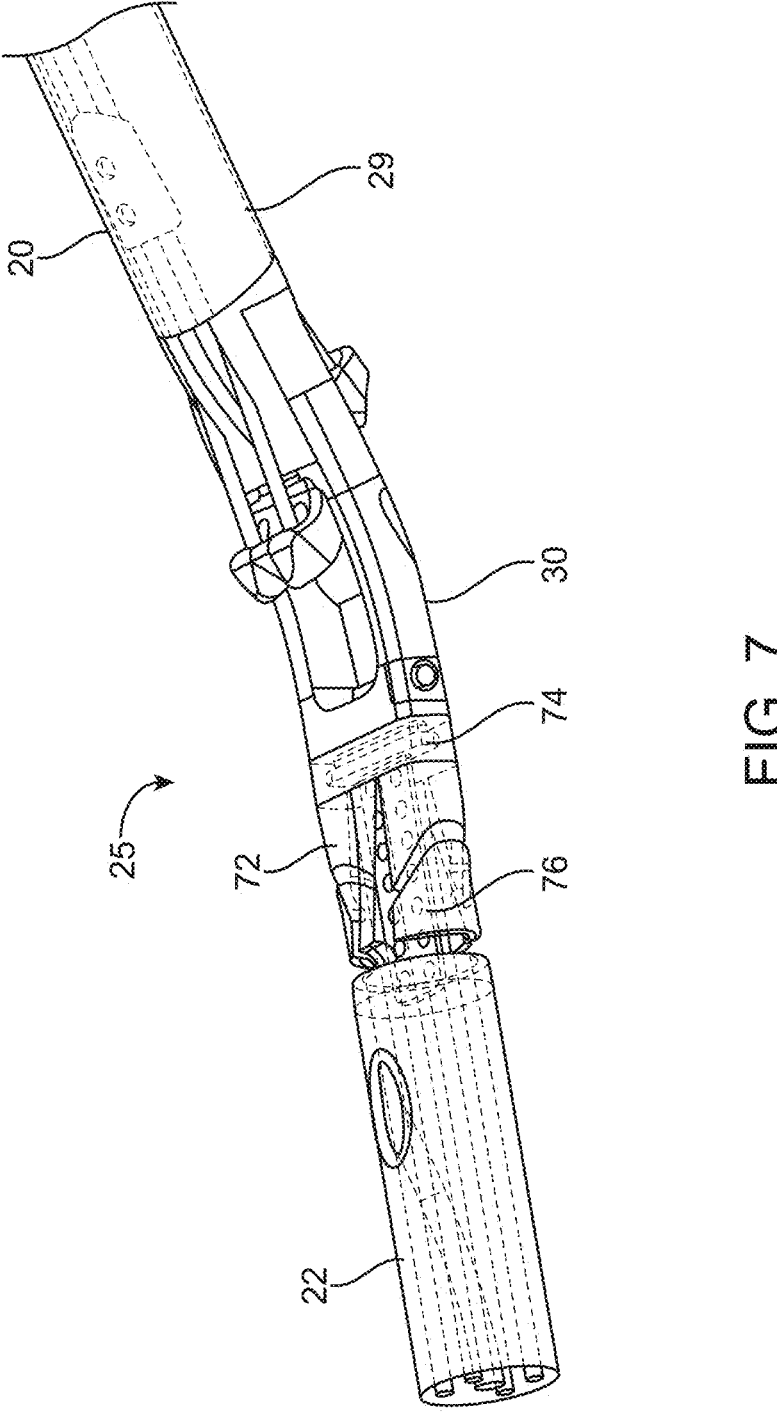
FIG. 7 shows a detailed perspective view of one variation where a flexible connector may join the distal end of the support structure to the proximal end of the distal catheter segment.

As described herein, the connection between the proximal catheter segment 20 and distal catheter segment 22 may be coupled to one another via a hinged or pivoting mechanism while in other variations, the connection may be accom- plished via a flexible structure which does not need to bend or curve by a hinged or pivoting mechanism but may bend or curve instead via a flexible coupling. FIG. 7 illustrates a detailed perspective view of one variation where a flexible connector 72 may join the distal end of the support structure 30 to the proximal end of the distal catheter segment 22. The flexible connector 72 may be formed by an elastic member which allows for either end to bend or flex while maintaining a continuous structure such as when the distal catheter segment 22 may be angled away from the vessel wall to move further distally into the vessel without imparting excessive force against the vessel interior.

In one variation, the flexible connector 72 may be formed by an elastomeric polymer formed to extend from the distal end of the support structure 30. An attachment feature 74 such as a cleat, shoulder, projection, etc. may be formed to protrude from the distal end of the support structure 30 to provide an attachment point to enhance the coupling between the support structure 30 and the flexible connector 72. Furthermore, a stiffening component 76 may also be incorporated to extend at least partially within or entirely through the flexible connector 72 to enhance rigidity to the coupling as well as to allow for more material attachment between the flexible connector 72 and the support structure 30. In one variation, the stiffening component 76 may be integrated with support structure 30 to extend distally from the support structure 30 over which the flexible connector 72 may be formed. In other variations, the stiffening component 76 may be incorporated as a component separate from the support structure 30 but which attached to the support structure 30, e.g., insertion, over-molding, bonding, mechanical fasteners, etc.

In either case, the stiffening component 76 may be formed to have a continuous smooth surface or it may be formed with a number of projections or features. In other variations, the stiffening component 76 may be formed with a number of through-holes which function to reduce the rigidity of the component 76 and may further allow for the material of the connector 72 to flow into the through-holes during manu- facturing to promote a secure attachment between the flex- ible connector 72 and support structure 30. The stiffening component 76 may also be formed to have a flat, ribbon-like profile which allows for the directional bending or flexing between the proximal and distal catheter segments 20, 22 within a first plane (e.g., up-down), but resists deflection in a transverse plane (e.g., side-side) while maintaining push- ability and trackability of the distal catheter segment 22 into the patient body.

Figures 8A, 8B:
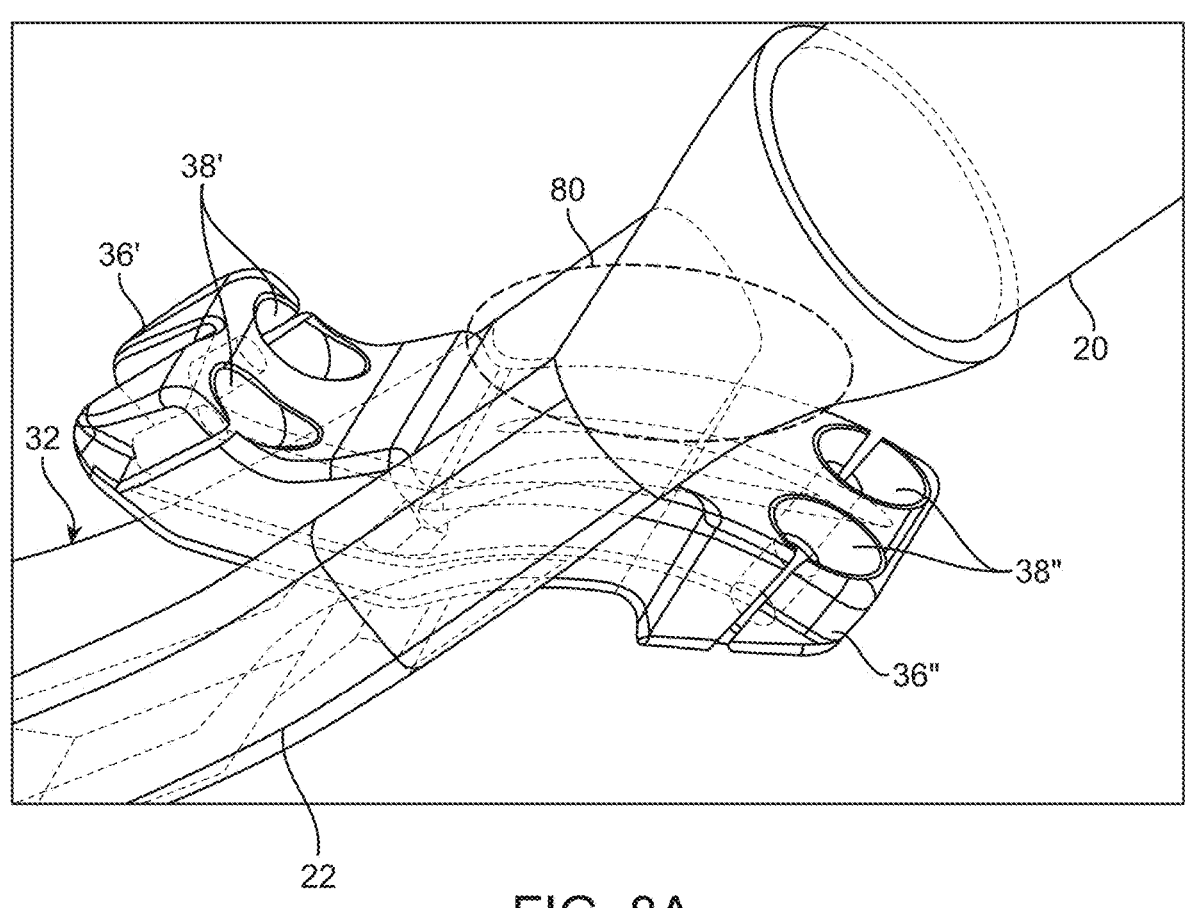
FIG. 8A shows a detail perspective view of the device transition area forming an oval or elliptical shape relative to the tissue wall.
FIG. 8B shows a detail perspective view of the proximal catheter segment angled relative to the tissue wall at the puncture site after insertion and placement.

Because the proximal catheter segment 20 is angled 66 relative to the tissue wall at the puncture site after insertion and placement, as shown by the detail perspective view of FIG. 8B, the perimeter 80 of the device transition area forms more of an oval or elliptical shape relative to the tissue wall, as shown in the detail perspective view of FIG. 8A. The perimeter 80 represents the area of the angled proximal catheter segment 20 relative to the tissue wall at the puncture site. With the reduction of the width of the perimeter 80 along the longitudinal direction of the vessel length, the device profile and perimeter 80 may expand in the transverse direction. Hence, for a device profile having, e.g., a 20 Fr equivalent circumference, the perimeter 80 is effectively wider than, e.g., 3 mm, in the transverse direction (extending transversely relative to the vessel length) and less than, e.g., 3 mm, in the longitudinal direction along the length of the vessel.

As the projected perimeter 80 forms an oval or elliptical shape, the edges of the puncture site may also be relatively closer to the outer surface of the angled proximal catheter segment 20 and the oval or elliptical perimeter 80 may hence enable the catheter segment to be used to facilitate the closure of the puncture site. This also enables the receiver member 36 to be smaller is size which further enables the device to be used in relatively smaller sized vessels. For instance, the distance between the center of each deployed needle member 42A, 42B and 82A, 82B received within the respective openings 38' and 38" of receiver member portions 36' and 36" and the free edges of the tissue against the outer wall of the proximal catheter segment and/or support structure 30 may be considered the bite margin of the amount of tissue purchase by the needle members. This bite margin may be essentially increased due to the ovalized perimeter 80. In one example, for the device profile having, e.g., a 20 Fr equivalent circumference, the resulting bite margin may range from, e.g., 1.0-2.5 mm, or may be, e.g., 2.25 mm, in one example.

Figures 9A, 9B:
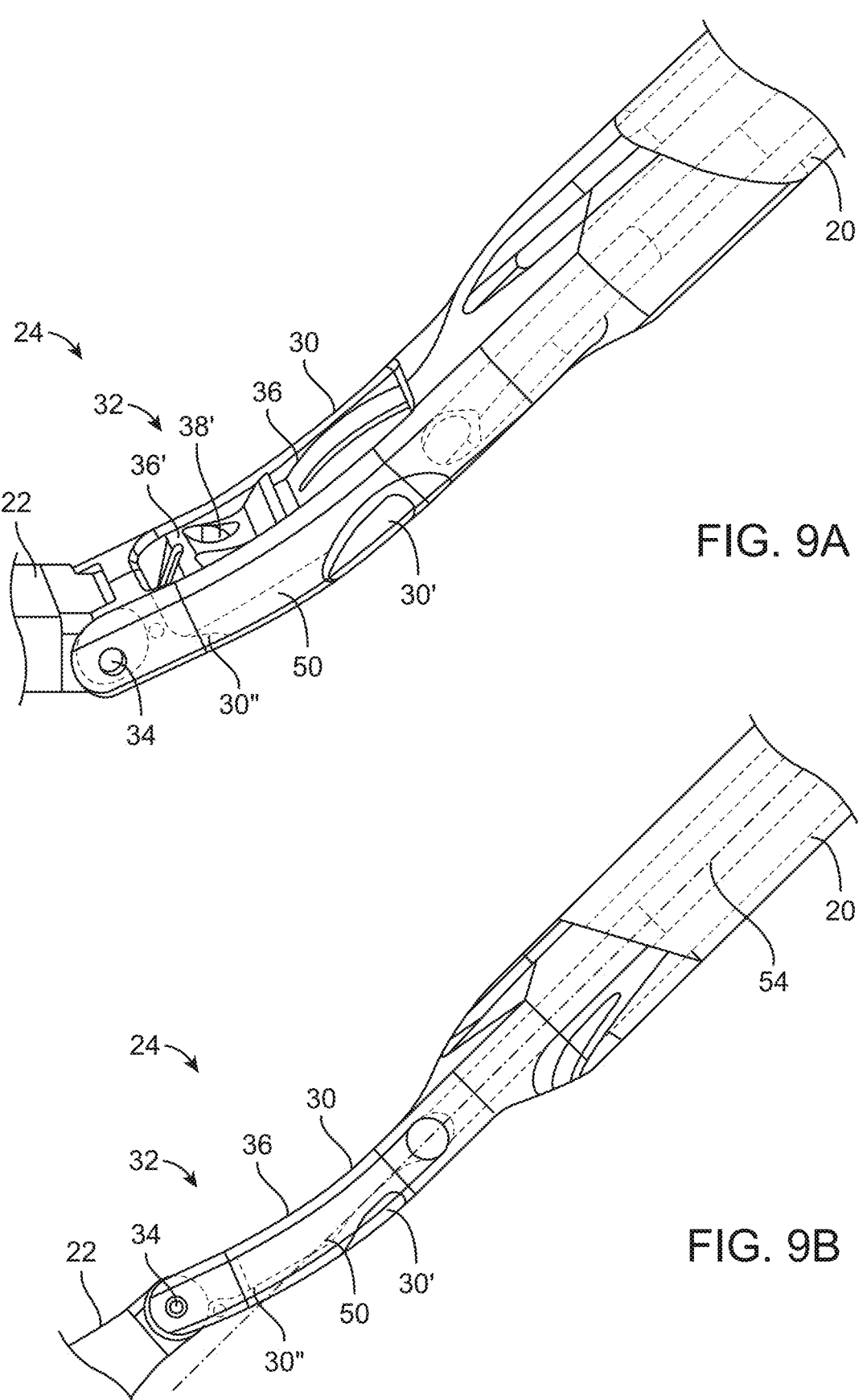
FIGS. 9A and 9B show detail perspective and side views of the receiver member undeployed within the receiving area of the support structure.

A more detailed description of the receiver member deployment is shown in the detail perspective and side views of FIGS. 9A-9B. As shown, the receiver member 36 may be seen in its low-profile delivery configuration where the receiver member 36 remains undeployed within the receiving area 32 of support structure 30. The first receiver portion 36' and openings 38' may be seen exposed along a first side of the support structure 30 while the receiver member remains unobtrusive and low-profile.

Figures 10A, 10B:
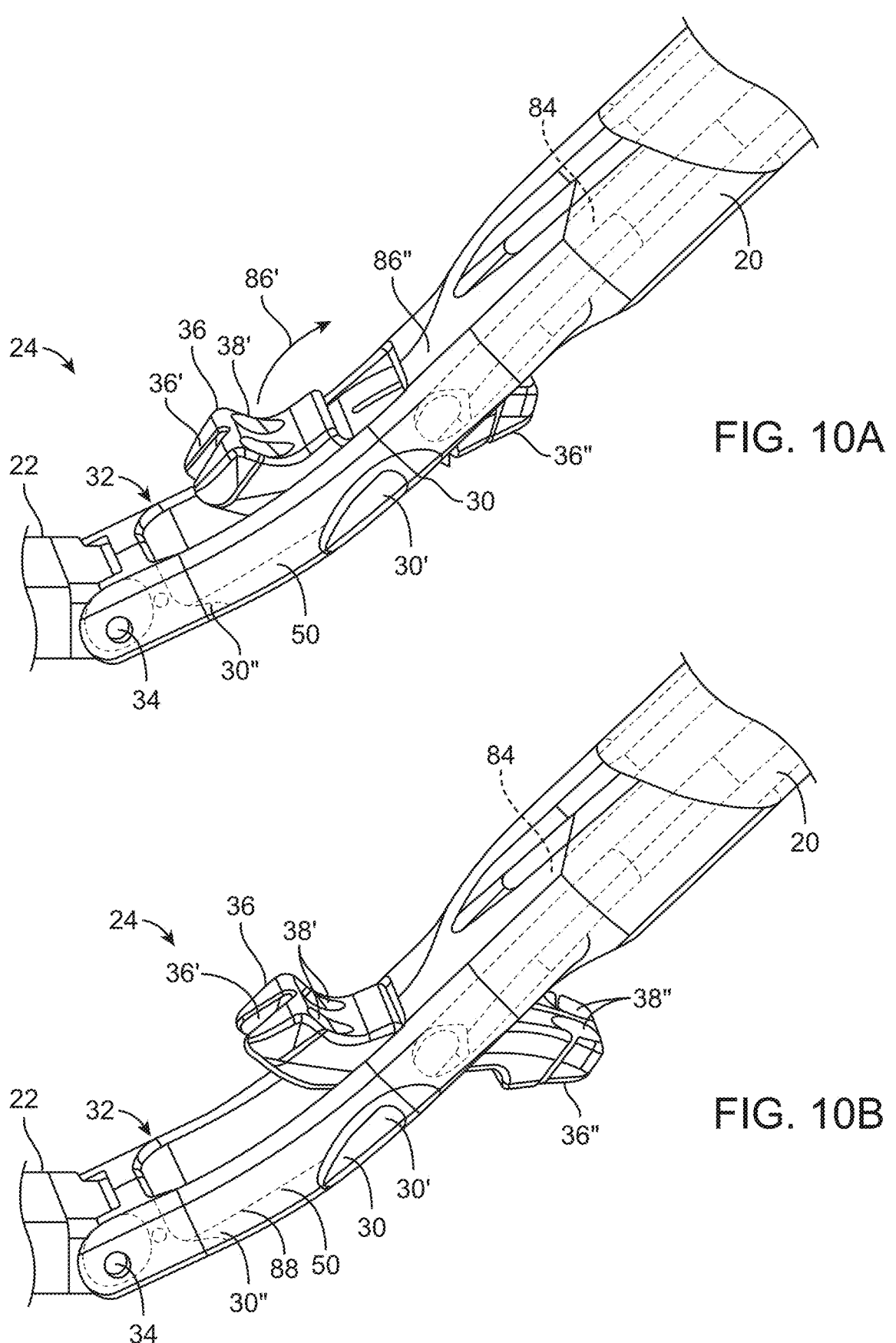
FIGS. 10A and 10B show detail perspective views of the receiver member being rotated and pulled proximally into its deployed and angled configuration.

Actuation of a push/pull member 84, such as a rod, located internally of proximal catheter segment 20 (and optionally actuated via first actuation mechanism 14 and/or second actuation mechanism 16) may be pushed to maintain the low-profile configuration of receiver member 36 or pulled to deploy the receiver member 36, as shown in the perspective detail view of FIG. 10A. As the receiver member 36 is deployed, the receiver member 36 may rotate as indicated by rotational arrows 86' while being pulled proximally as indicated by directional arrow 86" until the receiver member 36 abuts the distal end of the proximal catheter segment 20 in its deployed and angled configuration, as shown in the detail perspective view of FIG. 10B. The internal walls of the support structure 30 may define one or more guides or rails 88 symmetrically along each of the supports along which the receiver member 36 may travel and rotate into its deployed position. These guides or rails 88 may provide a travel path such that when the push/pull member 84 is actuated again for reconfiguring the receiver member 36 back into its low-profile configuration after suture delivery, the push/pull member 84 may be pushed to urge the receiver member 36 to travel distally along the guides or rails 88 so that it may rotate back into its delivery configuration shown in FIGS. 9A-9B.

Figure 11A:
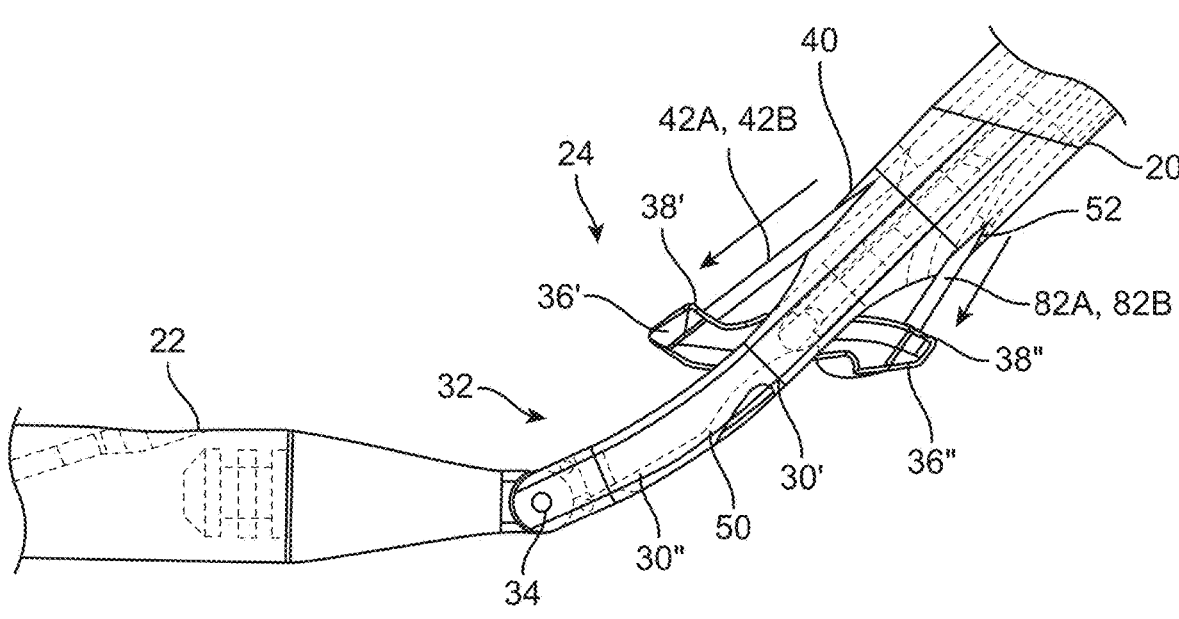
FIGS. 11A and 11B show detail side and cross-sectional side views of two forward needle members and two rear needle members advanced distally from the openings until their distal ends are received within the corresponding openings within the receiver member.
Figure 11B:
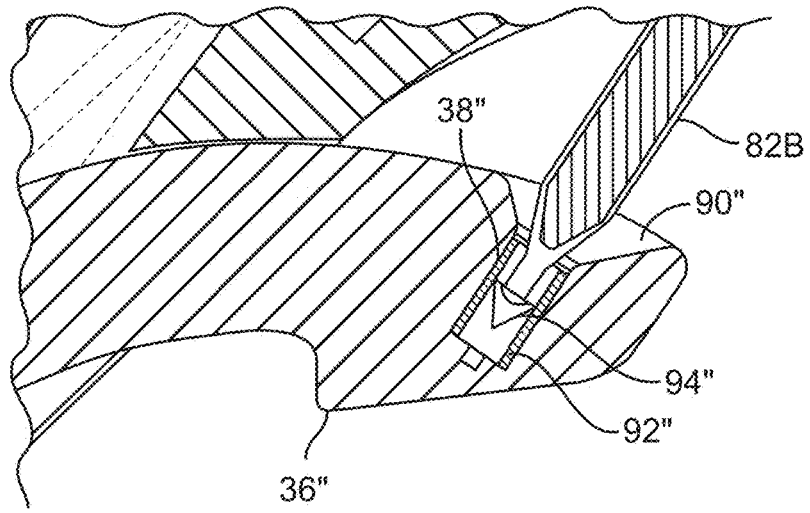
Figure 11C:
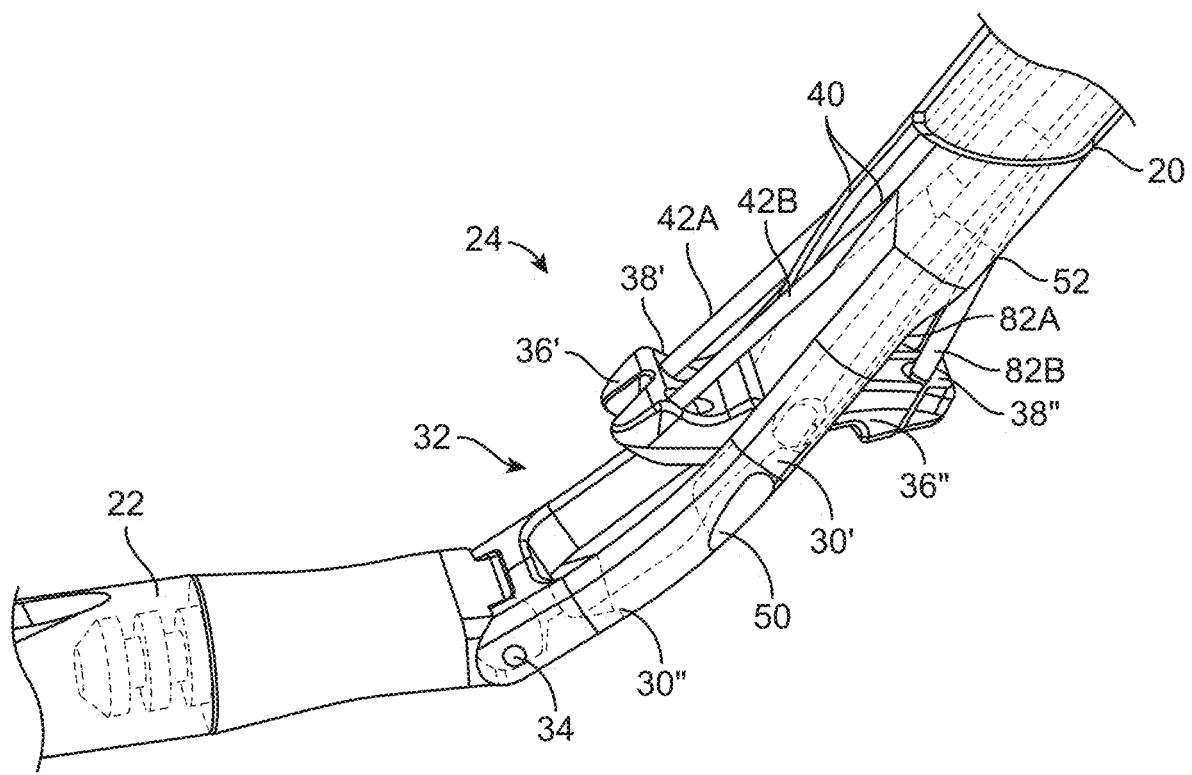
FIG. 11C shows a perspective view of the needle members from FIG. 7.

Once the receiver member 36 has been suitably deployed and is positioned against the internal vessel wall around the puncture site, the needle members may then be deployed distally from the proximal catheter segment 20. FIG. 11A shows a detailed side view and FIG. 11C shows a perspective view of how, in one variation, the two forward needle members 42A, 42B may be advanced distally from the openings 40 until the distal ends are received within the corresponding openings 38' when actuated by, e.g., second actuation mechanism 16 located on handle 12. Similarly, the two rear needle members 82A, 82B may be advanced distally from the openings 52 until the distal ends are received within the corresponding openings 38". Actuation of the two rear needle members 82A, 82B may be simultaneous with the actuation of the two forward needle members 42A, 42B while in other variations, the actuation may be optionally staggered. Each needle member may be advanced linearly to travel along a straight path once exited from the openings 40, 52. Alternatively, each needle member may be advanced linearly to travel along a slightly curved path once exited from the respective openings 40, 52 such that the two forward needle members 42A, 42B may be curved slightly upon exiting openings 40 (e.g., by a curved exit lumen) to travel slightly radially away from the surface of proximal catheter segment 20 and the two rear needle members 82A, 82B may also be curved slightly upon exiting openings 52 (e.g., by a curved exit lumen) to also travel slightly radially away such that their travel path diverges from that of the two forward needle members 42A, 42B. The angles and lengths of each needle member may be determined by the desired bite margin relative to the tissue around the puncture site. In one variation, the bite margin may be targeted to be anywhere from, e.g., 1.0-2.5 mm or 2.25 mm, as discussed herein.

With each needle member deployed, each needle member may penetrate through the vessel wall at its own discrete location, as shown in FIG. 11C. Each of the needle members may have its own piercing tip 94" (which may be optionally barbed) which is received within each respective opening 38" along the receiver portion 36", as shown in the detail partial cross-sectional side view of FIG. 11B. Each of the openings 38" may define a tapered conically shaped portion 90" to facilitate receipt of the piercing tip 94" into the opening 38" such that the piercing tip 94" is inserted into a corresponding coupling member 92" which is releasably secured within the opening 38". The coupling member 92" may be configured as a tubular receiving member having an inner diameter which is sized to receive the piercing tip 94" and become secured to the piercing tip 94" such that proximal withdrawal of the piercing tip 94" from the opening 38" may pull or release the coupling member 92" from the opening 38" along with the tip 94". The inner diameter of the coupling member 92" may optionally incorporate features such as projections which enable the coupling member 92" to become secured to the piercing tip 94". The needle members may be sized to have a diameter ranging from, e.g., 0.5-1.0 mm, and the outer diameter of each corresponding coupling member may be sized to not exceed the outer diameter of each respective needle member to ensure that the coupling may be removed smoothly through the needle penetration sites without catching on tissue.

As noted, each needle member may include its own piercing tip and each receiving opening along the receiver may also incorporate its own coupling member for engagement with a respective needle member.

Any of these receiver and needle deployment variations may be used in any number of combinations or embodiments together with any of the device features described herein including any of the suture management, suture delivery, tissue management, alternative device embodiments, or suture capture and securement features described herein.

Suture Management

As the device 10 may be used to approximate tissue openings such as arteriotomies or venotomies, two separate lengths of suture which are independent of one another may be preloaded within the device 10 and used with the needle members to deliver suture through the vessel walls in which the deployed suture may be used to approximate the tissue edges for hemostasis (as described in further detail herein). This may be accomplished without the need of any suture knots. Due to the lengths of the suture, the suture may be stored and deployed into the tissue using a number of different suture management variations.

The sutures used in any of the embodiments described may include any number of different types of sutures, e.g., polymeric, metallic, absorbable, non-absorbable, braided, monofilament, coated, uncoated, etc. A single device may use the same suture type for each individual suture loop. Alternatively, different suture types may be used in a single device where two or more suture loops are deployed so that different suture types are deployed by a single device for tissue closure.

Figures 12A, 12B:
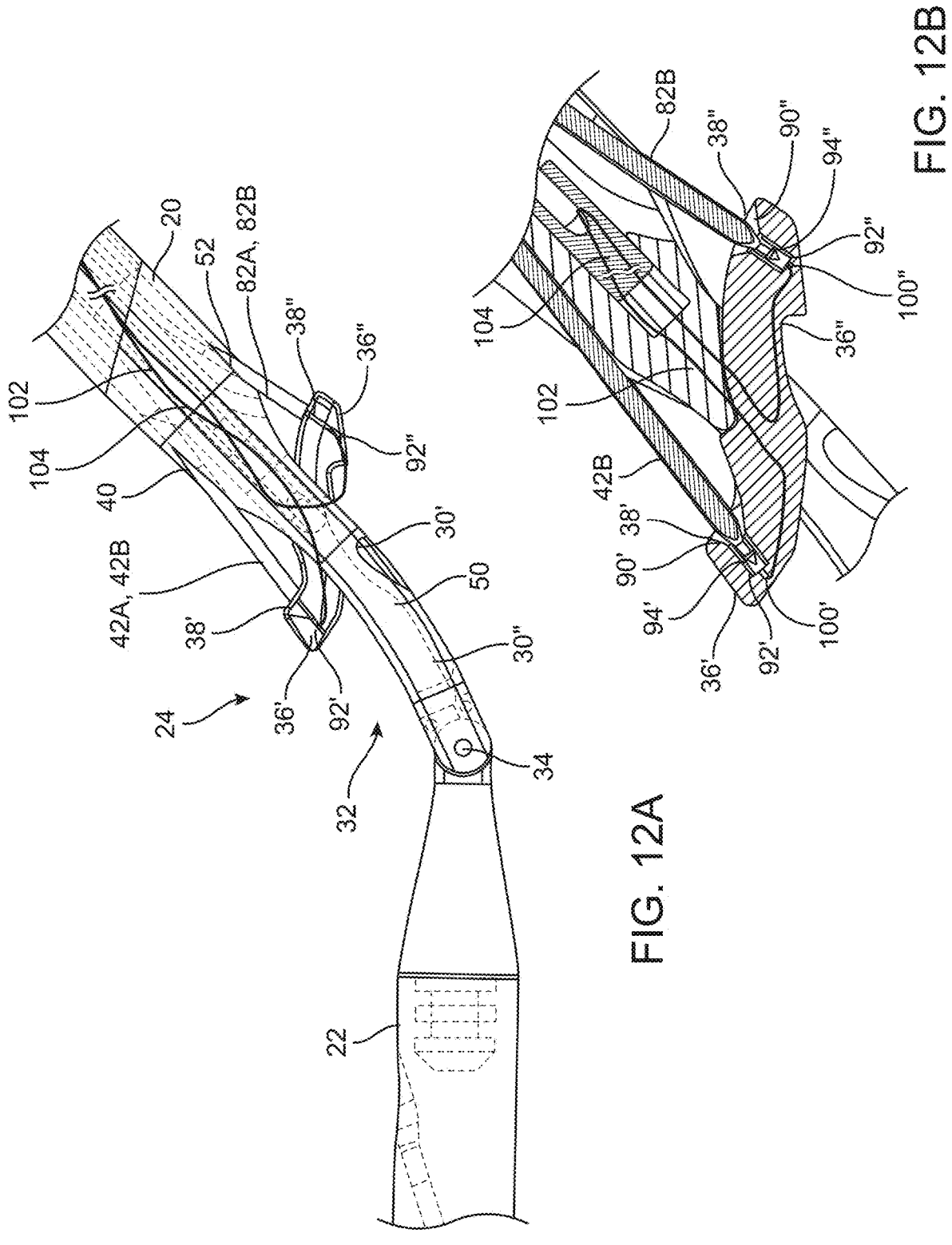
FIGS. 12A and 12B show detail side and cross-sectional side views of one variation of how the suture lengths may be pre-loaded within the proximal catheter segment of the device.

FIG. 12A shows a detail side view of one variation where the suture 102 may be pre-loaded within a lumen or space 104 defined within the length of the proximal catheter segment 20. Each of the coupling members 92', 92" on opposite ends of the receiver member may be coupled to one another via its own length of suture 102. As illustrated in the partial cross-sectional side view of FIG. 12B, coupling member 92' positioned within opening 38' of first receiver portion 36' may have its distal end 100' coupled to a first terminal end of suture 102. The length of suture 102 may be routed through a lumen defined through the receiver member 36 so that the suture 102 passes proximally through the receiver member 36 and into an interior lumen or space 104 within proximal catheter segment 20. This suture 102 length may be stored within the proximal catheter segment 20 and may further pass distally back through a lumen defined through the receiver member 36 and toward the second coupling member 92" where the second terminal end of the suture 102 may be coupled to the distal end 100" of the second coupling member 92". Similarly, a second length of suture which is independent of suture 102 may have its first and second terminal ends attached to corresponding coupling members which are each positioned within their respective openings along the first receiver portion 36' and second receiver portion 36" such that the second length of suture is likewise pre-loaded within the space or lumen within proximal catheter segment 20.

When the two forward and two rear needle members are deployed through the tissue and received into their respective openings and coupling members, each of the piercing tips of each needle member may engage the coupling members which may then be pulled proximally to pull the coupling members and suture ends proximally back through the pierced tissue openings. Each of the suture lengths may range anywhere from, e.g., 30-75 cm or greater depending upon the depth from the skin surface of the tissue opening to be closed as well as the device embodiment utilized.

As the suture 102 remains within the device and is deployed directly into and against the tissue within any unnecessary contact, the risk of the suture 102 touching the skin surface or other tissues (as with percutaneous procedures) is avoided and reduces any risk of bacterial contamination being entrained or drawn into the pierced tissue by the suture 102. Furthermore, as the use of knots is eliminated, the additional risk of bacterial contamination is further reduced or avoided entirely following the procedure.

Figure 13:
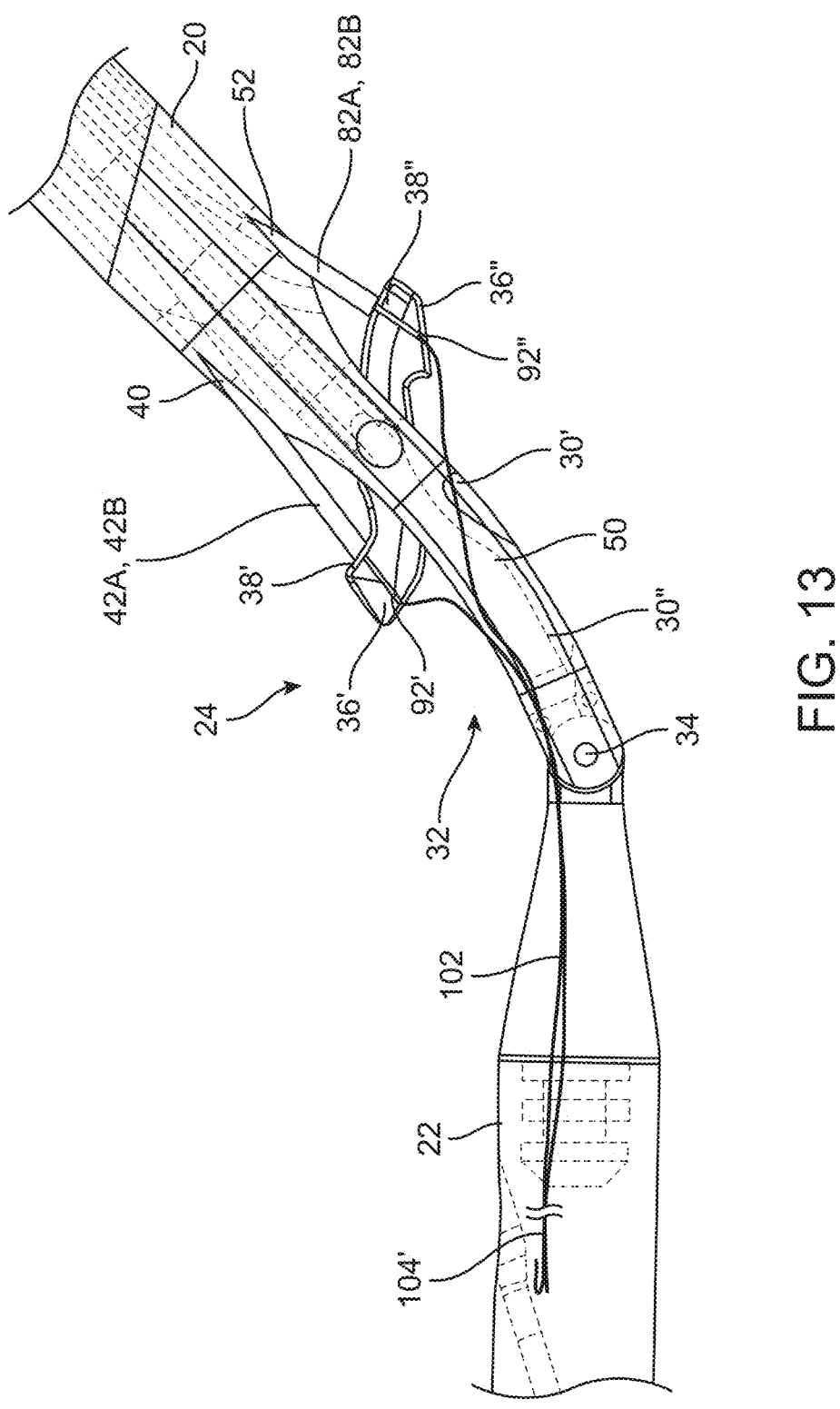
FIG. 13 shows a detail side view of another variation of how the suture lengths may be pre-loaded within the distal catheter segment of the device.

FIG. 13 illustrates another variation in which the suture lengths may be stored within a lumen or space 104' defined within the distal catheter segment 22 rather than the proximal catheter segment 20. As shown, the terminal ends of each suture length may still be attached to opposite coupling members but the suture length may be passed either through lumens and/or slots defined within the receiver member or they may pass outside the device and into the lumen or space 104' within the distal catheter segment 22.

Figures 14, 15:
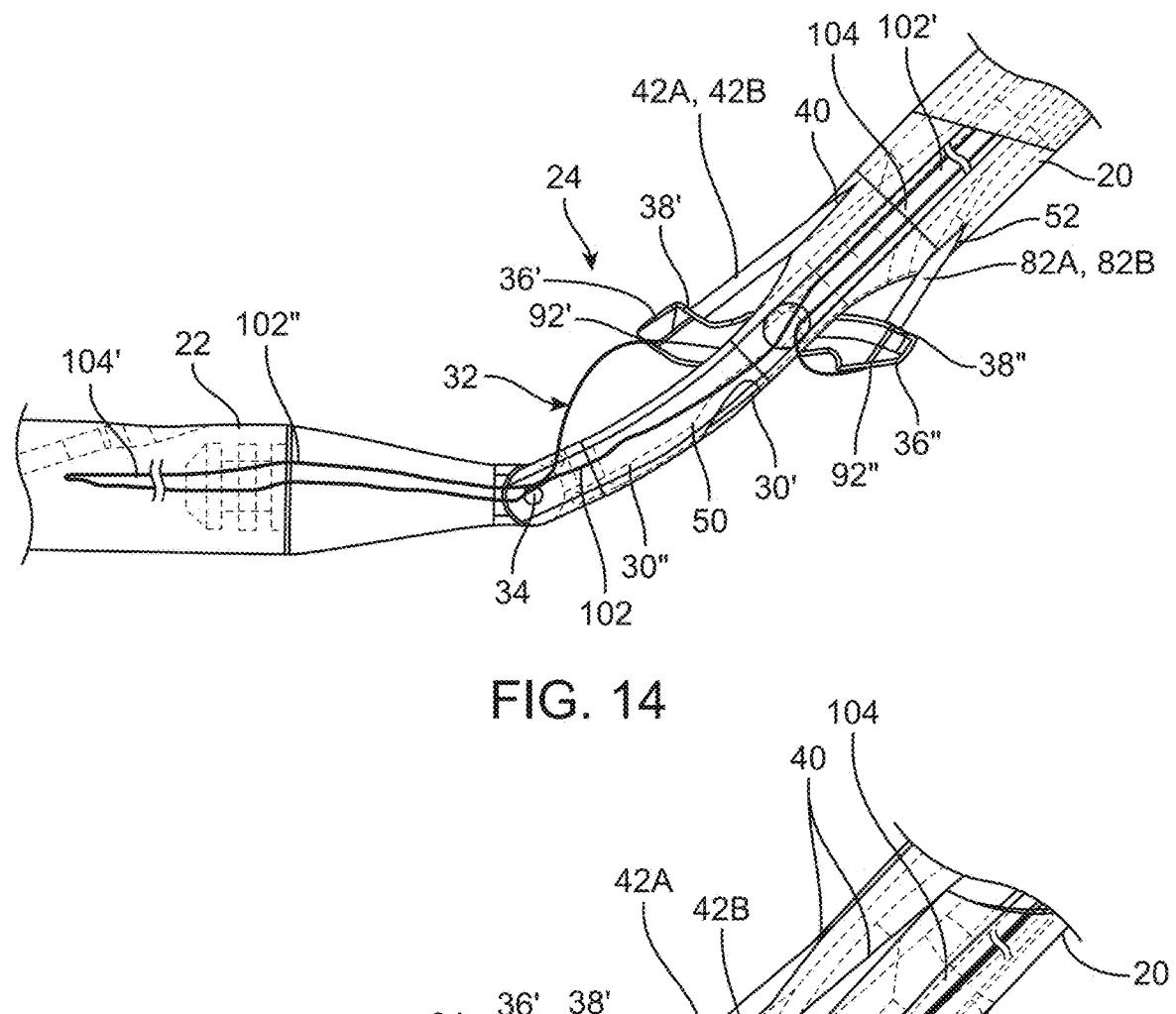
FIG. 14 shows a detail side view of another variation of how the suture lengths may be pre-loaded within the proximal and distal catheter segments of the device.
FIG. 15 shows a detail side view of another variation of how the suture lengths may be pre-loaded within the proximal catheter segment of the device and further arranged to create a cross-stitch pattern.

FIG. 14 illustrates yet another variation in which the terminal ends of each suture length may be similarly attached to each opposed coupling member, but a first portion 102' of the suture length 102 may be stored within the lumen or space 104 within the proximal catheter segment 20 and a second portion 102" of the same suture length 102 may be stored within the lumen or space 104' within the distal catheter segment 22. In this manner, the suture length 102 may pass through or along the support structure 30 to provide extra suture length (e.g., doubling the length of suture 102 to 40-100 cm or greater) in the event that extra suture length is needed or desired. Moreover, such an arrangement may simplify the payout of the suture loop to ensure that any extraneous suture remains within the device during deployment. Furthermore, this arrangement may also prevent suture breakage during suture deployment.

FIG. 15 illustrates yet another variation in which the terminal ends of each suture length may be configured to cross in order to form a cross-stitch pattern across the puncture site. Rather than having the terminal ends of one suture length 102 being coupled to coupling members which are directly opposite to one another along first receiver portion 36' and second receiver portion 36", the terminal ends of one suture length 102 may be attached to coupling members which are positioned opposite and adjacent along first receiver portion 36' and second receiver portion 36", as shown. The crossing may be achieved by crossing the coupling members on either the first receiver portion 36' or the second receiver portion 36" and the suture length may be stored in either the proximal catheter segment 20, distal catheter segment 22, or both.

Figure 16A:
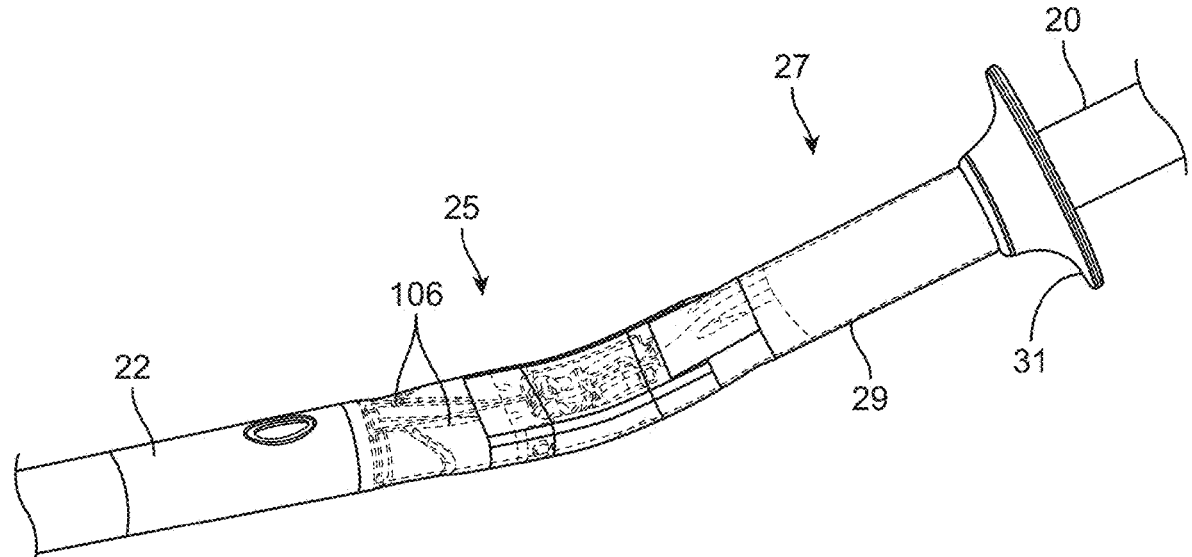
FIGS. 16A and 16B show detail perspective top and bottom views of the deployment segment with the sheath assembly in its distal position where the sheath member covers at least a portion or all of the deployment segment.
Figure 16B:
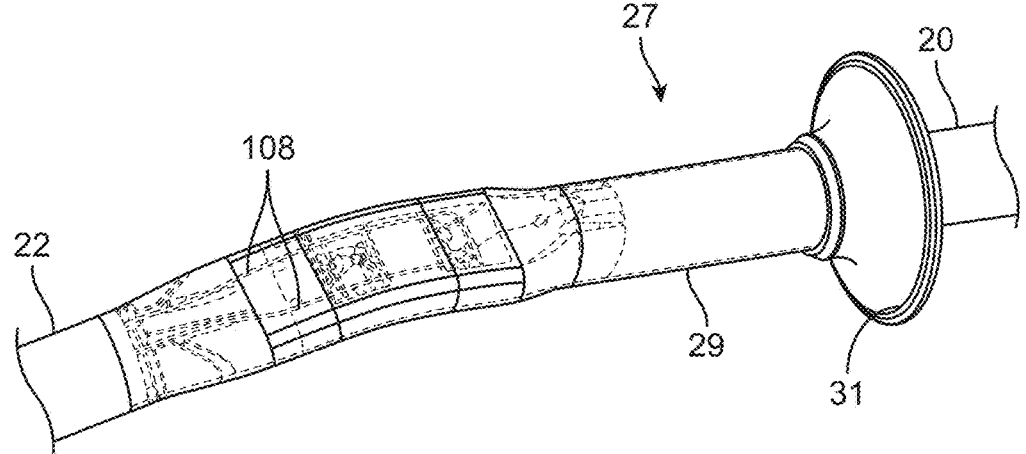

In variations of the device where the suture 102 length is routed and/or stored within the distal catheter segment 22, the suture 102 may extend from each respective receiver portion 36', 36" and pass along or through one or more respective suture channels 106, 108 defined along the flexible connector and/or a proximal portion of the distal catheter segment 22. FIGS. 16A and 16B illustrate detail perspective top and bottom views of the deployment segment 25 with the sheath assembly 27 in its distal position where the sheath member 29 covers at least a portion or all of the deployment segment 25 and FIGS. 17A and 17B illustrate detail perspective top and bottom views of the deployment segment 25 with the sheath assembly 27 in its retracted proximal position where the deployment segment 25 is exposed.

Figure 17A:
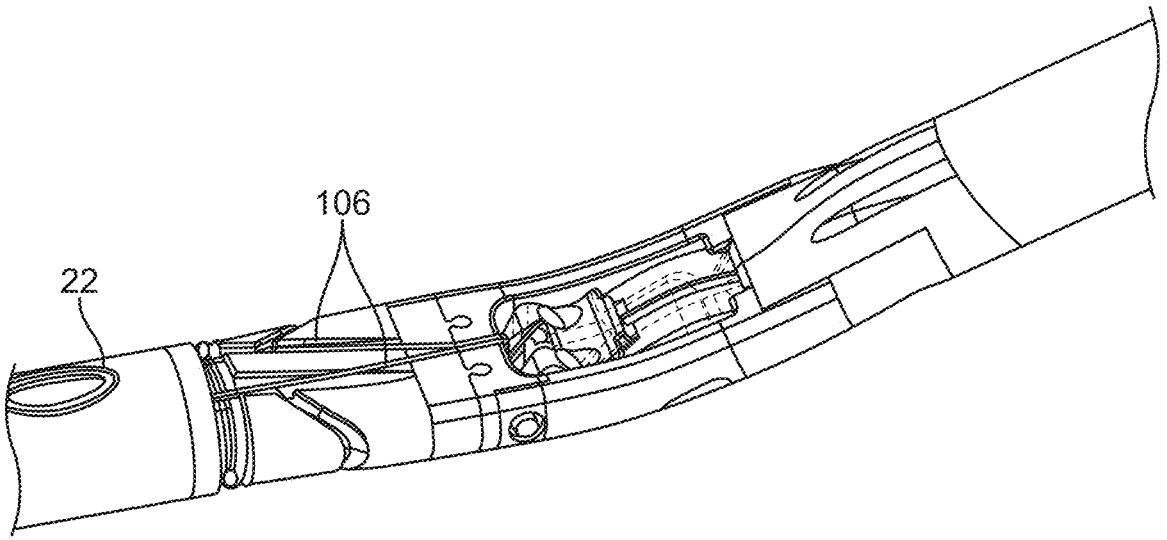
FIGS. 17A and 17B show detail perspective top and bottom views of the deployment segment with the sheath assembly in its retracted proximal position where the deployment segment is exposed.
Figure 17B:
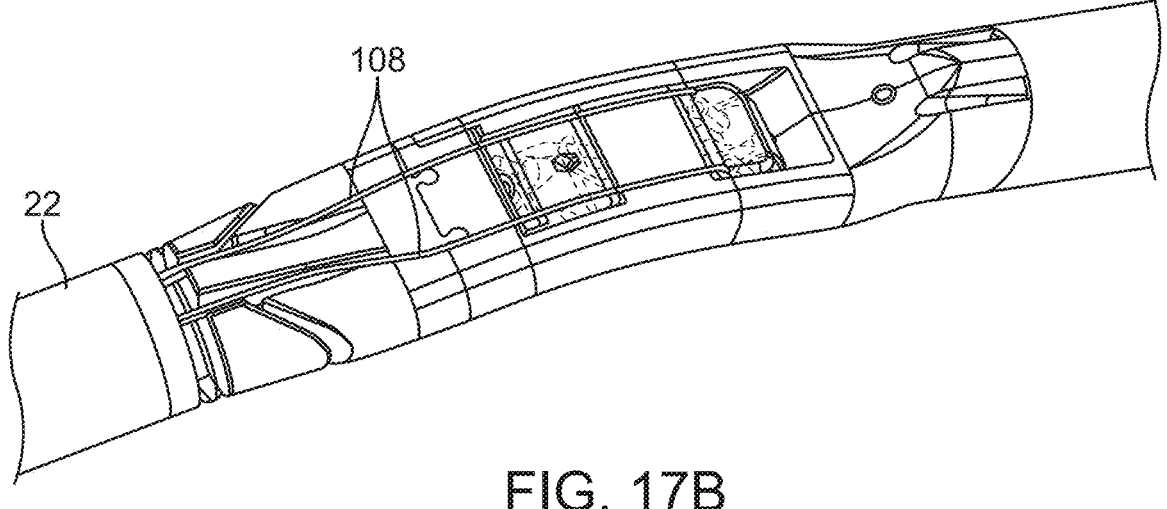

FIGS. 16A and 17A illustrate how the suture channels 106 may be defined to extend from a common channel and diverge into, e.g., two separate channels, where the suture 102 from the first receiver portion 36' may extend along the channels 106 and route into the interior lumen of the distal catheter segment 22. FIGS. 16B and 17B illustrate how the suture channels 108 may extend in parallel along the deployment segment 25 such that the suture 102 from the second receiver portion 36" may extend along the channels 108 and similarly route into the interior lumen of the distal catheter segment 22. When the sheath member 29 is positioned over the deployment segment 25, the suture lengths positioned within the suture channels 106, 108 may remain covered and protected from dislodgement or from contacting tissue surfaces such as the skin surface during insertion and advancement within the tissue.

Figure 18A:
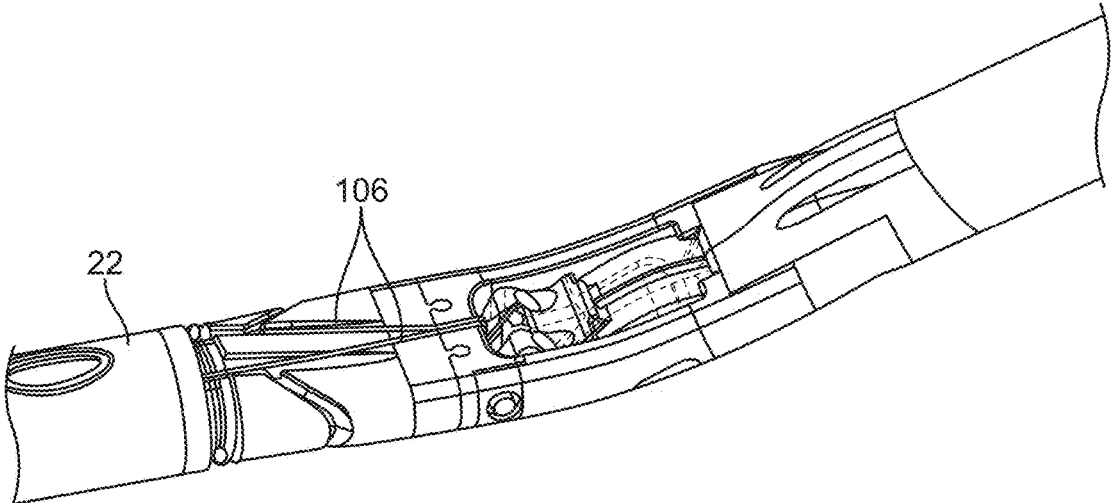
FIG. 18A shows the suture channels to illustrate the positioning of the suture length externally of the device.
Figure 18B:
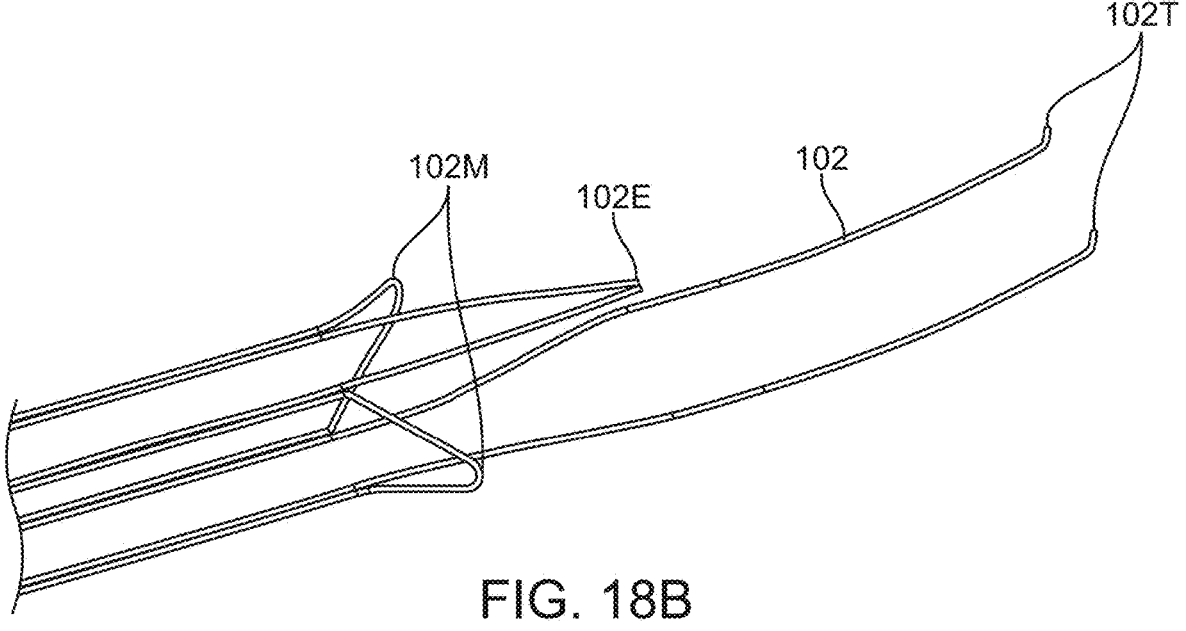
FIG. 18B shows how the suture length is routed within and through the interior of the device.

FIG. 18A illustrates the suture channels 106 for reference in how the suture length is routed within and through the interior of the device, as shown in FIG. 18B, for comparison. As shown, the terminal ends 102T of suture 102 may each be attached to a respective coupling member contained within each respective opening 38 along the first receiver portion 36', second receive portion 36", or both first and second receiver portions 36', 36" depending upon the type of stitch used. In this variation where the suture 102 length is stored within the lumen or space 104' defined within the distal catheter segment 22 (such as that shown in FIG. 13 or 14), the remaining terminal ends 102E opposite to each terminal end 102T of each suture length may be routed through the suture channels 106 to extend towards the corresponding coupling members contained within each opposed opening 38 opposite to where the terminal ends 102T are coupled. In this variation, the terminal ends 102T may be coupled to the respective coupling members within the second receiver portion 36" and the opposite terminal ends 102E may be coupled to the respective coupling members within the first receiver portion 36'. The remainder of the suture length may be routed within the lumen or space 104' such that the approximate center portion 102M of each individual suture length is positioned proximally within the distal catheter segment 22, as shown. This center portion 102M of, e.g., about +/−5 cm, along with, e.g., about 0-3 cm, of trim length arc the portions of the suture expected to be left within the patient's body following securement, as described in further detail herein. Depending upon the length of the distal catheter segment 22, the length of the suture 102 within the device may range anywhere from, e.g., 15 to 90 cm, in length.

Figure 18C:
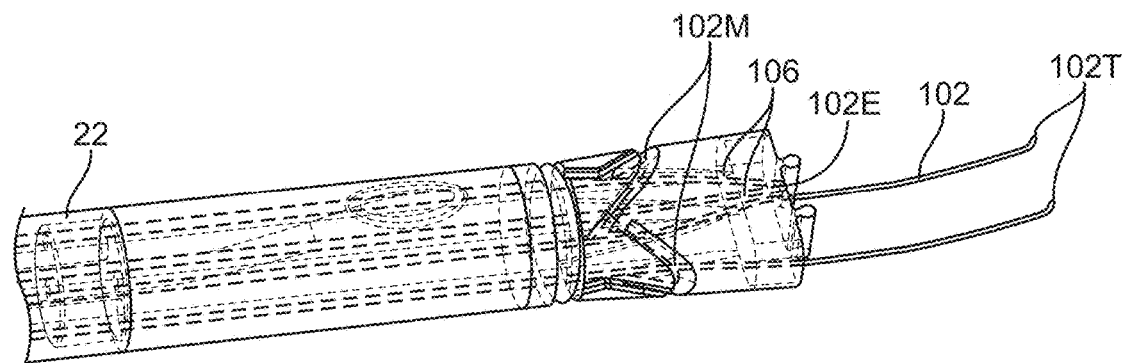
FIGS. 18C and 18D show one variation of the routing of the suture lengths within the interior of the distal catheter segment.
Figure 18D:
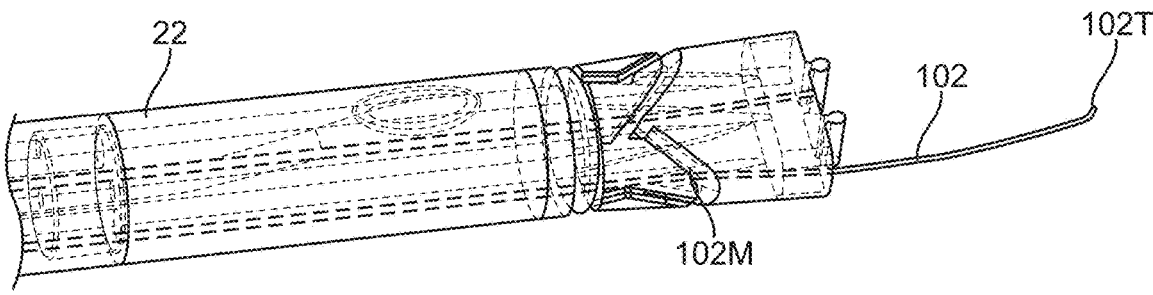
Figure 18E:
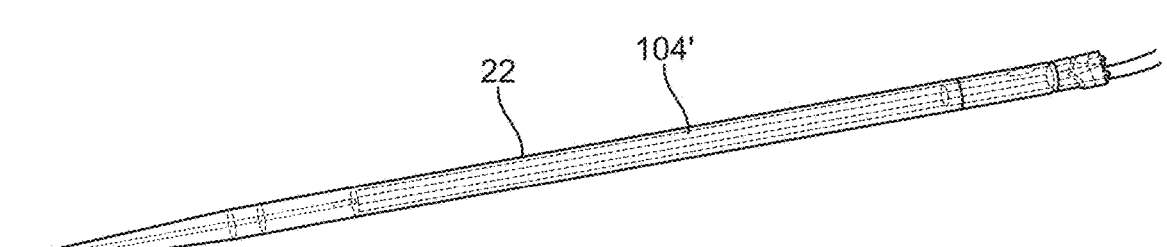
FIG. 18E shows how the suture lengths may be positioned within the length of the lumen or space defined within the distal catheter segment.

FIGS. 18C and 18D illustrate one variation of the routing of the suture lengths from FIG. 18B within the interior of the distal catheter segment 22 to illustrate how each respective suture length may be routed into the lumen or space 104' and to pass proximally back towards the proximal end such that the center portion 102M may be positioned proximally within the catheter 22. FIG. 18C shows both catheter lengths while FIG. 18D shows a single suture length for clarity purposes. FIG. 18E illustrates how the suture lengths may be positioned within the length of the lumen or space 104' defined within the distal catheter segment 22.

Figure 19A:
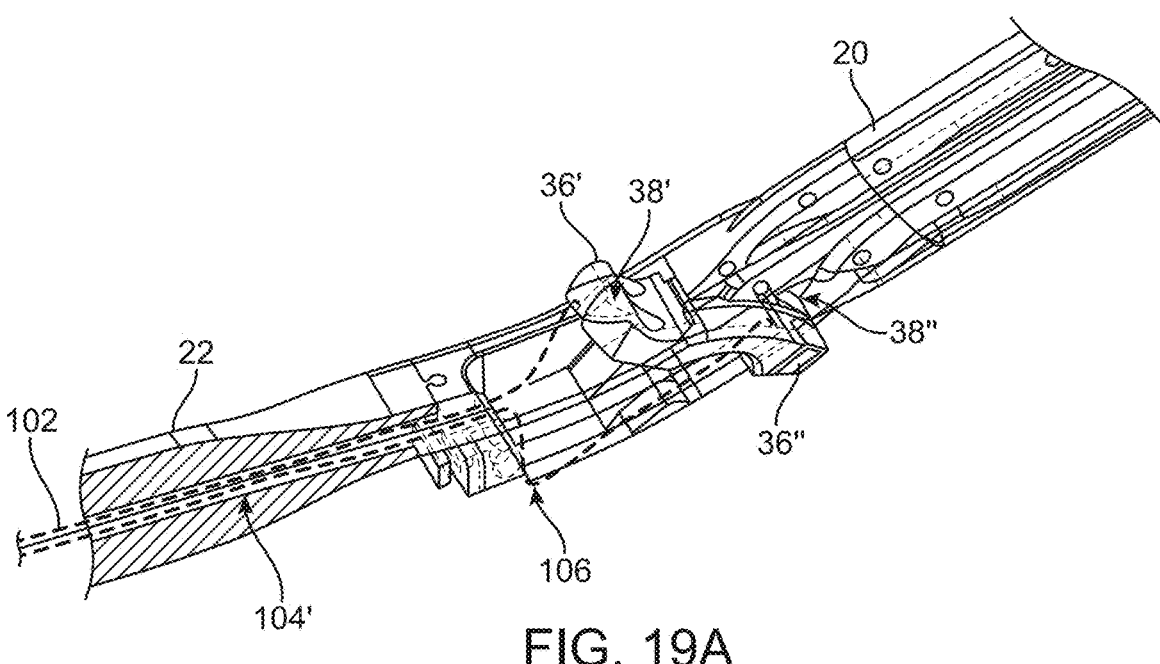
FIGS. 19A and 19B show front and rear perspective views illustrating another variation of how the suture lengths may be routed externally of the first and second receiver portions.
Figure 19B:
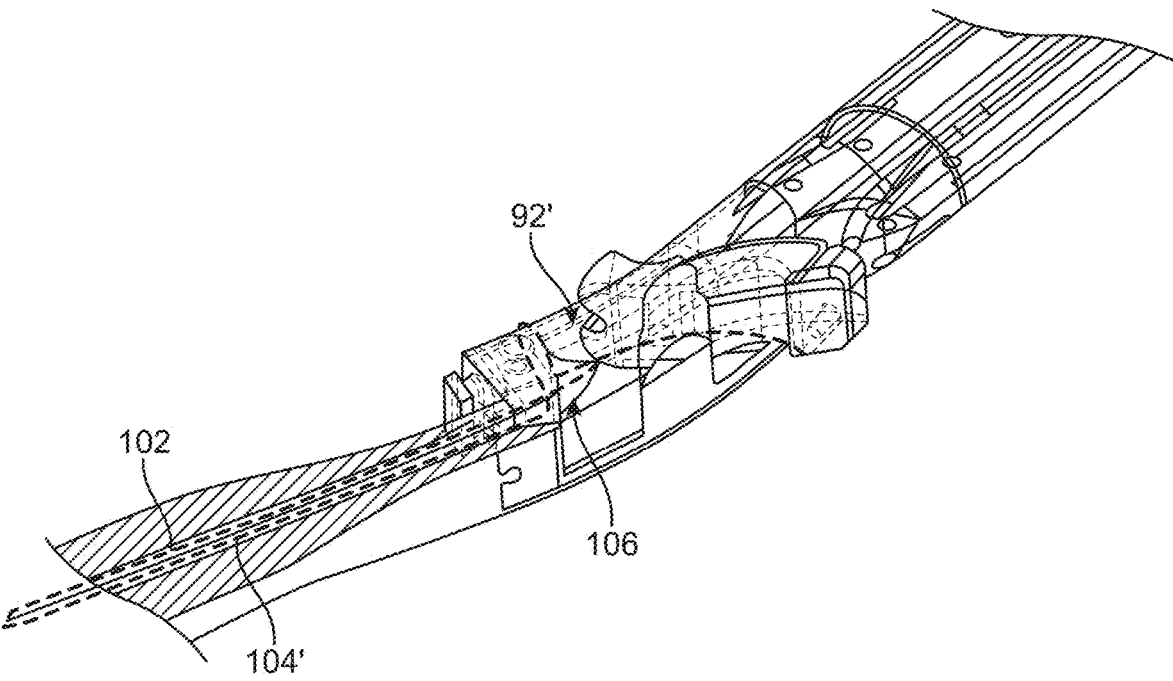

FIGS. 19A and 19B show front and rear perspective views illustrating another variation of how the suture lengths may be routed externally of the first and second receiver portions 36', 36". In this variation, a single length of suture 102 is illustrated for clarity purposes only and shows how this suture may be routed to be stored within the lumen or space 104' of the distal catheter segment 22. The first terminal end of the suture may be coupled within either of the openings 38' along the first receiver portion 36' and passed into the lumen or space 104' of the distal catheter segment 22. The second terminal end of the suture may be seen extending from either of the openings 38" along the second receiver portion 36" and may pass around, about, through, or looped about a projection or shoulder 106 (such as a cleat or bearing feature, etc.) which facilitates the suture management during delivery and deployment.

As described herein, the terminal ends of each suture length may be positioned for coupling within each opening between the first and second receiver portions 36', 36" either directly across from one another to create a straight stitch, or across and diagonal from one another to create a cross stitch pattern in the tissue opening to be approximated.

Figures 20A, 20B:
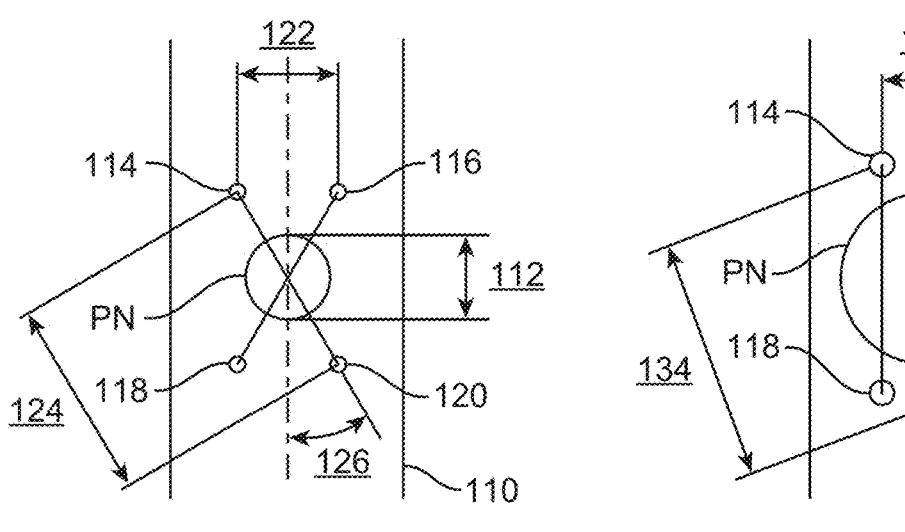
FIG. 20A illustrates a top view of the resulting cross-stitch pattern which may result under the puncture site along the vessel.
FIG. 20B illustrates a top view of the resulting parallel stitch pattern which may result under the puncture site along the vessel.

FIG. 20A illustrates a top view of the resulting cross-stitch pattern which may result under the puncture site PN along vessel 110 having a puncture diameter 112. The cross-stitch pattern shown may result from the variation of the device 10 described in FIG. 15 above. With the device inserted through the puncture site PN having diameter 112, advancement of the forward needle members 42A, 42B may result in the openings 114, 116 through the tissue wall and the rear needle members 82A, 82B may result in the openings 118, 120 shown in the tissue. The resulting suture loops may be formed to cross over one another over the puncture site PN. The distance 122 between adjacent openings 114, 116 and between 118, 120 and the distance 124 between opposing and adjacent openings 114 and 120 as well as the angle 126 between the openings and the mid-line of the vessel 110 may be controlled or adjusted by adjusting the corresponding distances between the needle members.

FIG. 20B illustrates a top view of the resulting parallel stitch pattern which may result over the puncture site PN along vessel 110 having a puncture diameter 130.

The parallel stitch pattern shown may result from the variation of the device 10 described in FIGS. 12-14 above where each suture loop may extend between opposing needle member such as between needle members 42A and 82A and between 42B and 82B. The resulting suture loops may be formed to extend in parallel with one another longitudinally along the vessel and over the puncture site PN. The distance 132 between adjacent openings 114, 116 and between 118, 120 and the distance 134 between opposing and adjacent openings 114 and 120 as well as the angle 136 between the openings and the mid-line of the vessel 110 may be controlled or adjusted by adjusting the corresponding distances between the needle members.

Figure 20C:
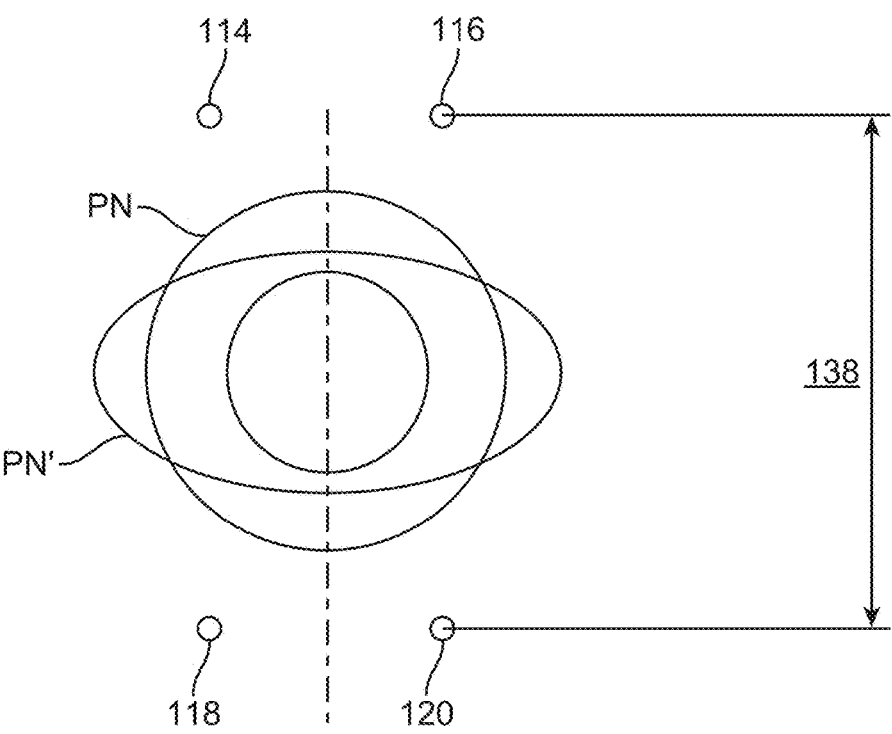
FIG. 20C illustrates yet another variation where the puncture site for a typical circular opening in the vessel wall is compared to the oval or elliptically shaped opening formed by the angling of the proximal catheter segment relative to the tissue surface.

FIG. 20C illustrates yet another variation where the puncture site PN for a typical circular opening in the vessel wall is compared to the oval or elliptically shaped opening PN' formed by the angling of the proximal catheter segment 20 relative to the tissue surface, as further illustrated in FIG. 8A. As shown, the bite margin between the insertion locations of the needle members relative to the exposed edges of the puncture site PN' may result in a relatively greater bite margin than with a circularly shaped puncture site PN when the distance 138 between the opposed needle members remains the same. Utilizing an ovalized profile allows for the device 10 to reduce thickness in one axis (transverse relative to the vessel length) while growing in the other axis (along the vessel length). Promoting engagement with one axis of the opening PN', allows for the edges to be controlled for improved closure.

Figure 21A:
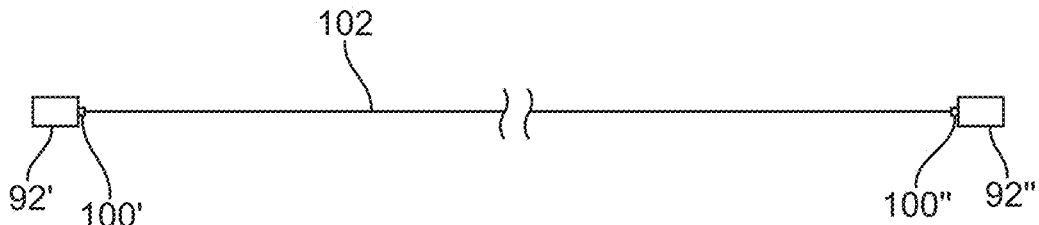
FIG. 21A shows an example of a suture length having coupling members attached to each terminal end of the suture length.

Any of these suture management variations may be used in any number of combinations or embodiments together with any of the device features described herein including any of the receiver and needle deployment, suture delivery, tissue management, alternative device embodiments, or suture capture and securement features described herein.
Suture Delivery With the use of two forward needle members and two rear needle members, two suture lengths which are independent of one another may be used between each pair of needle members, as described herein. Each terminal end of each of the suture lengths 102 may incorporate a coupling member 92', 92" attached 100', 100" to each respective coupling member, as shown in FIG. 21A. As described herein, each suture length may range, e.g., 40-75 cm or greater, and while each coupling member 92', 92" is removably secured within each respective opening along the receiver member 36, the rest of the suture length may be positioned in either a lumen or space within the proximal catheter segment 20, distal catheter segment 22, or both.

Figure 21B:
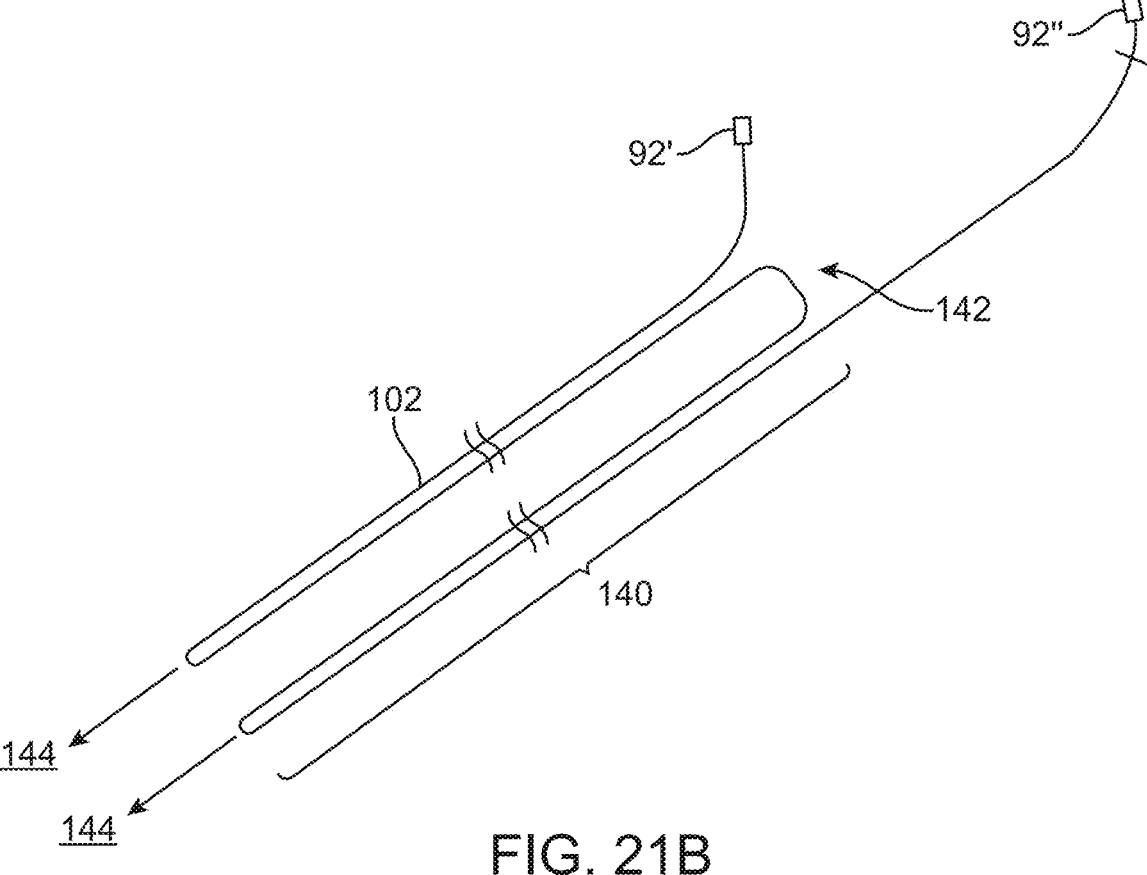
FIG. 21B shows an example of how a portion of the suture length may be retained either loosely or they may be retained by some tensioning force within the device.

As shown in FIG. 21B, a portion 140 of the suture length 102 may be retained either loosely or they may be retained by some tensioning force 144 (e.g., tension spring, spool, etc.) while the remainder may be looped 142 within the device. So long as lumen or space 104' within which the suture is retained is suitably sized, the suture length may be prevented from binding or winding upon itself during suture deployment. The suture retaining lumen or space may incorporate some tensioning mechanism to keep the non-deployed suture release in a controlled manner and the suture lumen itself does not need to be any particular shape or cross-section.

Figure 22A:
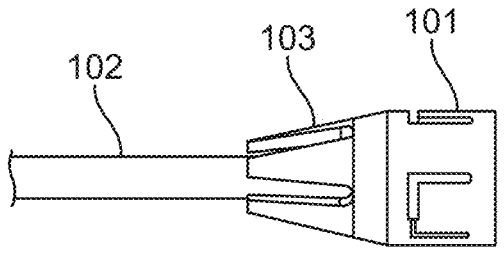
FIGS. 22A and 22B show side and cross-sectional side views of one variation in which the terminal end of the suture may be coupled to a coupling member through one or more fingers or extension members.
Figure 22B:
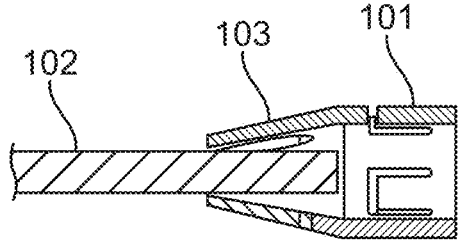

Turning now to the suture terminal ends and their attachment to the respective coupling members, the suture terminal ends may be attached to the couplings through various attachment mechanisms. FIGS. 22A and 22B show side and cross-sectional side views of one variation in which the terminal end of the suture 102 may be coupled to a coupling member through one or more fingers or extension members 103 (e.g., three or four fingers) which extend from a body section which may also define one or more projections 101 defined over a circumference of the body section. The one or more projections 101 may extend radially inward for secure engagement to the needle tips of the forward needle members 42A, 42B and/or rear needle members 82A, 82B when advanced into the body section. The fingers or extension members 103 may push or collapse radially inward upon the suture end to create a secure engagement.

Figure 23A:
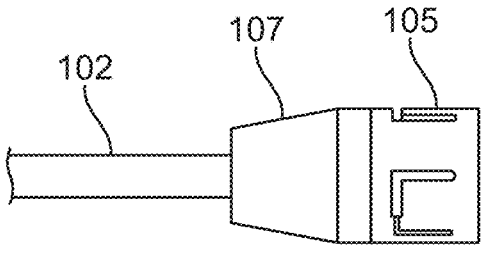
FIGS. 23A and 23B show side and cross-sectional side views of yet another variation in which a tapered portion extending from a body segment may create a securement engagement with the suture terminal end.
Figure 23B:
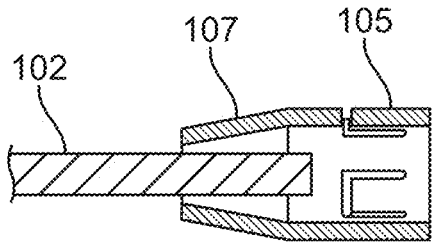
Figure 24A:
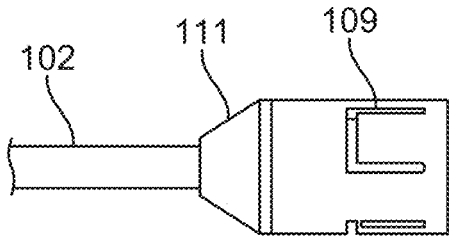
FIGS. 24A and 24B show side and cross-sectional side views of yet another variation in which in which a tapered body formed separately from the body segment may similarly be secured to the suture terminal end and attached to the body segment.
Figure 24B:
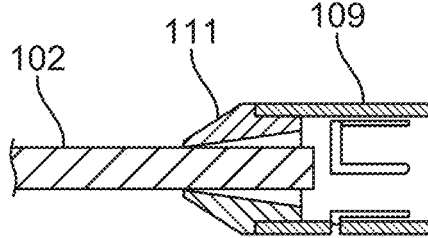

FIGS. 23A and 23B show side and cross-sectional side views of yet another variation in which a tapered portion 107 extending from a body segment 105 may create a securement engagement (e.g., via swaging) with the suture terminal end. FIGS. 24A and 24B show side and cross-sectional side views of yet another variation in which in which a tapered body 111 formed separately from the body segment 109 may similarly be secured to the suture terminal end and attached to the body segment 109 as well (e.g., via mechanical attachment, welding, bonding, etc.).

Figure 25A:
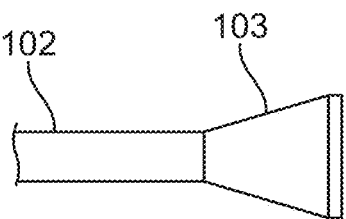
FIGS. 25A and 25B illustrate side views of a variation of the suture terminal end which may be configured to have a widened portion.
Figure 25B:
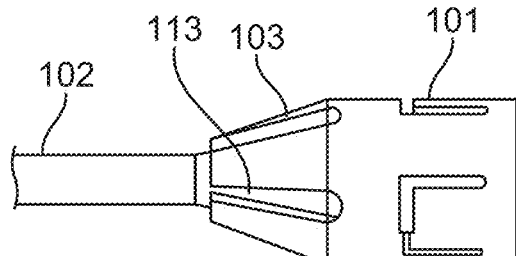
Figure 26A:
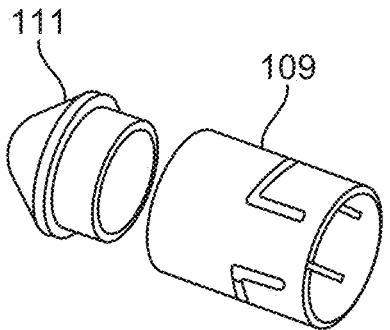
FIGS. 26A and 26B show perspective views of the coupling member to illustrate how the tapered body may be attached via one or more welded spots to the body segment.
Figure 26B:
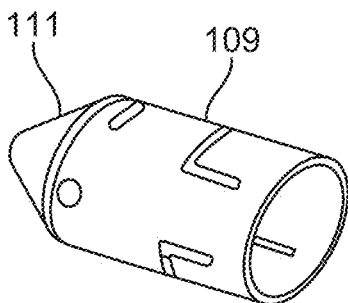

In another variation, FIGS. 25A and 25B illustrate side views of a variation of the suture terminal end which may be configured to have a widened portion 113, e.g., a melted, knotted, or heated portion, or an additional mechanical feature. This widened portion 113 may be inserted within the coupling member to enhance the secure engagement to the coupling member. FIGS. 26A and 26B show perspective views of the variation of the coupling member from FIGS. 24A and 24B to illustrate how the tapered body 111 may be attached via one or more welded spots to the body segment 109.

To illustrate how the suture lengths may be delivered during suture deployment into the tissue, FIGS. 27A-27E show schematic illustrations to demonstrate steps involved with the suture deployment. A single suture length 102 is shown for clarity purposes, however, a second suture length may be deployed in parallel from the second pair of needle members to create a parallel stitch or cross-stitch pattern, as described herein, or any other pattern as desired. Furthermore, an alternative number of needle members may be used, as further described herein.

Figures 27A, 27B, 27C:
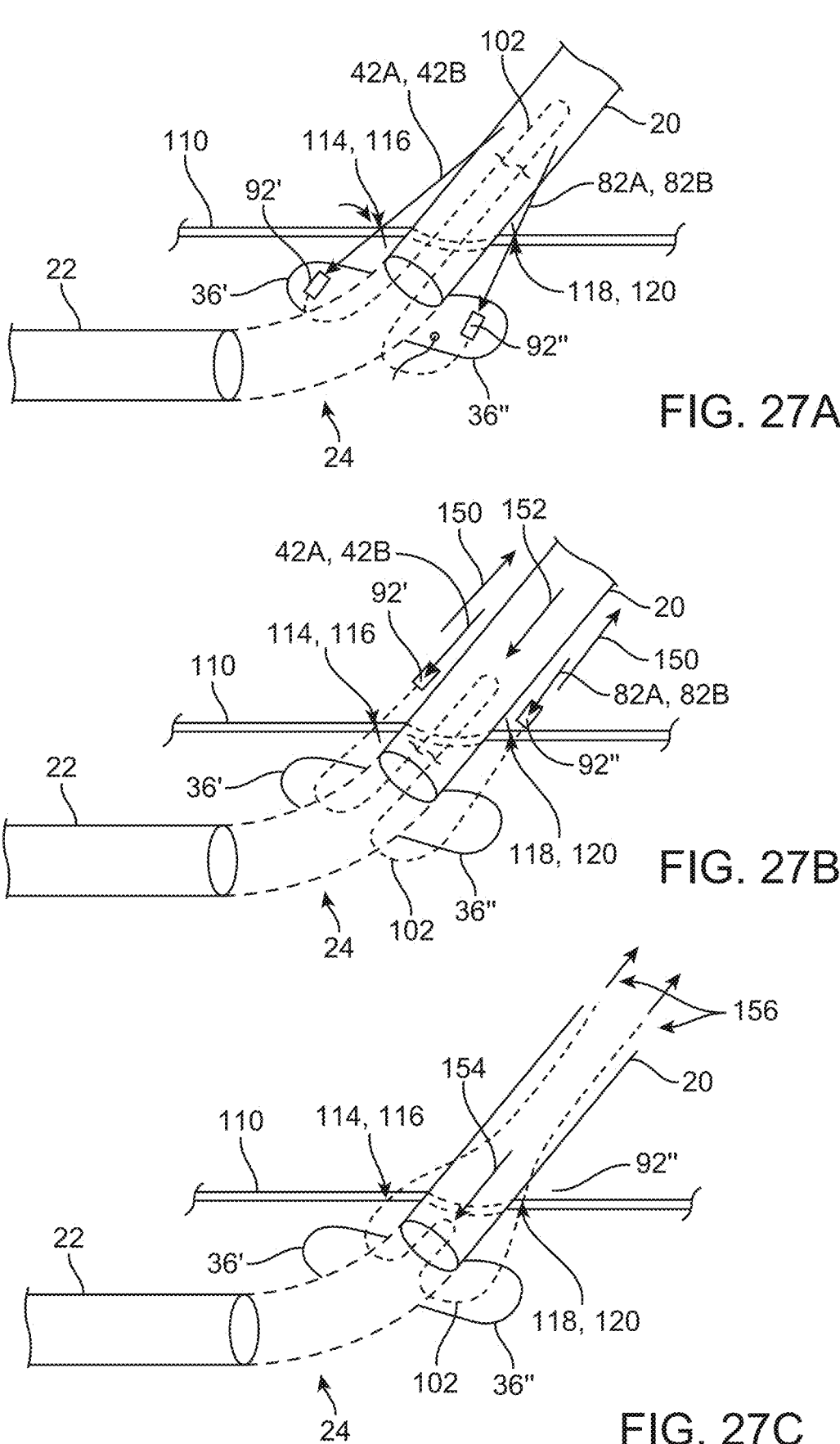
FIGS. 27A-27E show schematic illustrations to demonstrate steps involved with the suture deployment from a proximally routed device position.

As shown in the illustrative side view of FIG. 27A, after the distal catheter segment 22 has been introduced through the puncture site and positioned at an angle into the vessel 110 relative to the proximal catheter segment 20, the receiver member may be actuated to rotate from its low-profile configuration into its deployed configuration as shown, e.g., by actuation of the first actuation mechanism 14. With the receiver member deployed, it may be pulled against the vessel inner wall adjacent to the puncture site and the forward needle members 42A, 42B and rear needle members 82A, 82B may be advanced from the proximal catheter segment 20 so that their respective piercing tips are passed through the tissue adjacent to the puncture site each through their own entry points 114, 116 and 118, 120, e.g., by depressing the second actuation mechanism 16.

The bite margin between the outer surface of the device and the entry points 114, 116 and 118, 120 may be seen and the piercing tips of each needle member are advanced until they are received in their respective openings, the forward needle members 42A, 42B received in their respective coupling members within the first receiver portion 36' and the rear needle members 82A, 82B received in their respective coupling members within the second receiver portion 36". The suture length 102 may be seen in this variation as pre-loaded within a lumen or space within the proximal catheter segment 20.

With the piercing tips engaged to the respective coupling members, each of the needle members may be pulled proximally away from the receiver member such that the coupling members are pulled from their respective receiver portions 36', 36", as shown in FIG. 27B, e.g., by pulling of the second actuation member 16. Each of the needle members along with the engaged coupling members are pulled proximally through the entry points 114, 116 and 118, 120 (as denoted by directional arrows 150) and externally of the vessel 110 such that the attached terminal ends of the suture length 102 are pulled through the receiver member portions 36', 36" and through the entry points 114, 116 and 118, 120 as well.

Figure 27D:
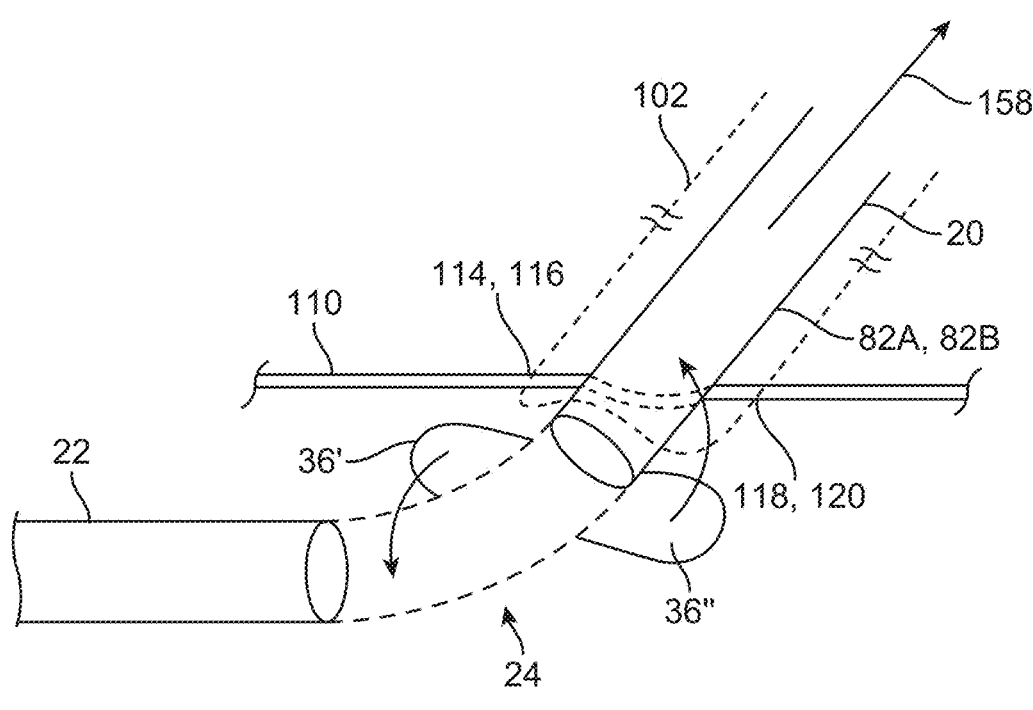
Figure 27E:
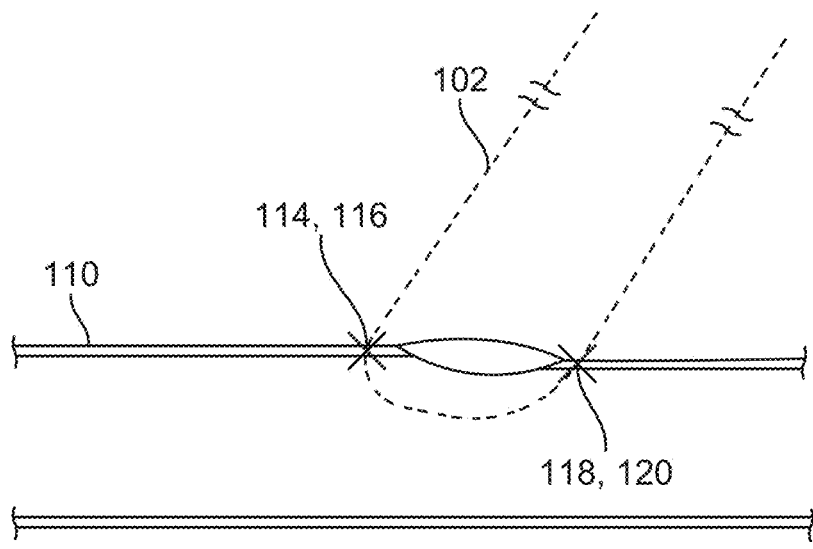

As the suture length 102 is continued to be tensioned proximally 156, the suture length 102 stored within the proximal catheter segment 20 (and/or distal catheter segment 22 in other variations) may be pulled out from the storage lumen or space 104 until the final remainder of the suture 154 is pulled down into the vessel 110, as shown in FIG. 14C, until the suture 102 is free of the device 10. With the terminal ends of the suture length 102 located externally of the vessel 110 and the patient, the terminal ends may be cut or trimmed from the coupling members to release the suture length 102 from the needle members to which the coupling members are engaged. The receiver member may then be rotated back into its low-profile configuration, as shown in FIG. 27D, and the device 10 may be pulled 158 proximally back through the puncture site leaving just the suture length 102 passed through the entry points 114, 116 and 118, 120, as shown in FIG. 27E.

The proximal ends of the suture length 102 may be tensioned from outside the patient body such that the edges of the puncture site are approximated towards one another along the vessel wall. With the puncture site closed by the suture length 102, the suture may be tightened and secured relative to one another to maintain hemostasis of the puncture site. A second instrument for suture capture and securement may then be used to secure the ends of each suture length, as described in further detail herein.

As the suture lengths are pulled out from the suture storage lumen or space 104 within the proximal catheter segment 20 and/or distal catheter segment 22, various mechanism may be utilized to release the suture in a controlled manner in order to prevent premature suture release and potential entanglement.

Figure 28:
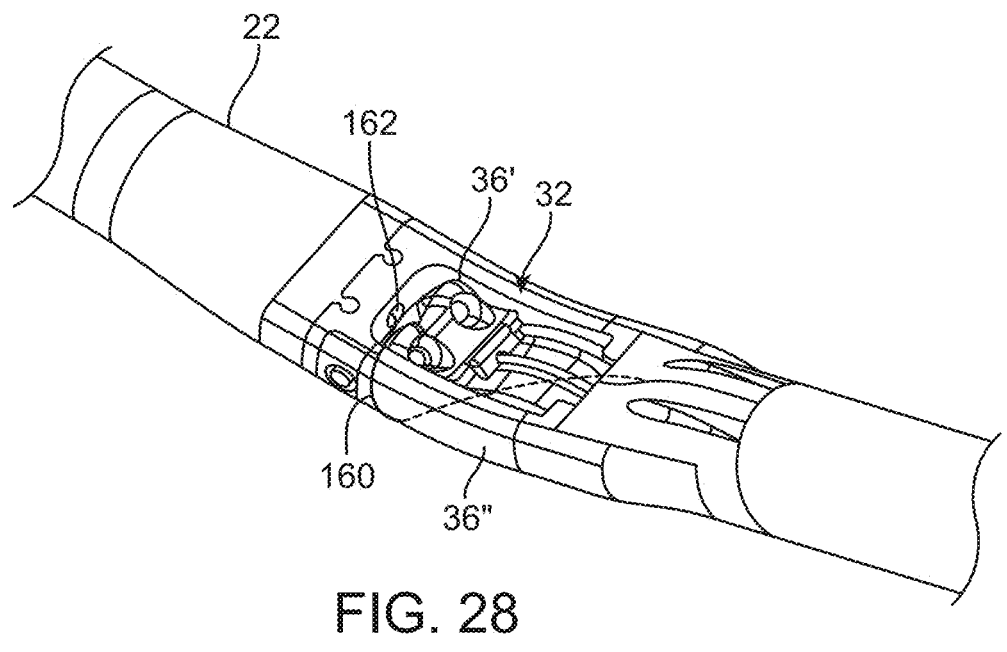
FIG. 28 shows a detail perspective view of the proximal catheter segment having an opening through which the suture may pass through into the suture lumen or space.
Figures 29A, 29B:
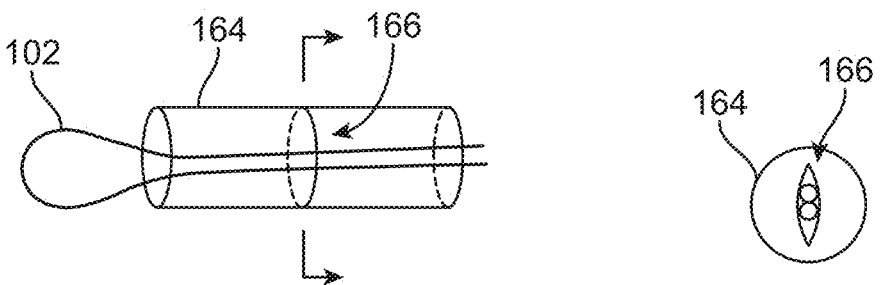
FIGS. 29A and 29B show perspective and end views of a suture lumen feature involving an elastomeric component which may impart a squeezing force or friction on the through routed suture

One such mechanism is shown in the perspective detail view of FIG. 28 which illustrates the proximal catheter segment 22 having an opening 162 through which the suture 160 (shown in a cross-stitch variation of FIG. 15) may pass through a distal lumen on the center axis of the proximal device segment. The suture lumen described herein and shown as lumen 164 may incorporate a friction feature 166 such as a narrowed segment or passageway using a material such as silicone, as shown in the perspective and end views of FIGS. 29A-29B, which may apply a light tension upon the suture 102 such that the suture is prevented from spooling externally of the device in an uncontrolled manner during deployment. The friction feature 166 may be used with the suture lumen or space in either the proximal catheter segment 20, distal catheter segment 22, or any other suture lumen for suture management.

Figure 29C:
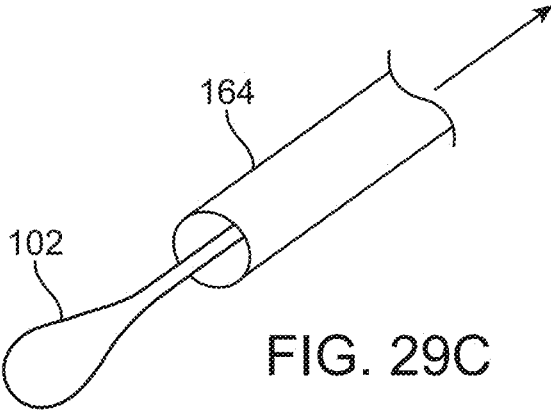
FIG. 29C shows a perspective detail view of a suture lumen that may be terminated to open into a larger space where the remainder of the suture length may be stored and an elastomeric appropriately sized tube for gripping the suture in the loaded configuration.

Another variation is shown in the perspective detail view of FIG. 29C where the suture lumen 164 may be terminated to open into a larger space where the remainder of the suture length 102 may be stored. The length of the suture lumen 164 itself may be varied to alter the amount of friction applied to the suture length 102. The length of suture maintained externally of the suture lumen 164 may provide some nominal resistance to the suture 102 from being pulled out prematurely.

FIGS. 30A and 30B show top and cross-sectional top views of another variation of the distal catheter segment 22 having one or more friction inducing features incorporated along the segment 22 for imparting a frictional grip or resistance upon the suture housed within the distal catheter segment 22. In this variation, with the suture lengths routed through their respective suture channels 106 and/or 108 (as described herein), they may be in contact with one or more suture tensioning members 161 which are positioned within respective channels or grooves 163 to create tensioning points 159 between the suture length and the tensioning members 161 in order to impart a frictional contact upon the suture. The frictional grip may ensure that the underlying suture lengths remain secure during transport and storage. However, when the device is in use, the suture lengths may be withdrawn to pass through the suture channels 106 and/or 108 while the tensioning members 161 ensure that the suture lengths are deployed in a controlled manner.

The variation shown illustrates two tensioning members 161 configured as O-rings which are separated from one another along the length of the distal catheter segment 22. The tensioning members 161 may be separated from one another over a range of distances, e.g., 0-2.5 cm. Furthermore, a single tensioning member 161 may be used to more than two tensioning members 161 may instead be employed. Additionally, while the tensioning members 161 are illustrated as O-rings, other features may instead be used, e.g., C-shaped clamps, partial rings, etc.

The cross-sectional shapes of the tensioning members 161 may also be varied in any number of configurations so long as they provide suitable contact with the underlying suture. FIG. 31A shows a tensioning member 165 having a polygonal cross-section 165. FIG. 31B shows tensioning member 167 having a circular cross-section 165, and FIG. 31C shows tensioning member 169 having a rectangular or square cross-section 165. The material of the tensioning member may also be varied, e.g., elastomeric materials such as nitriles, silicone, etc.

Figure 32A:
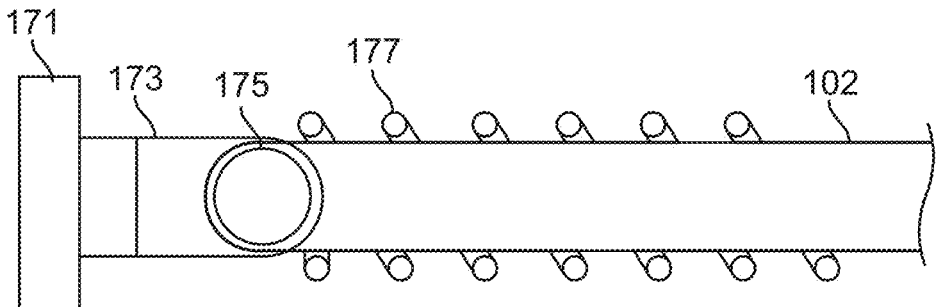
FIGS. 32A and 32B illustrate in the detail schematic side and perspective views another variation of a suture tensioning mechanism which also be positioned within the distal catheter segment to remove suture slack.
Figure 32B:
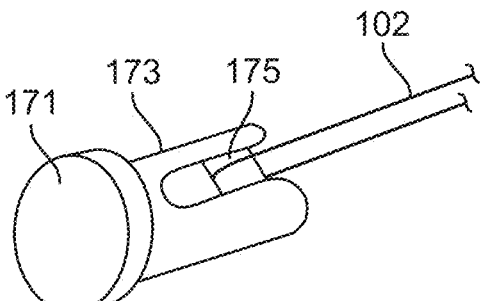

In another variation, a flange pull rod may be incorporated within the distal catheter segment 22 to impart a tension upon the suture contained within the lumen or space 104' to remove any suture slack unfurled during use. The suture may be wound one or more times around the flange pull rod which may be designed to break or fail at a specific load expected during suture withdrawal during a tissue closure procedure. In yet another suture tensioning mechanism, FIGS. 32A and 32B illustrate in the detail schematic side and perspective views another variation of a suture tensioning mechanism which also be positioned within the distal catheter segment 22 to remove suture slack. The suture 102 may be looped around a post 175 extending between two support members 173 attached to a flanged body 171. A spring or biasing element 177 may provide a tensioning force upon the flanged body 171 such that the suture 102 length remains under a tension by the post 175 pulling upon the suture 102.

Figure 32C:
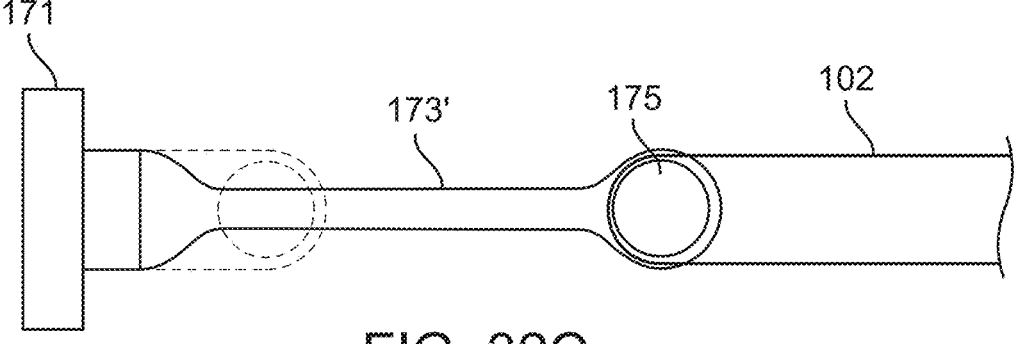
FIG. 32C shows a schematic side view of yet another variation in which the flanged body may instead incorporate one or more elastomeric support members which are configured to provide tension upon the suture looped around the post.

In other variations, the spring or biasing element 177 may be omitted entirely and the post 175 with flanged body 171 may be used alone to provide the tensioning force, as shown in FIG. 32B. FIG. 32C shows a schematic side view of yet another variation in which the flanged body 171 may instead incorporate one or more elastomeric support members 173' which are configured to provide tension upon the suture 102 looped around the post 175 by the elastomeric properties of the support members 173', which are illustrated in a stretched or elongated configuration when tension is imparted by the suture 102. The post 175 and/or support members 173' may preferentially fail once a threshold tension has been reached.

Any of these suture delivery variations may be used in any number of combinations or embodiments together with any of the device features described herein including any of the receiver and needle deployment, suture management, tissue management, alternative device embodiments, or suture capture and securement features described herein.

Tissue Management

As described herein, the tissue surrounding the puncture site may be configured into an oval or elliptical configuration to maintain or increase the bite margin along the tissue between the needle members and the catheter exterior in larger arteriotomy or venotomy sizes (i.e., 10 Fr or more and 20 Fr or more depending on the device size used). While the puncture site may be configured by the angling of the device relative to the vessel, additional features may be optionally incorporated to further increase or facilitate the tissue reconfiguration, particularly for puncture sites which may be particularly large relative to the device transition diameter.

One or more lateral dilator elements may be configured to extend from the exterior of the proximal catheter segment 20 and/or distal catheter segment 22 and/or support structure 30 as well in order to force the edges of the puncture site along the sides of the device 10 away from one another such that the edges of the puncture site forward and rear of the device 10 along the vessel are urged towards one another. These lateral dilator elements may be configured to extend when actuated by a mechanism located, for example, upon the handle 12.

FIG. 33A schematically illustrates an example where a push/pull member 170 (such as push/pull member 84 described herein) may incorporate an expansion member 176 such as a tapered or conically shaped feature which is attached along the push/pull member 170. The push/pull member 170 may be actuated to deploy the receiver member, as previously described, and it may also move the expansion member 176 to be received within a receiving channel 174 defined by one or more dilation arms 172 which are separatable from one another. As the push/pull member 170 is tensioned or pulled, the proximal movement of the expansion member 176 may force the dilation arms 172 to actuate and move away from one another such that the dilation arms 172 extend away from the exterior surface of the catheter segment or support structure to contact and push the adjacent tissue. As the push/pull member 170 is tensioned or pulled, the proximal movement of the expansion member 176 may be configured such that the movement of the expansion member 176 occurs simultaneously or in a staged fashion relative to the receiver XX movement.

FIG. 33B illustrates one variation where the dilation arms 178', 178" are positioned on opposite sides of one another along the distal end of the proximal catheter segment 20. When actuated, the arms 178', 178" may move distally, for example, along fixed, curved tracks or guides which may urge the arms 178', 178" to advance radially away from the exterior surface of the device. The contacted tissue may be forced away from the sides of the device 10 to urge the remaining areas of the tissue edges into an oval or elliptical configuration.

FIG. 33C illustrates another variation where the dilation arms 180', 180" may be formed into a ribbon-like configuration in which the arms 180', 180" may bend or pivot about respective fixed pivot points 182', 182" when compressed distally, as shown.

FIG. 33D shows yet another variation where the dilation arms 184', 184" may be formed of members which are pushed out orthogonally or transversely when actuated.

Any of these tissue management variations may be used in any number of combinations or embodiments together with any of the device features described herein including any of the receiver and needle deployment, suture management, suture delivery, alternative device embodiments, or suture capture and securement features described herein.

Alternative Device Embodiments

Figure 34A:
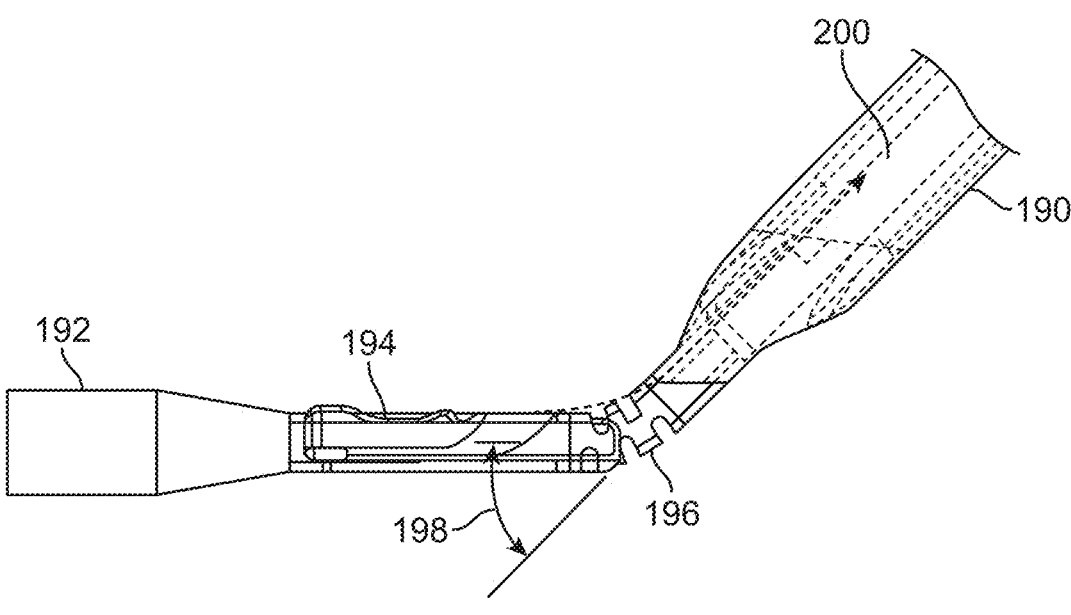
FIGS. 34A and 34B show detail side views of another variation of a device having a proximal catheter segment and distal catheter segment coupled to one another via a flexible segment.
Figure 34B:
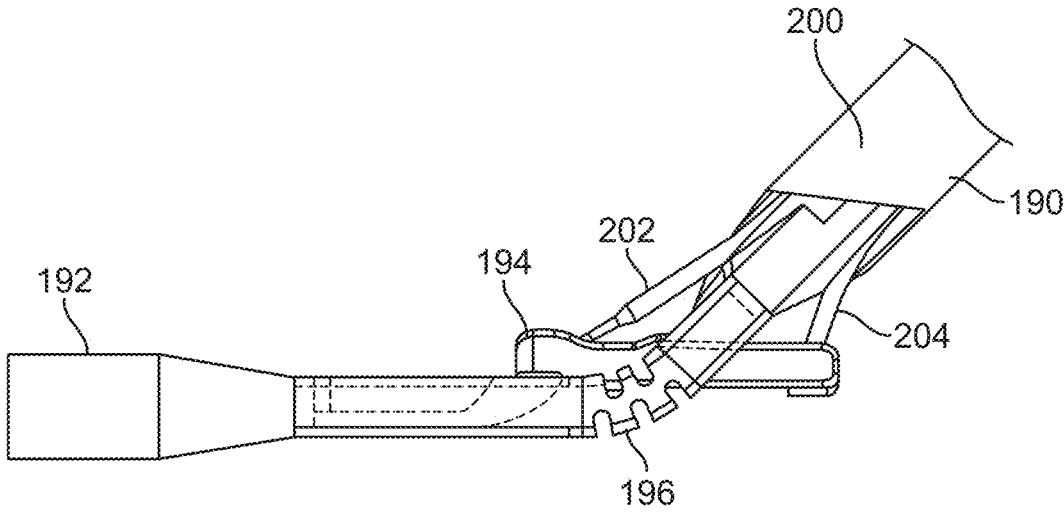

Aside from the device variations described herein, additional variations may be implemented. FIGS. 34A and 34B show detail side views of one such variation having a proximal catheter segment 190 and distal catheter segment 192 which is coupled to one another via a flexible segment 196 which allows for the rotation of the proximal catheter segment 190 at an angle 198 relative to the distal catheter segment 192. The receiver member 194 may be positioned in its low-profile configuration within an extension of the distal catheter segment 192. Rather than rotating into its deployed configuration, the receiver member 194 may be pulled proximally from the distal catheter segment 192 to become exposed and aligned into position via an actuation member 200 such as a push/pull rod slidingly positioned through the proximal catheter segment 190.

After the receiver member 194 has been positioned into its deployed position, the forward and rear needle members 202, 204 may be deployed from proximal catheter segment 190 and into contact with the corresponding openings along receiver member 194.

Figure 35A:
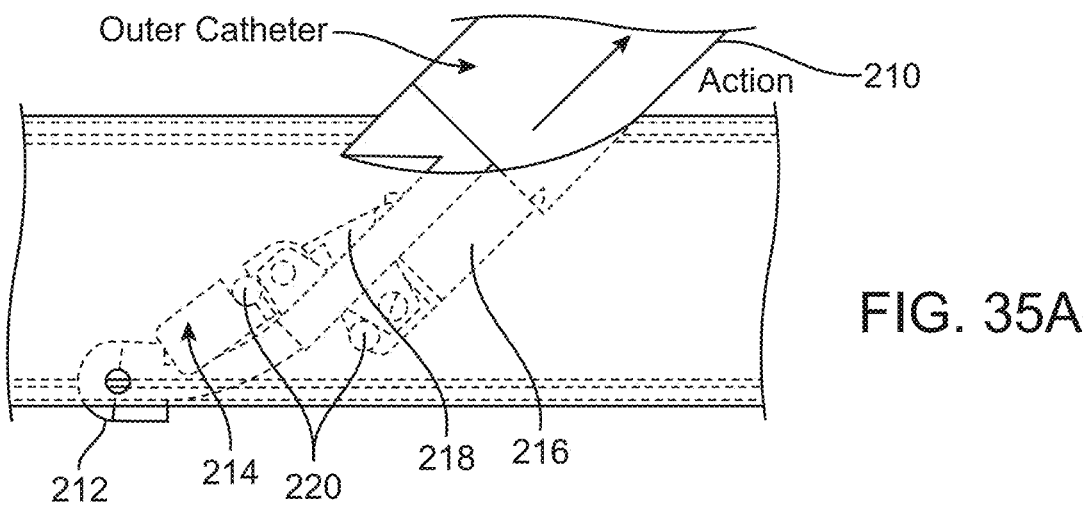
FIGS. 35A-35D show side and perspective views of yet another variation where the device may omit the distal catheter segment and instead incorporates a central shaft.
Figure 35B:
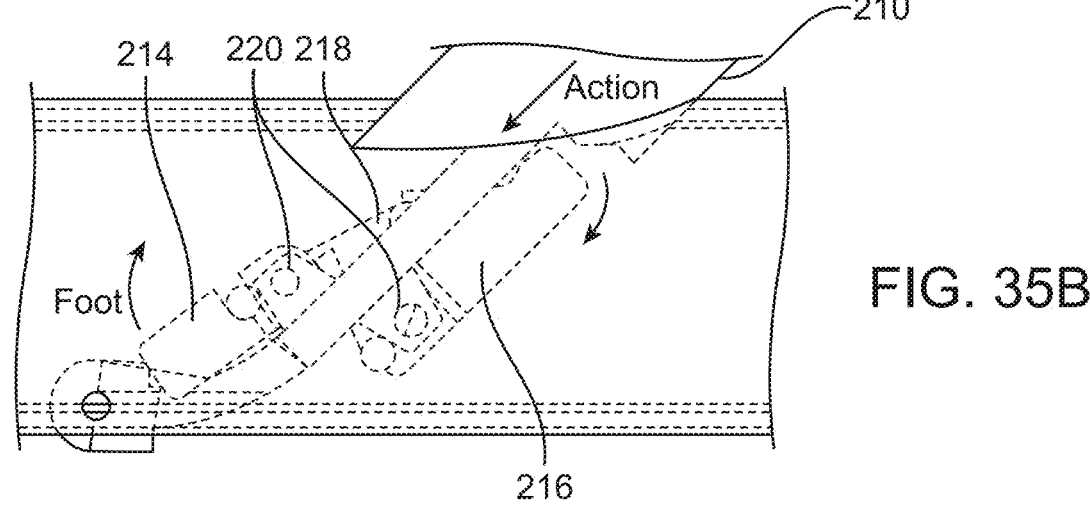
Figure 35C:
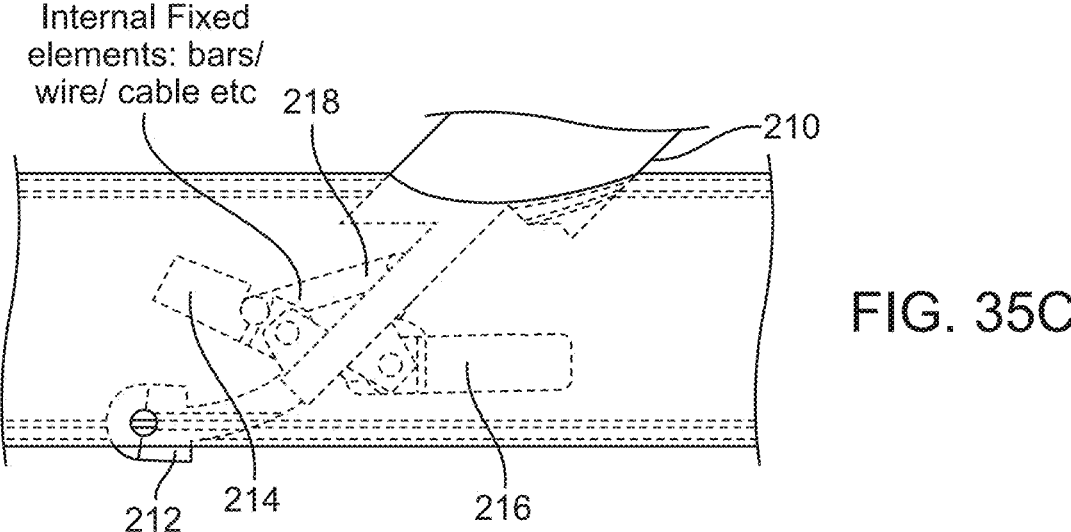
Figure 35D:
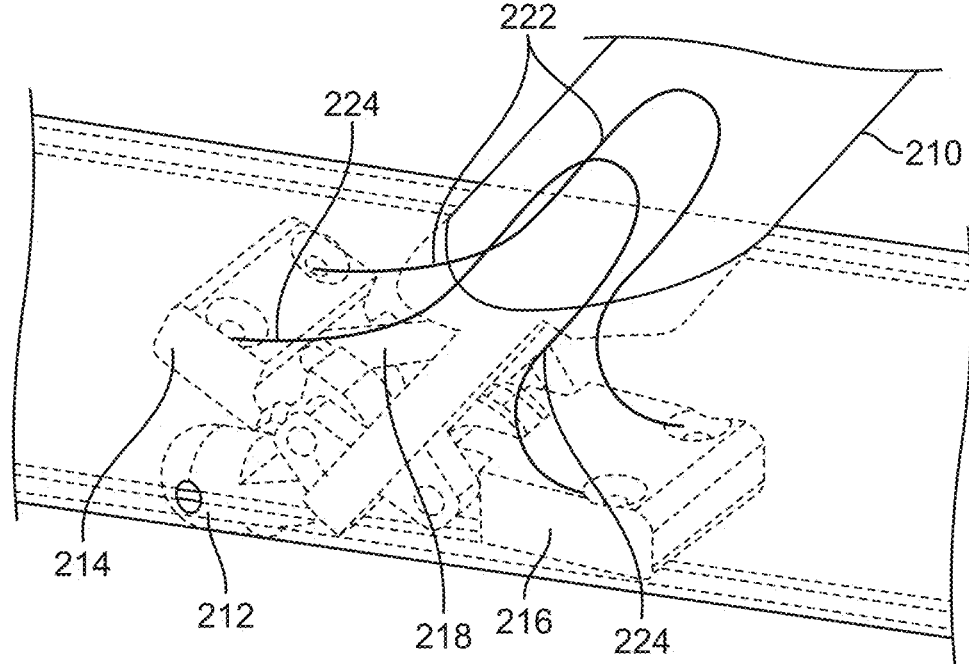

FIGS. 35A-35D show side and perspective views of yet another variation where the device may omit the distal catheter segment. Instead, a central shaft 212 may be slidingly positioned through a proximal catheter segment 210. The central shaft 212 may include a first receiver portion 214 and a second receiver portion 216 opposite to the first receiver portion 214 where each receiver portion may be rotationally coupled via a hinged or pinned connection 220 to an internal fixed element 218. As the central shaft 212 is introduced and advanced into the vessel, the first and second receiver portions 214, 216 may be maintained in a low-profile configuration, as shown in FIG. 35A, and when the central shaft 212 has been appropriately positioned, the internal fixed element 218 may be pushed, pulled, rotated, or otherwise actuated to rotate both the first and second receiver portions 214, 216 into their deployed configuration, as shown in the FIGS. 35B and 35C. The internal fixed element 218 is illustrated as having bar connections, but other variations may include cables, wires, or other attachment features. FIG. 35D shows a perspective view where the first and second receiver portions 214, 216 have been deployed where each opposed coupling member within each opening may have its own suture loops 222, 224, as described herein.

FIGS. 36A-36B and 37A-37B illustrate various perspective views of yet another variation of the device. In this variation, the proximal catheter portion 230 may similarly include a central shaft 232 which incorporates a fixed ramp portion 234 which presents an angled or tapered surface. When actuated, a first receiver portion 236 may be urged distally or the central shaft 232 may be urged proximally such that the first receiver portion 236 is forced to move up and away from the central shaft 232 as it contacts and slides upon the ramp portion 234 and rotates about a hinged coupling 238, as shown in FIGS. 36A and 36B. Simultaneously, the second receiver portion 240 may be urged to rotate about a hinged coupling 242 when pushed or urged by a pin element 243, as shown in the corresponding FIGS. 37A and 37B.

Figure 38A:
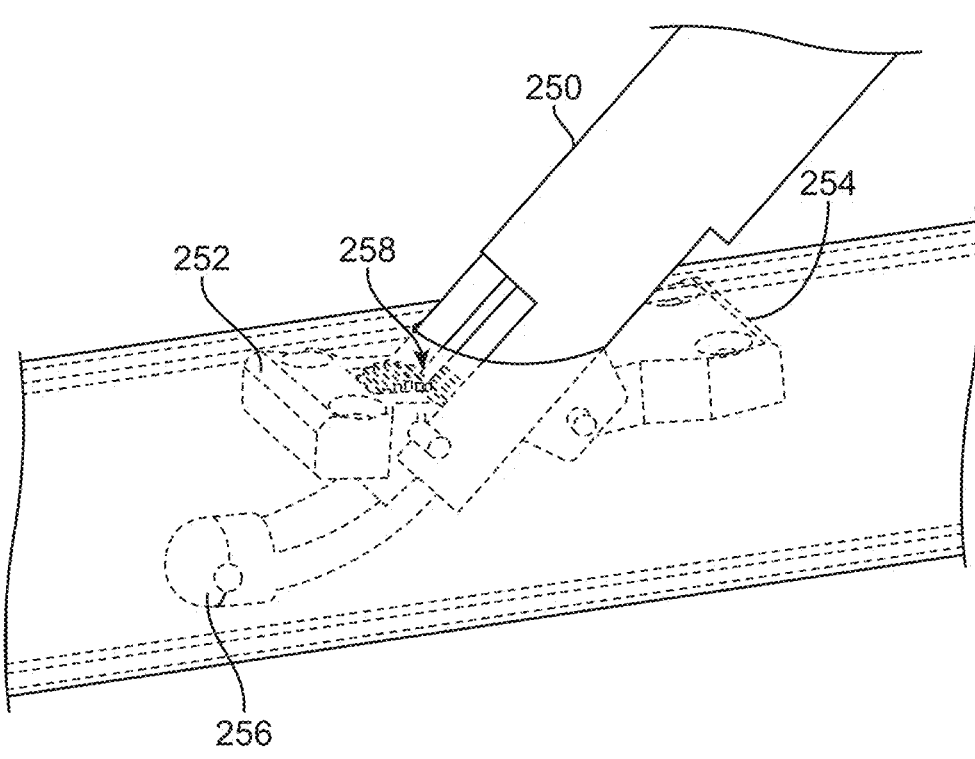
FIGS. 38A and 38B show perspective views of yet another variation of the device which incorporates a dual receiver feature actuated or rotated via a ratcheting mechanism such as a rack-and-pinion mechanism.
Figure 38B:
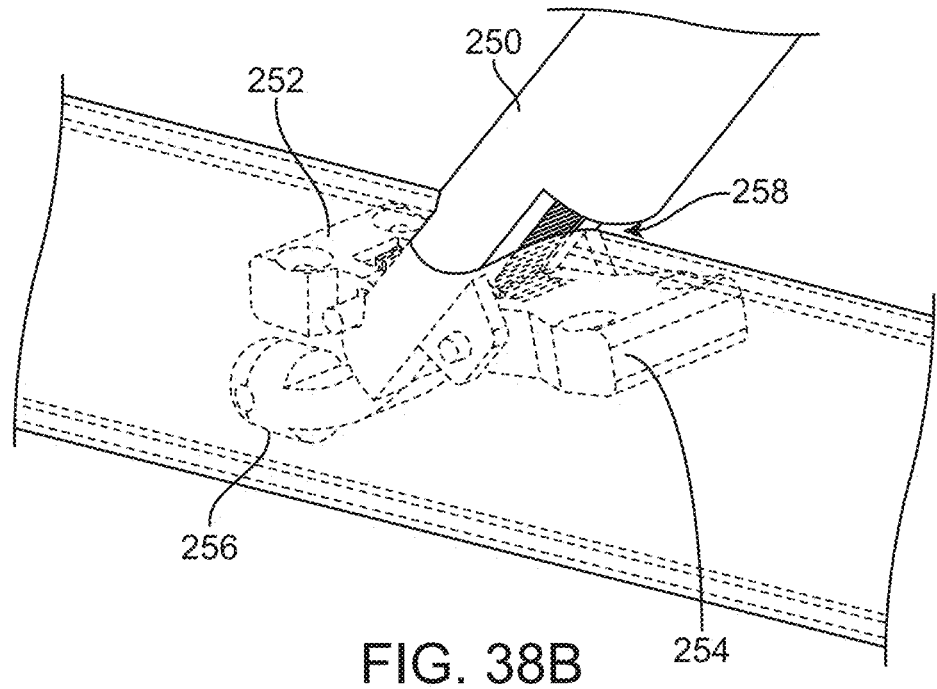

FIGS. 38A-38B show various perspective views of yet another variation of the device which incorporates a dual receiver feature which may be actuated or rotated via a ratcheting mechanism such as a rack-and-pinion mechanism. This variation may similarly incorporate a central shaft 256 having a first receiver portion 252 and a second opposed receiver portion 254 each rotatingly coupled to the proximal catheter segment 250. The central shaft 256 may define a number of projections (e.g., such as a rack configuration) on both sides facing each respective receiver portion 252, 254 which may also incorporate a circular pinion configuration. Once the central shaft 256 has been suitably advanced and positioned within the vessel, the central shaft 256 may be pulled proximally to actuate the rack-and-pinion engagement with the receiver portion 252, 254 such that the receiver portion 252, 254 are rotated in their deployed configurations.

Any of these alternative device variations may be used in any number of combinations or embodiments together with any of the device features described herein including any of the receiver and needle deployment, suture management, suture delivery, tissue management, or suture capture and securement features described herein.

Suture Capture and Securement

As described herein, a second instrument for suture capture and securement may be used to secure the ends of each suture length after deployment and delivery through the tissue region to be closed for hemostasis using the devices described above.

Figure 39A:
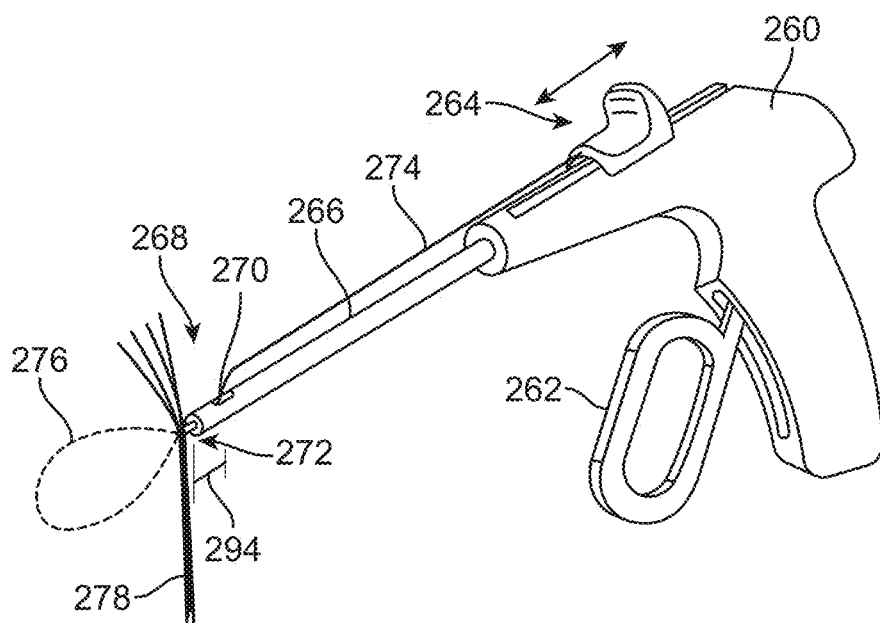
FIG. 39A shows one variation of a suture capture and securement device.

One variation of a suture capture and securement device is shown in the perspective view of FIG. 39A which illustrates a handle 260 having an actuation mechanism 262 for deploying or securing an anchor to the captured sutures. An elongate shaft 266 may extend from the handle 260 and terminate in an opening 268 at its distal tip. The opening 268 may extend partially through the shaft 266 and to a window 270 which is defined along a side of the shaft 266 in proximity to the distal tip. The window 270 may be set proximally from the distal tip of the shaft 266 by a distance 294 which may be measured from the distal tip to a center of the window 270 where the distance 294 may range anywhere from, e.g., 0.5 cm to 5 cm. A securement anchor 272 such as a ferrule having a lumen therethrough may be positioned within the opening 268. A slide element 264 may be detachably positioned along the shaft 266 or along the handle 260 and a wire 274 may be coupled to the slide element 264 and extend along the device and pass into the window 270, through the securement anchor 272, and distally through the opening 268 where the wire 274 may form a snare loop 276 which opens into an expanded loop for engaging suture.

The wire 274 and suture snare loop 276 may be formed of any number of materials such as stainless steel, nitinol, nylon, thermoplastics, sutures, etc in any number of configuration formats such as braided, cabled or single filament, etc. Furthermore, the securement anchor 272 contained within the distal opening may be positioned within the distal tip at a distance of, e.g., 3 mm or less, from the outer surface of the distal tip.

Figure 39B:
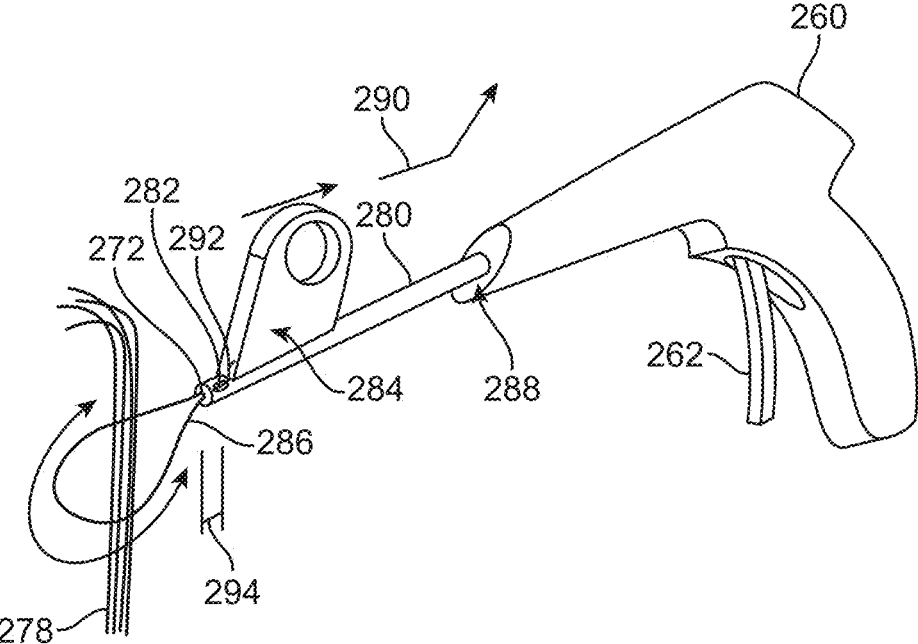
FIG. 39B shows another variation of a suture capture and securement device.

Another variation of the suture capture and securement device is shown in the perspective view of FIG. 39B which shows handle 260 having an actuation mechanism 262 and an elongate shaft 280 extend from the handle 260. In this variation, the suture snare slide element 284 may reside near the distal end of the shaft 280 proximal to the window 282 defined along the side of the shaft 280. As above, the window 282 may be set proximally from the distal tip of the shaft 280 by a distance 294 which may be measured from the distal tip to a center of the window 282 where the distance 294 may range anywhere from, e.g., 0.5 cm to 3.5 cm. The window 282 itself may be sized suitably to accommodate the passage of up to eight lengths of suture (e.g., four terminal suture ends 278 which are folded upon themselves as they are pulled proximally through the window 282) where the length of the window 282 along the length of the shaft 280 may range anywhere from, e.g., 2 mm to 10 mm, and the width of the window 282 transverse to the length of the shaft 280 may range anywhere from, e.g., 1 mm to 4 mm. The suture snare slide element 284 may be formed as a projection or tab such as a ring-tab which provides a feature which is readily grasped with a single hand and pulled. The wire 292 may be attached to a distal portion of the suture snare slide element 284 and extend distally through the window 282, through the securement anchor 272 retained within, and distally out through the opening where the wire 292 may form a suture snare loop 286. The suture snare slide element 284 and elongate shaft 280 may both have features to hold the two elements in a desired relative position to one another. Such features may also facilitate a removably secure connection between the two components until the point of use.

In use, the terminal suture ends 278 which remain after the delivery of the suture around the puncture site may each be passed through the suture snare loop 286. The suture snare slide element 284 may then be pulled proximally 290 off or along the elongate shaft 280 such that the wire 292 is pulled through the window 282 and securement anchor 272 such that the suture snare loop 286 tightens around the suture ends 278. As the suture snare slide element 284 is pulled further proximally, it may abut a tapered interface surface 288 defined along the distal end of the handle 260 such that the suture snare slide element 284 is urged up and disengaged away from the elongate shaft 280.

Prior to a suture capture and securement procedure, the suture snare slide element 284 and suture snare loop 286 may be preloaded upon the elongate shaft 280 so the suture capture and securement device may be available for use immediately. In the event that additional securement anchors 272 may be needed for tissue closure, multiple suture capture and securement devices may be used or additional suture snare slide elements 284, suture snare loops 286, and securement anchors 272 may be loaded upon the same elongate shaft 280 as many times as needed for deployment of additional securement anchors 272.

Figure 40A:
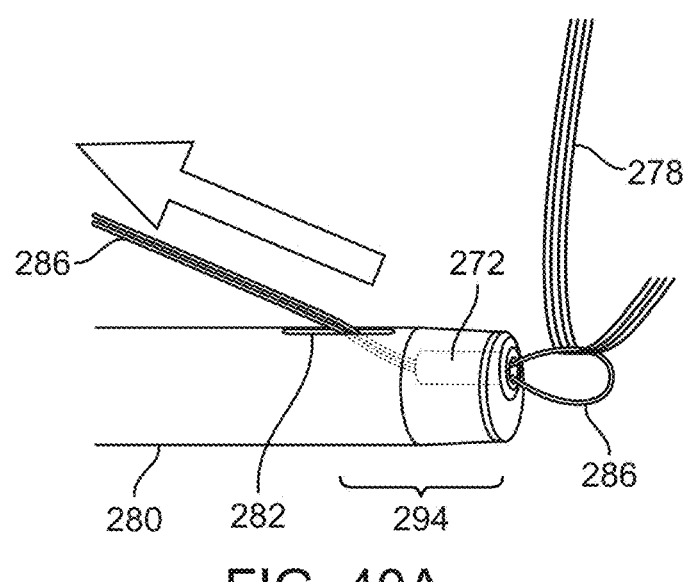
FIGS. 40A-40C show detailed perspective views of the suture ends being engaged by the suture exchange snare loop.
Figure 40B:
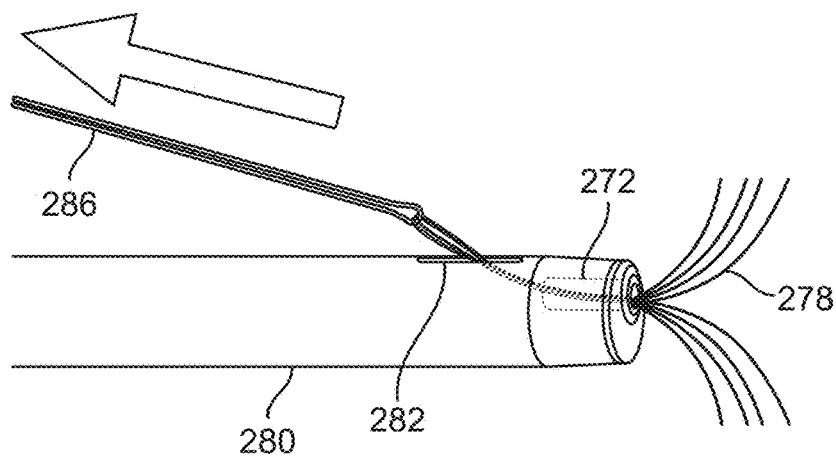
Figure 40C:
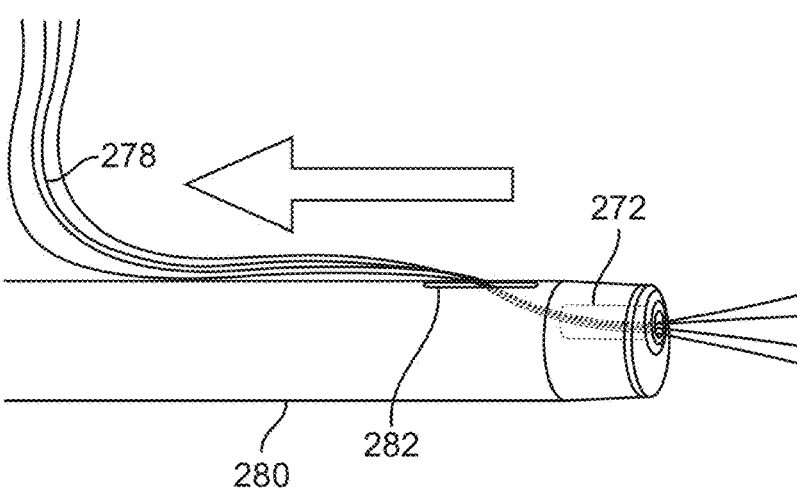

FIGS. 40A-40C illustrate detailed perspective views of the suture ends 278 being engaged by the suture snare loop 286, as shown in FIG. 40A. As the suture snare loop 286 is further pulled proximally through the securement anchor 272 and window 282, the ensnared suture ends 278 may be pulled through accordingly, as shown in FIG. 40B, until the suture ends 278 pass entirely through both the securement anchor 272 and window 282, as shown in FIG. 40C.

Figure 41A:
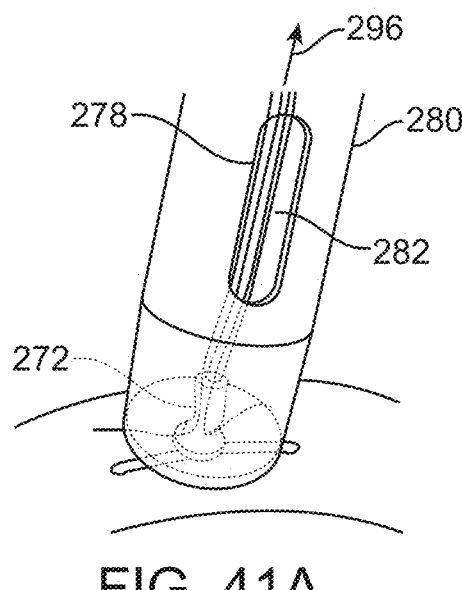
FIGS. 41A-41C show detailed perspective views of the suture ends being secured and trimmed.
Figure 41B:
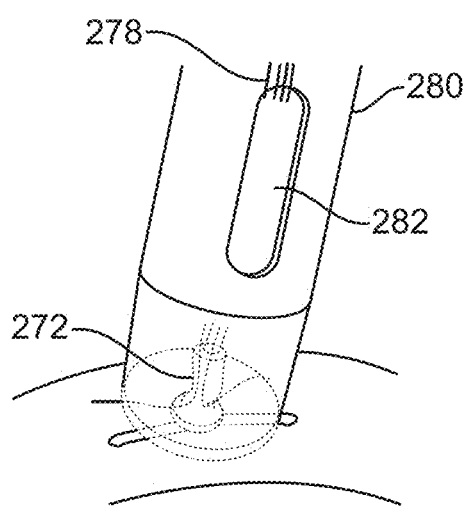
Figure 41C:
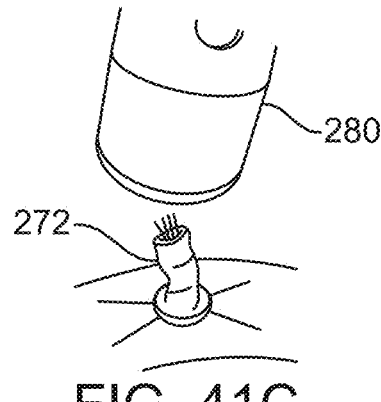

The suture ends 278 may be tensioned proximally as the distal tip of the shaft 280 is distally advanced to the puncture site while tightening the sutures engaged through the tissue until the edges of the puncture site are approximated or closed, as shown in FIG. 41A. Once the puncture site is tensioned closed, pulling proximal tension on the sutures, as denoted by arrow 296, allows the user to assess hemostasis prior to finalizing suture securement and trimming. Once hemostasis has been assessed, the securement anchor 272 may be deformed, crimped, or otherwise tightened to secure the suture 278 passing through until movement of the securement anchor 272 is no longer possible, e.g., by triggering the actuation mechanism 262 on handle 260 to actuate a clamping mechanism within the distal end of the shaft 280 to deform or crimp the securement anchor 272 about the suture. With the securement anchor 272 crimped or tightened, the suture ends 278 may be cut or trimmed, as shown in FIG. 41B, and the shaft 280 may be removed leaving the securement anchor 272 and trimmed suture with hemostasis achieved, as shown in FIG. 41C. In some embodiments, the suture ends can be trimmed in tandem with attachment of the securement anchor 272 by way of a built-in cutter driven by the same actuation mechanism 262. Trimming of the suture may be conducted such that the tails of suture emanating proximally from the ferrule component are cut flush or to a desired length, e.g., 0-30 mm or more in length above the end of the securement anchor 272. As illustrated in FIG. 41C, two (or more) suture lengths or loops are secured with a single securement anchor in contrast to one knot being required for each suture length.

Figure 42A:
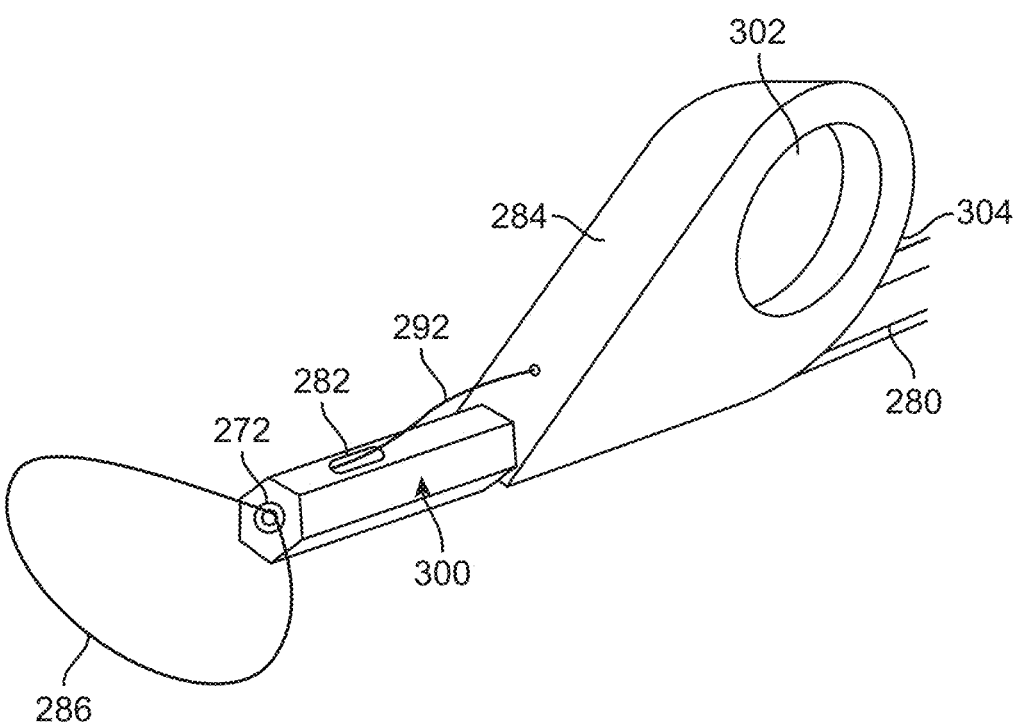
FIGS. 42A and 42B show detail perspective and side views of the suture exchange snare slide element.
Figure 42B:
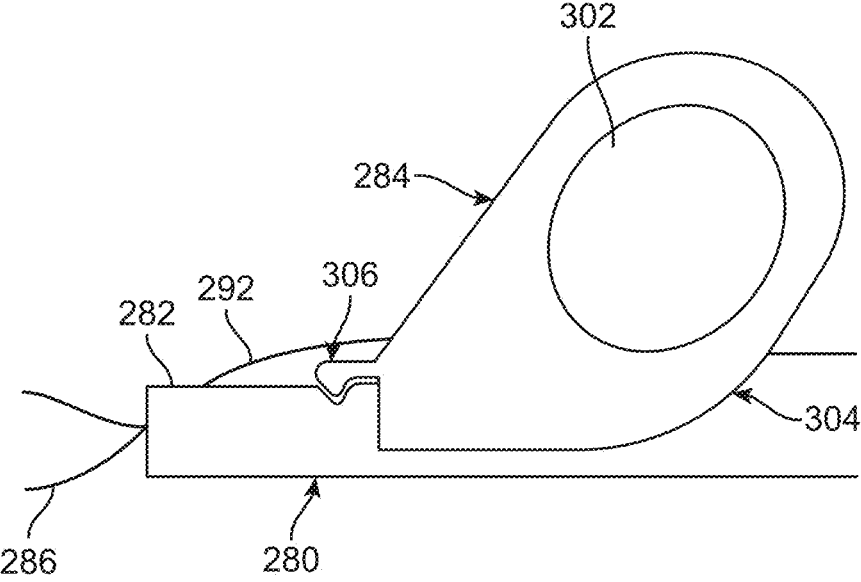

FIGS. 42A and 42B show detail perspective and side views of the suture snare slide element 284 to illustrate additional features which may be incorporated. Slide element 284 is shown to define a ring-tab 302 which allows for a user to grasp the suture snare slide element 284 with a single finger or hand. The wire 292 may be seen attached to a distal portion of the slide element 284 such that it extends distally into the window 282, through the securement anchor 272 contained within the distal opening at the end of shaft 280, and out the distal opening to form the snare loop 286. The suture snare slide element 284 defines an open channel through which the shaft 280 is slidingly engaged such that the slide element 284 may translate proximally upon the exterior of shaft 280 and is removably secure. The shaft 280 may be configured to have a cross-sectional profile which is keyed or angled to ensure that the slide element 284 may remain aligned and or clocked relative to the elongate shaft during proximal translation. In this variation, the shaft 280 is shown to have a hexagonally shaped exterior profile 300 along the length of the shaft 280 although the shaft exterior 300 may be configured to have any number of different cross-sectional areas (e.g., triangle, square, rectangle, pentagon, etc.) so long as they facilitate the alignment of the slide element 284 upon the shaft 280. Rather than a keyed cross-sectional surface, the shaft 280 may alternatively incorporate a guide or rail or longitudinal projection which is keyed to a corresponding receiving channel along the slide element 284. Such a longitudinal projection may also function to ensure alignment of the slide element 284 relative to the shaft 280 during proximal translation of the slide element 284.

The proximal surface of the slide element 284 may also be configured into a sloped or angled surface 304, as shown in FIG. 42B, which may correspond to the tapered interface surface 288 defined along the distal end of the handle 260 to facilitate the release of the slide element 284 from the shaft exterior when pulled proximally.

Additionally, the slide element 284 may further incorporate a projection or shoulder 306 which extends from the slide element 284 for engagement with a corresponding detent or groove defined along the shaft 280. In this variation, the projection or shoulder 306 may extend distally from the slide element 284 upon a flexible member. During delivery, the engagement between the projection or shoulder 306 and shaft 280 may secure a position of the slide element 284 upon the shaft 280. Pulling upon the slide element 284 may simply release the projection or shoulder 306 from the shaft 280.

Figure 43A:
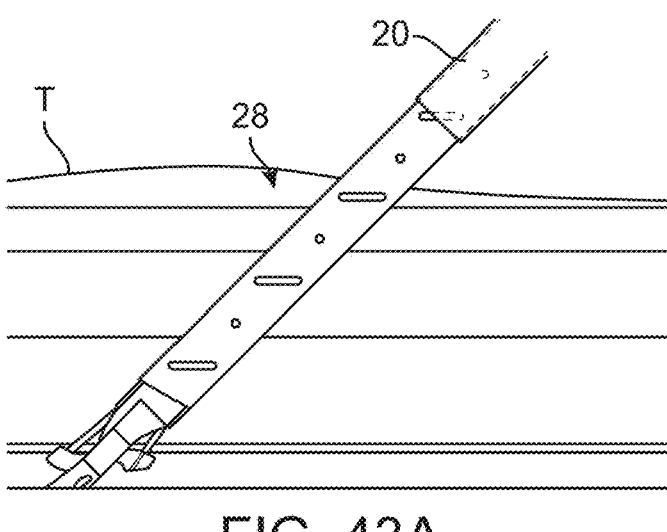
FIG. 43A shows a side view of one variation of the proximal catheter segment incorporating graduations along the outer surface.
Figure 43B:
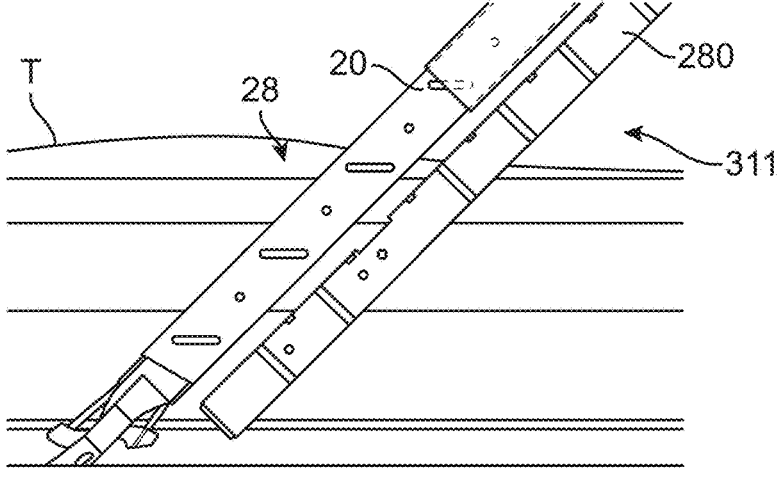
FIGS. 43B and 43C show side views of another variation of the shaft of the suture capture and securement device incorporating graduations along the outer surface.
Figure 43C:
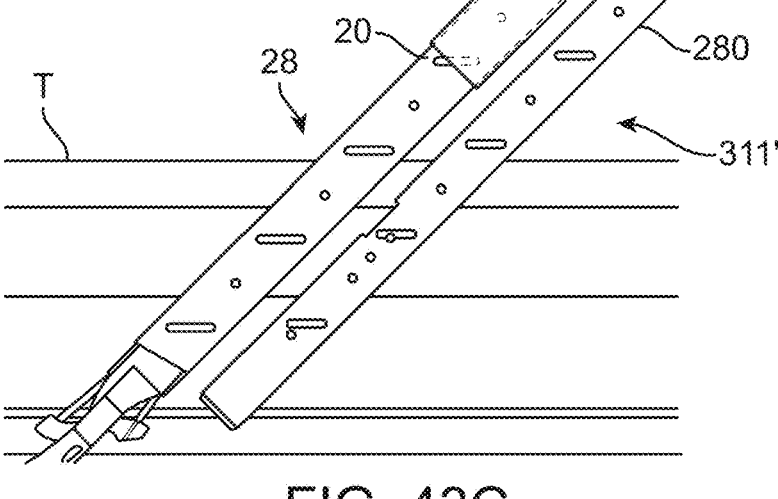

As described above, the proximal catheter segment 20 (and/or distal catheter segment 22) may include graduations 28 upon the outer surface of the catheter to provide a visual indication of the depth of the vessel to be closed relative to the surface of the tissue or skin T, as shown in FIG. 43A. The graduations 28 may be angled (e.g., 30-45 degrees relative to the skin surface), as shown, or straightened relative to the longitudinal axis of the proximal catheter segment 20. FIG. 43B illustrates how the shaft 280 of the suture capture and securement device may also incorporate graduations 311 to similarly provide a visual indication of insertion depth relative to the tissue surface or skin T, as shown. In this variation, the graduations 311 may be configured in a transverse (or straight) configuration relative to a longitudinal axis of the shaft 280, as shown, or they may be angled graduations 311' (e.g., 30-45 degrees relative to the skin surface), as shown in FIG. 43C.

In either the proximal catheter segment 22 or shaft 280, the initial graduation marking may be an initial distance of, e.g., 10 mm, from the receiver member 36 or vessel inner surface and each subsequent graduation marking may be spaced at a uniform distance, e.g., 5-10 mm.

Figure 44:
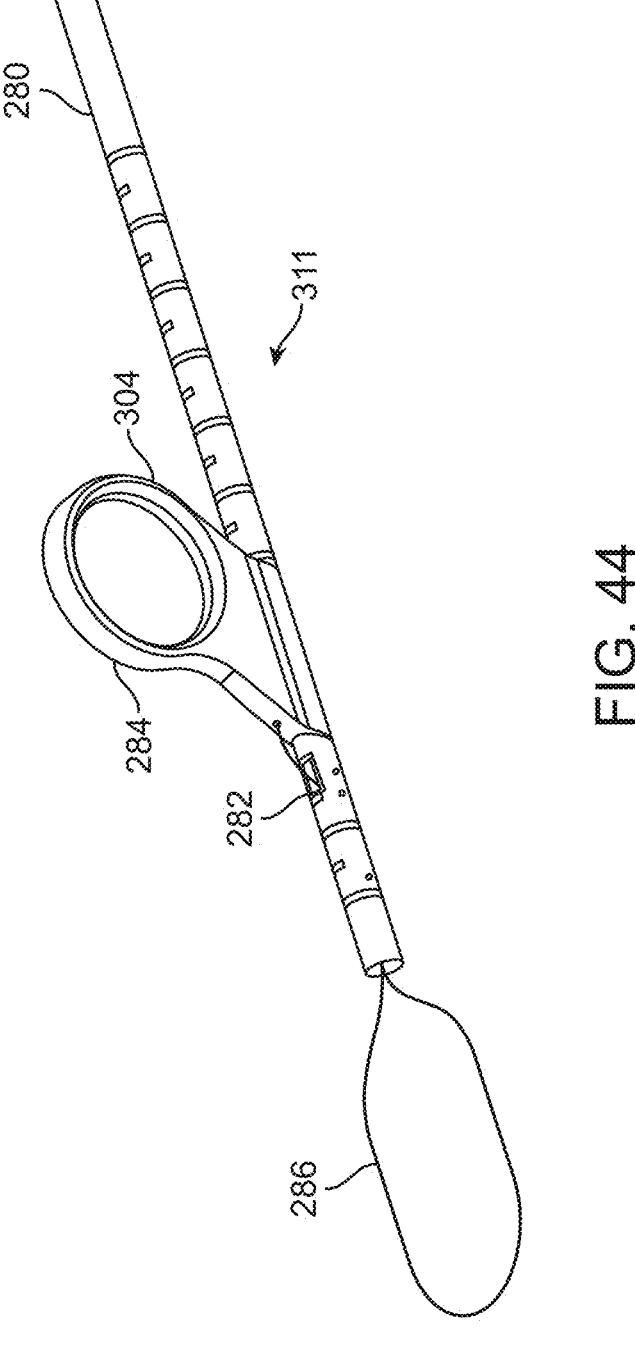
FIG. 44 shows a perspective view of one variation of the shaft incorporating graduations.

FIG. 44 illustrates a perspective view of one variation of the shaft 280 incorporating graduations 311 in which each graduation marking may be, e.g., 5 or 10 mm, separated from one another. The snare loop 286, window 282, and slide element 284 are also shown.

Figure 45A:
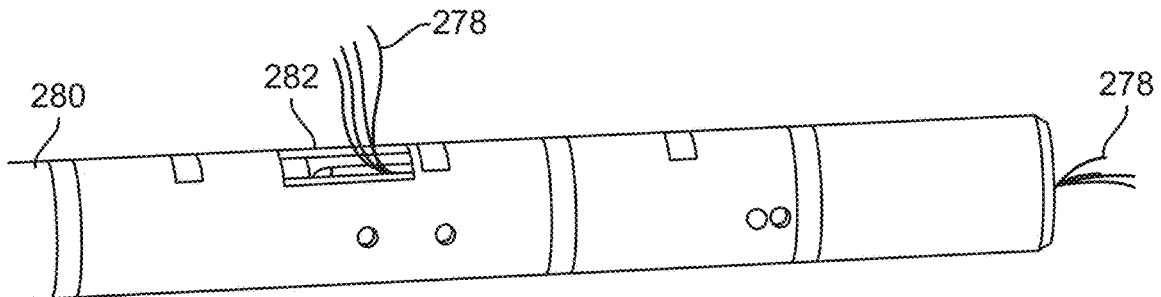
FIGS. 45A to 45D show detail perspective views of the shaft and the internal mechanisms with the outer wall of the shaft removed for clarity purposes.
Figure 45B:
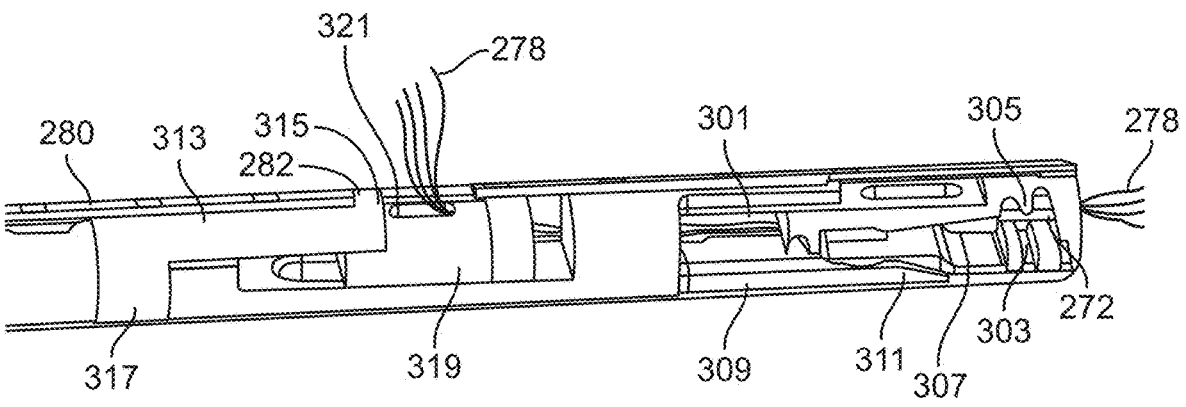

Turning now to the internal suture cutting mechanism, FIGS. 45A and 45B show detail perspective views of the shaft 280 and the internal mechanisms with the outer wall of the shaft 280 removed for clarity purposes. As the suture ends 278 are passed into and through the distal tip of the shaft 280 and out the window 282, as shown in FIG. 45A, the securement anchor 272 may be seen positioned between a deforming platform 303 having one or more transverse projections positioned at the distal end of a cantilevered arm member 307 having a tapered interface surface. A receiving platform 305 also having one or more transverse projections configured in a complementary arrangement with respect to the deforming platform 303 may be seen positioned opposite to the deforming platform 303. The suture 278 may pass through a suture lumen 301 extending between the distal tip of shaft 280 and the window 282. A suture exit port 319 having a cutting interface window 321 may be fixedly positioned within the suture lumen 301 such that the cutting interface window 321 of the exit port 319 is aligned with the window 282 so that the suture ends 278 may pass through the interior of the suture exit port 319 and pass out through the cutting interface window 321 and corresponding window 282. A slidable blade element 313 extending from a base 317 and terminating in a cutting edge 315 may be slidably positioned within the suture lumen 301 such that when the instrument is actuated, e.g., by actuation of handle 262, a pushing mechanism may push upon the base 317 to slidingly move the cutting edge 315 distally over the cutting interface window 321 and window 278 to shear the suture ends 278 accordingly.

Figure 45C:
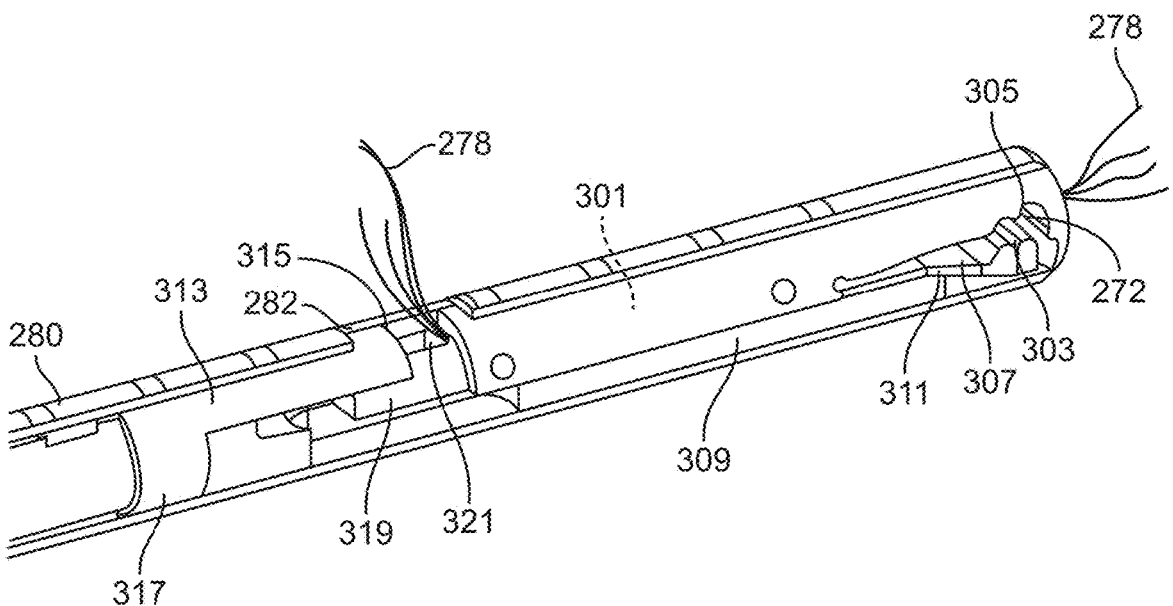
Figure 45D:
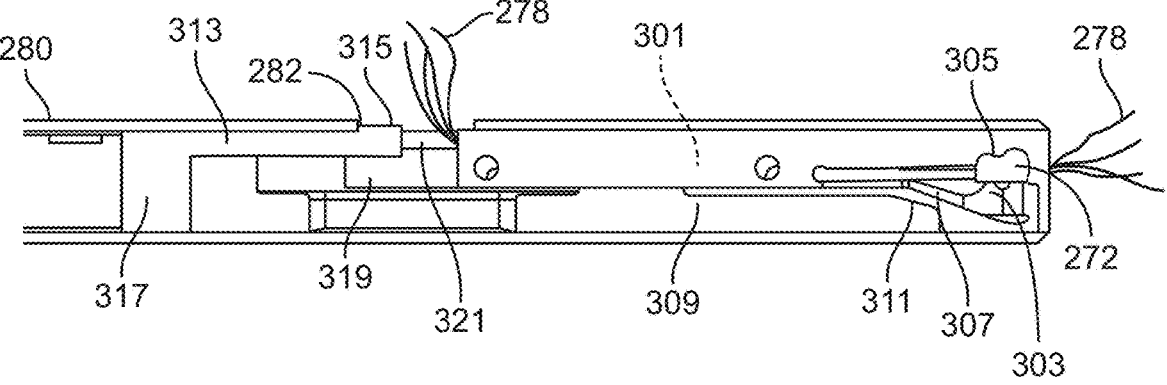

As shown in FIGS. 45C and 45D, which further illustrate perspective and side views of the instrument shaft 280, as the base 317 and cutting edge 315 are translated distally, a translating pusher 309 may be urged distally so that a tapered interface surface 311 at the distal end of the pusher 309 may contact against the cantilevered arm member 307 which is then forced upwards (in a transverse direction). This transverse motion may push the deforming platform 303 towards the receiving platform 305 thereby deforming the securement anchor 272 positioned between the transverse projections of both the deforming platform 303 and receiving platform 305. Hence, in one actuation, the mechanism may secure the anchor 272 as well as trim the suture ends 278 to release the securement anchor 272 upon the approximated tissue. The length of suture (trim length) between the securement anchor 272 and the trimmed location may range, e.g., about 0-3 cm, and represents the suture expected to be left within the patient's body following anchor securement and suture cutting.

Figure 46A:
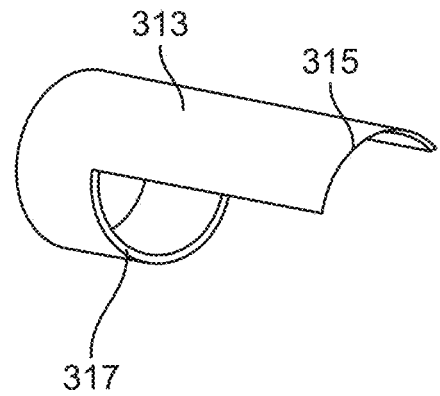
FIGS. 46A and 46B show different perspective views of the base and slidable blade element.
Figure 46B:
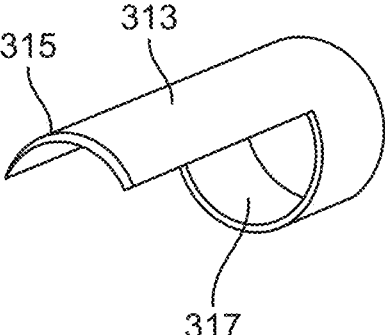

FIGS. 46A and 46B show different perspective views of the base 317 and slidable blade element 313. In the variation shown, the blade element 313 is illustrated as having curved surface to approximate the interior circumference of the shaft 280, but in other variations, the blade element 313 may be shaped in other configurations. Furthermore, while the cutting edge 315 may be a tapered cutting element, other variations may also be used which may incorporate alternative energy delivery mechanisms to cut the suture, e.g., heating elements, rotating elements, etc.

Any of the variations of the suture deployment and delivery mechanisms may be used in any number of combinations or embodiments together with any of the device features described herein including any of the receiver and needle deployment, suture management, suture delivery, tissue management, or suture anchoring features described herein.

Suture Anchoring

As the suture capture and securement device omits the need for any knots or any pre-tied knots, the securement anchor which tightens upon the suture ends and secures the tensioned suture upon the tissue for hemostasis may include any number of deployable ferrules, clips, etc. One particular variation of a securement anchor which may be deployed from the distal opening of the device shaft 280 may include a ferrule which can be sized in any number of configurations depending upon the use case. The ferrule may be sized to capture the suture ends 278 for complete closure and such ferrule structures may be fabricated from any number of materials such as metals which may be deformed (e.g., compressed, crimped, etc.) upon the sutures or polymers which may be heat melted upon the suture for securement. In the event that the sutures used are polymeric, the ferrule may be partially melted along with a portion of the sutures to effect a secure anchor.

Figure 47A:
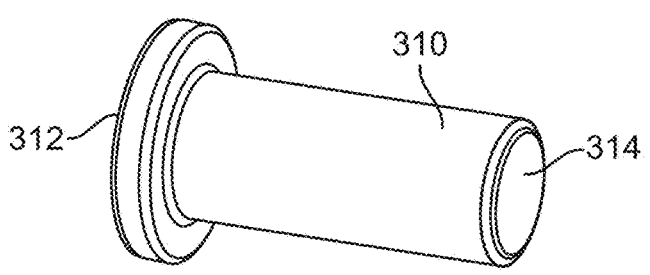
FIGS. 47A-47E show perspective views of various ferrule embodiments.

One variation of a ferrule is shown in the perspective view of FIG. 47A which illustrates a ferrule having a tubular portion 310 which defines a lumen 314 for receiving the sutures through. A distal end of the ferrule may include a flared or enlarged shoulder or shelf 312 which may help to seat and secure a position of the ferrule within the distal opening of the shaft 280. Once the sutures have been passed through the lumen 314 and tensioned, the tubular portion 310 may be deformed or crimped (or heat melted) upon the sutures to prevent their movement. The tubular portion 310 may be optionally curled, angled, or flattened relative to the vessel wall so that the trimmed ends of the suture near or at the opening of the lumen 314 are configured into a low profile for patient comfort.

Figure 47B:
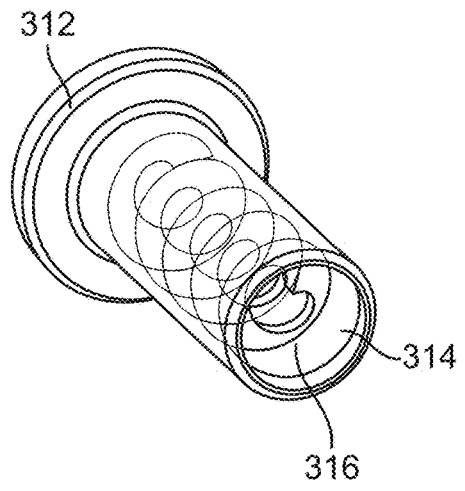
Figure 47C:
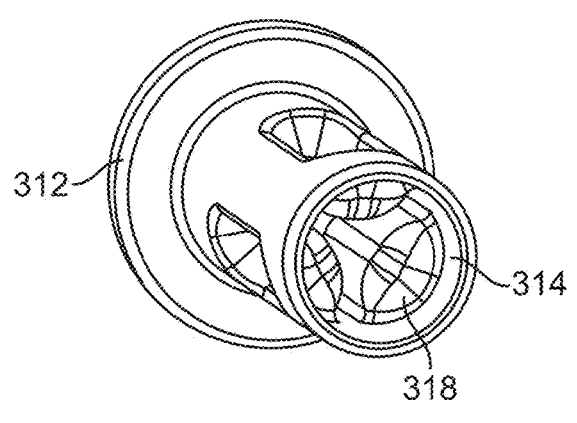

The tubular portion 310 may define a lumen 314 with smooth inner walls, but other variations such as the ferrule in FIG. 47B may incorporate a threaded channel 316. Alternatively, the ferrule lumen 314 may incorporate one or more projections 318 which extend inwardly into the lumen 314, as shown in the ferrule of FIG. 47C, to further enhance the engagement of the ferrule to the sutures when deformed or crimped.

Figure 47D:
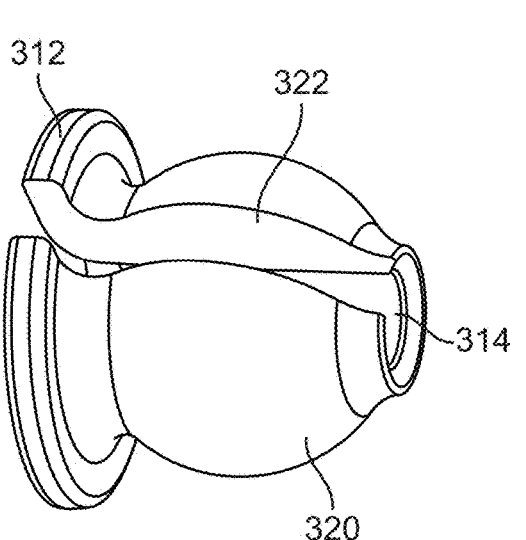
Figure 47E:
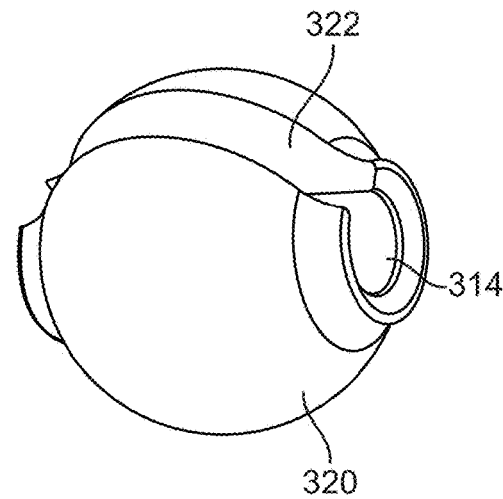

FIGS. 47D and 47E show perspective views of additional ferrule variations which include ball-shaped tubular portions 320 which removes any hard edges for the implant. The ball-shaped ferrules may also define a split or open channel 322 along the length of the tubular portion to facilitate the crimping or collapse of the ferrule upon the sutures. The variation of FIG. 47D also shows the inclusion of the flared or enlarged shoulder or shelf 312 while FIG. 47E omits the shelf 312.

In yet other variations, the ferrule lumen may incorporate a secondary feature which functions as a plug or impingement member where such secondary features may be used to fill the interstitial space within the ferrule to further secure the ferrule upon the sutures. Such secondary features may be made of various materials such as biocompatible plastics (nonabsorbable or absorbable) which are compressible.

Figure 48:
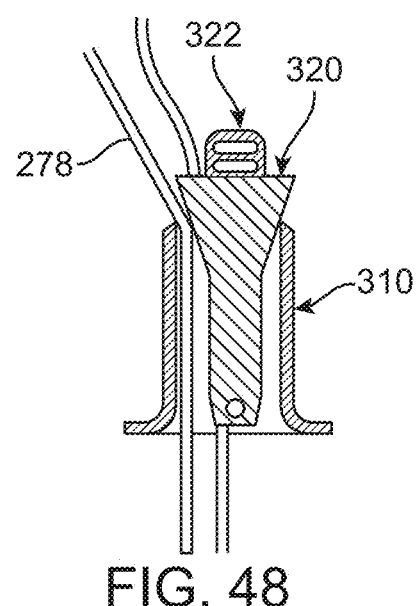
FIG. 48 shows a cross-sectional side view of a ferrule incorporating a releasable plug member.

FIG. 48 shows a partial cross-sectional side view of one variation where the ferrule tubular portion 310 may optionally incorporate a plug 320 (e.g., elastomeric) having a tapered surface which may press against the sutures 278 passing through the lumen. In particular, the tapered surface may help to secure the sutures against the edge of the ferrule, as shown. The plug 320 may further include a pull tab 322 feature which enables the user to grasp the tab 322 and pull the plug 320 from the ferrule for suture release or repositioning.

Figure 49A:
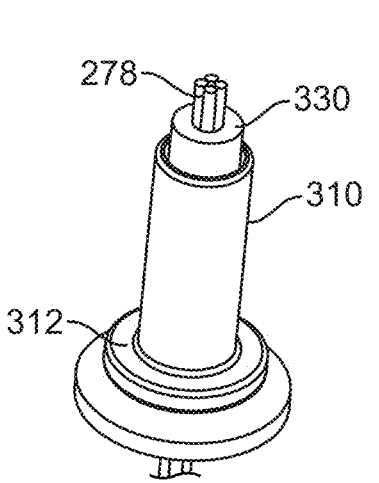
FIGS. 49A and 49B show perspective and cross-sectional perspective views of another ferrule variation incorporating a plug member.
Figure 49B:
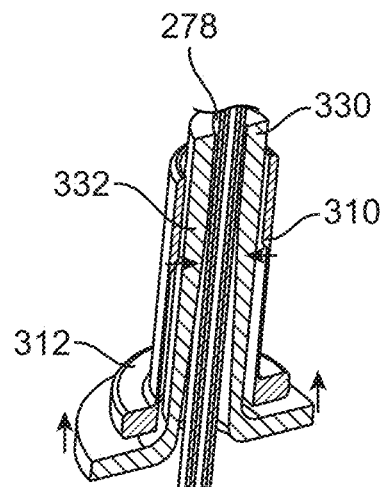

FIGS. 49A and 49B illustrate perspective and cross-sectional perspective views of another variation where a plug 330 defining a plug lumen 332 may be inserted entirely through the ferrule lumen such that the sutures may be passed directly through the plug lumen 332 itself. The plug lumen 332 may also define a tapered lumen which narrows at the proximal end of the plug lumen 332 so that crimping upon the sutures is enhanced.

Figure 50:
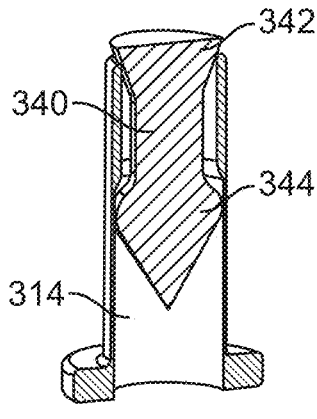
FIG. 50 shows a cross-sectional perspective side view of a ferrule incorporating a plug member variation.

FIG. 50 shows a cross-sectional perspective view of yet another variation where the plug 340 may be introduced into the proximal lumen opening of the ferrule. The plug 340 may include an enlarged proximal end 342 for engagement with the ferrule opening and an enlarged distal feature 344 which is sized for entry within the ferrule lumen 314. With the sutures passed through the ferrule lumen 314, the plug distal feature 344 and proximal end 342 may both facilitate securement of the suture within the ferrule lumen 314 when the plug 340 is pushed into the ferrule lumen 314.

Any of these suture capture and securement feature variations may be used in any number of combinations or embodiments together with any of the device features described herein including any of the receiver and needle deployment, suture management, suture delivery, tissue management, or alternative device embodiments described herein.

The applications of the devices and methods discussed above are not limited to those described but may include any number of suture delivery and tissue securement applications. Modification of the above-described assemblies and methods for carrying out the invention, combinations between different variations as practicable, and variations of aspects of the invention that are obvious to those of skill in the art are intended to be within the scope of the claims.

What is claimed is:

1. A tissue closure apparatus, comprising:
   a handle having one or more actuation mechanisms;
   a proximal catheter segment extending from the handle, wherein the proximal catheter segment further defines a proximal longitudinal axis;
   a deployment segment coupled to the proximal catheter segment;
   a distal catheter segment coupled to the deployment segment such that the distal catheter segment is rotatable at an angle relative to the proximal catheter segment, wherein the distal catheter segment further defines a distal longitudinal axis which is offset relative to the proximal longitudinal axis such that the distal longitudinal axis and the proximal longitudinal axis are non-collinear;
   a receiver member positioned within the deployment segment and having two or more openings along a first receiver portion and two or more openings along a second receiver portion, wherein the receiver member is configurable between a low-profile configuration and a deployed configuration;
   two or more forward needle members which are extendable distally from a first side of the proximal catheter segment and two or more rear needle members which are extendable distally from a second side of the proximal catheter segment opposite to the first side, and
   wherein the two or more forward needle members are receivable into the two or more openings along the first receiver portion and the two or more rear needle members are receivable into the two or more openings along the second receiver portion when the receiver member is in the deployed configuration.

2. The apparatus of claim 1 wherein the proximal catheter segment defines one or more suture lumens within.

3. The apparatus of claim 1 wherein the proximal catheter segment defines openings corresponding to each of the two or more forward needle members and the two or more rear needle members.

4. The apparatus of claim 1 wherein the deployment segment defines a receiving area for retaining the receiver member in the low-profile configuration.

5. The apparatus of claim 1 wherein the deployment segment defines a curved or arcuate profile such that the distal longitudinal axis of the distal catheter segment is offset relative to the proximal longitudinal axis of the proximal catheter segment.

6. The apparatus of claim 1 further comprising a coupling member retained within each of the two or more openings along the first receiver portion and the two or more openings along the second receiver portion.

7. The apparatus of claim 6 wherein each coupling member defines an opening configured to receive a piercing tip from a corresponding needle member in a secure engagement.

8. The apparatus of claim 6 wherein each coupling member is connected to a terminal end of a suture length.

9. The apparatus of claim 6 further comprising a first length of suture coupled to a first coupling member retained within a first opening along the first receiver portion and to a second coupling member retained within a second opening along the second receiver portion.

10. The apparatus of claim 9 further comprising a second length of suture coupled to a third coupling member retained within a third opening along the first receiver portion and to a fourth coupling member retained within a fourth opening along the second receiver portion.

11. The apparatus of claim 1 further comprising one or more tissue dilation elements configured to extend laterally from the proximal catheter segment.

12. The apparatus of claim 1 further comprising a suture anchor device configured to receive one or more lengths of suture deployed from the tissue closure apparatus and secure a tissue securement anchor about the one or more lengths of suture.

13. The apparatus of claim 12 wherein two or more lengths of suture are secured with a single tissue securement anchor.

14. The apparatus of claim 1 further comprising a sheath assembly slidably positioned along the proximal catheter segment, the sheath assembly having a sheath member and a proximal interface member.

15. The apparatus of claim 14 wherein the sheath member is configured to conform to the deployment segment such that the receiver member in the low-profile configuration is encased within the sheath member.

\* \* \* \* \*